(12) United States Patent
Lee et al.

(10) Patent No.: US 11,453,659 B2
(45) Date of Patent: Sep. 27, 2022

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Hanill Lee, Suwon-si (KR); Hyung Sun Kim, Suwon-si (KR); Chang Ju Shin, Suwon-si (KR); Dongkyu Ryu, Suwon-si (KR); Jiah Yoon, Suwon-si (KR); Sung-Hyun Jung, Suwon-si (KR); Handong Chu, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 266 days.

(21) Appl. No.: 16/913,049

(22) Filed: Jun. 26, 2020

(65) Prior Publication Data

US 2020/0407348 A1     Dec. 31, 2020

(30) Foreign Application Priority Data

Jun. 28, 2019   (KR) ........................ 10-2019-0078082

(51) Int. Cl.
*C07D 407/14*   (2006.01)
*C07D 409/14*   (2006.01)
*H01L 51/00*    (2006.01)

(52) U.S. Cl.
CPC ......... *C07D 407/14* (2013.01); *C07D 409/14* (2013.01); *H01L 51/0067* (2013.01); *H01L 51/0072* (2013.01); *H01L 51/0073* (2013.01); *H01L 51/0074* (2013.01)

(58) Field of Classification Search
CPC ............. H01L 51/0067; H01L 51/0072; H01L 51/0073; H01L 51/0074
See application file for complete search history.

(56) References Cited

U.S. PATENT DOCUMENTS

| | | |
|---|---|---|
| 5,061,569 A | 10/1991 | Vanslyke et al. |
| 9,847,501 B2 | 12/2017 | Mizutani et al. |
| 9,876,181 B2 | 1/2018 | Parham et al. |

FOREIGN PATENT DOCUMENTS

| | | |
|---|---|---|
| JP | 1993-009471 A | 1/1993 |
| JP | 1995-126615 A | 5/1995 |
| JP | 1998-095973 A | 4/1998 |
| KR | 10-2014-0046541 A | 4/2014 |
| KR | 10-1423067 B1 | 7/2014 |
| KR | 10-2015-0070860 A | 6/2015 |
| KR | 10-2016-0031371 A | 3/2016 |
| KR | 10-1618409 B1 | 5/2016 |
| KR | 10-2017-0089599 A | 8/2017 |
| KR | 10-2018-0002353 A | 1/2018 |
| KR | 10-2018-0013449 A | 2/2018 |
| KR | 10-1849747 B1 | 5/2018 |
| KR | 10-1947747 B1 | 2/2019 |
| WO | WO 1995-009147 A | 4/1995 |

*Primary Examiner* — Anthony Ho
(74) *Attorney, Agent, or Firm* — Lee IP Law, P.C.

(57) ABSTRACT

A compound for an organic optoelectronic device, a composition for an organic optoelectronic device, an organic optoelectronic device, and a display device, the compound for an organic optoelectronic device being represented by the following Chemical Formula 1:

(Continued)

[Chemical Formula 1]
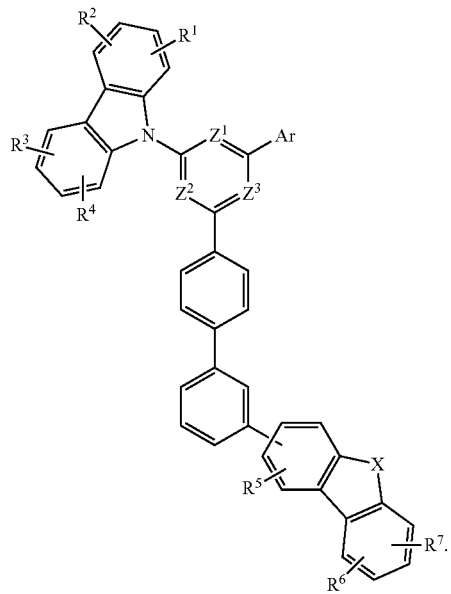
17 Claims, 1 Drawing Sheet

COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATION

Korean Patent Application No. 10-2019-0078082, filed on Jun. 28, 2019, in the Korean Intellectual Property Office, and entitled: "Compound for Organic Optoelectronic Device, Composition for Organic Optoelectronic Device, Organic Optoelectronic Device and Display Device," is incorporated by reference herein in its entirety.

BACKGROUND

1. Field

A compound for an organic optoelectronic device, a composition for an organic optoelectronic device, an organic optoelectronic device, and a display device are disclosed.

2. Description of the Related Art

An organic optoelectronic device (e.g., organic optoelectronic diode) is a device that converts electrical energy into photoenergy, and vice versa.

An organic optoelectronic device may be classified as follows in accordance with its driving principles. One is a photoelectric diode where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and performance of an organic light emitting diode may be affected by organic materials disposed between electrodes.

SUMMARY

The embodiments may be realized by providing a compound for an organic optoelectronic device, the compound being represented by Chemical Formula 1,

[Chemical Formula 1]

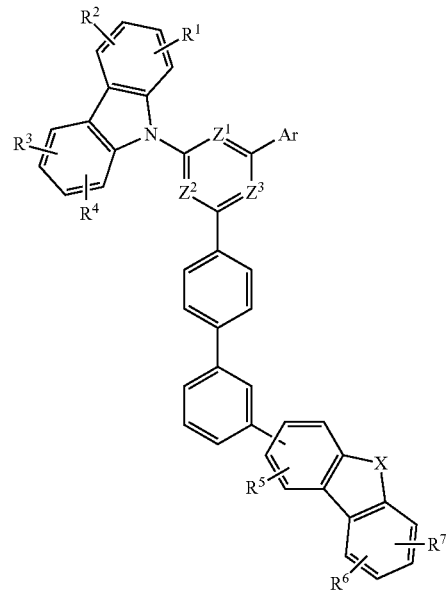

wherein, in Chemical Formula 1, X is O or S, $Z^1$ to $Z^3$ are independently N or $CR^a$, at least two of $Z^1$ to $Z^3$ being N, Ar is a substituted or unsubstituted C6 to C18 aryl group, and $R^a$ and $R^1$ to $R^7$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

The embodiments may be realized by providing a composition for an organic optoelectronic device, the composition including a first compound and a second compound, wherein the first compound includes the compound according to an embodiment, the second compound is represented by Chemical Formula 2,

[Chemical Formula 2]

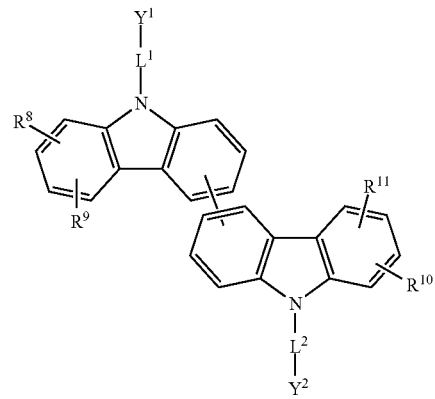

in Chemical Formula 2, $L^1$ and $L^2$ are independently a single bond or a substituted or unsubstituted C6 to C30 arylene group, $Y^1$ and $Y^2$ are independently a substituted or unsubstituted C6 to C30 aryl group, a substituted or unsubstituted C2 to C30 heterocyclic group, or a combination thereof, and $R^8$ to $R^{11}$ are independently hydrogen, deuterium, a cyano group, a halogen, a substituted or unsubstituted C1 to C10 alkyl group, a substituted or unsubstituted C6 to C12 aryl group, or a combination thereof.

The embodiments may be realized by providing an organic optoelectronic device including an anode and a cathode facing each other, at least one organic layer between the anode and the cathode, wherein the at least one organic layer includes the compound according to an embodiment.

The embodiments may be realized by providing an organic optoelectronic device including an anode and a cathode facing each other, at least one organic layer between the anode and the cathode, wherein the at least one organic layer includes the composition according to an embodiment.

The embodiments may be realized by providing a display device including the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
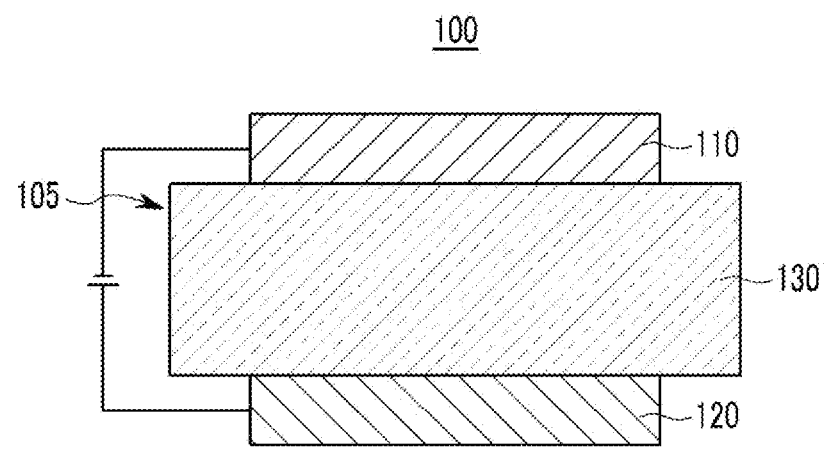
FIGS. 1 and 2 are cross-sectional views showing organic light emitting diodes according to embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

In the present specification, when a definition is not otherwise provided, "substituted" refers to replacement of at least one hydrogen of a substituent or a compound by deuterium, a cyano group, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, or a combination thereof.

In one example, the "substituted" refers to replacement of at least one hydrogen of a substituent or a compound by deuterium, a cyano group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples, the "substituted" refers to replacement of at least one hydrogen of a substituent or a compound by deuterium, a cyano group, a C1 to C20 alkyl group, or a C6 to C30 aryl group. In addition, specific examples, the "substituted" refers to replacement of at least one hydrogen of a substituent or a compound by deuterium, a cyano group, a C1 to C5 alkyl group, or a C6 to C18 aryl group. In addition, specific examples, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

In the present specification when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but is not limited thereto.

In the specification, hole characteristics refer to an ability to donate an electron to form a hole when an electric field is applied and that a hole formed in the anode may be easily injected into the light emitting layer, and a hole formed in a light emitting layer may be easily transported into an anode and transported in the light emitting layer due to conductive characteristics according to a highest occupied molecular orbital (HOMO) level.

In addition, electron characteristics refer to an ability to accept an electron when an electric field is applied and that an electron formed in a cathode may be easily injected into the light emitting layer, and an electron formed in a light emitting layer may be easily transported into a cathode and transported in the light emitting layer due to conductive characteristics according to a lowest unoccupied molecular orbital (LUMO) level.

A compound for an organic optoelectronic device according to an embodiment may be represented by Chemical Formula 1.

[Chemical Formula 1]

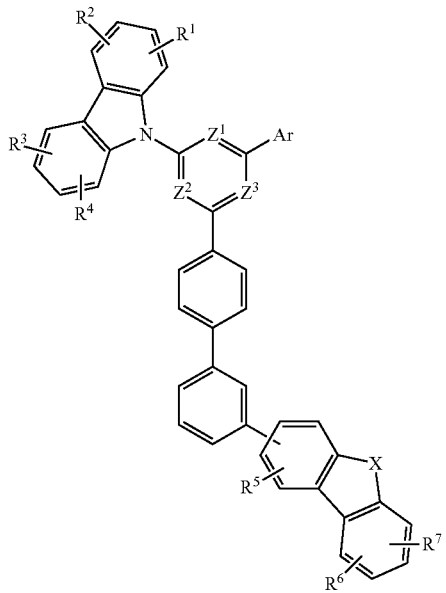

In Chemical Formula 1, X may be, e.g., O or S. $Z^1$ to $Z^3$ may each independently be, e.g., N or $CR^a$. In an implementation, at least two of $Z^1$ to $Z^3$ may be N.

Ar may be or may include, e.g., a substituted or unsubstituted C6 to C18 aryl group.

$R^a$ and $R^1$ to $R^7$ may each independently be or include, e.g., hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

The compound represented by Chemical Formula 1 may have a structure in which N-carbazole, an aryl group, and a dibenzofuranyl group (or dibenzothiophenyl group) are substituted in or on the center of a nitrogen-containing hexagonal (6-membered) ring.

In an implementation, the dibenzofuranyl group (or dibenzothiophenyl group) may be linked to the nitrogen-containing hexagonal ring through a biphenylene moiety. In an implementation, the biphenylene group may be linked to the dibenzofuranyl group (or dibenzothiophenyl group) with a p-phenylene-m-phenylene structure from the nitrogen-containing hexagonal ring. In an implementation, a substituted or unsubstituted N-carbazole moiety and a substituted or unsubstituted aryl moiety are connected to a nitrogen-containing hexagonal ring, which is connected to a substituted or unsubstituted p-phenylene-m-phenylene moiety, which is connected to a substituted or unsubstituted dibenzofuranyl (or dibenzothiophenyl) moiety.

The structure may include a series of three hexagonal rings (including the nitrogen-containing hexagonal ring and biphenylene), one of which is composed of pyrimidine or triazine, and thus may have a low T1 value.

In an implementation, the N-carbazole may be directly linked to the nitrogen-containing hexagonal ring in the 'N' direction (e.g., at the nitrogen of the carbazole group), the π-bond may be broken and the LUMO electron cloud may not be expanded, thereby preventing an increase of the T1 value and helping to maintain the low T1 value.

The lower T1 value may help lower an exciton barrier, thereby increasing the efficiency of a device to which it is applied and increasing life-span at low driving voltage.

The hexagonal ring including $Z^1$ to $Z^3$ may be, e.g., a pyrimidine ring or a triazine ring.

Ar may be or may include, e.g., a substituted or unsubstituted C6 to C18 aryl group (e.g., may have 6 to 18 carbon atoms other than carbon atoms included in substituents). In an implementation, Ar may be or may include, e.g., a substituted or unsubstituted phenyl group, a substituted or unsubstituted biphenyl group, or a substituted or unsubstituted terphenyl group.

Here, "substituted" refers to replacement of at least one hydrogen by deuterium, a cyano group, a nitro group, a halogen, a C1 to C30 alkyl group, or a combination thereof, e.g., replacement of at least one hydrogen by deuterium, a cyano group, a C1 to C10 alkyl group, or a combination thereof.

In an implementation, Ar may be a substituent or group of the following Group I (in which * is a linking point).

[Group I]

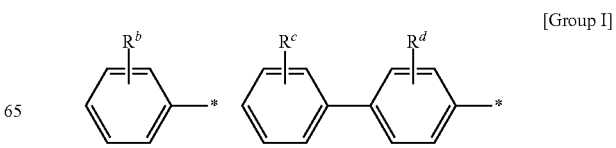

-continued

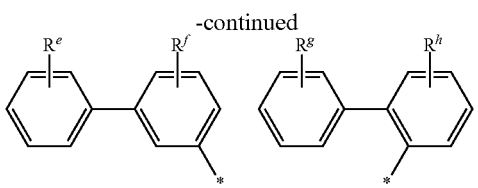

In Group I, $R^b$, $R^c$, $R^d$, $R^e$, $R^f$, $R^g$, and $R^h$ may each independently be or include, e.g., hydrogen, deuterium, a cyano group, a nitro group, a halogen, a substituted or unsubstituted C1 to C30 alkyl group, or a combination thereof.

In an implementation, the compound represented by Chemical Formula 1 may be represented by, e.g., one of Chemical Formula 1-1 to Chemical Formula 1-4, depending on the specific linking point of dibenzofuran (or dibenzothiophene) with biphenylene linked to the nitrogen-containing hexagonal ring.

[Chemical Formula 1-1]

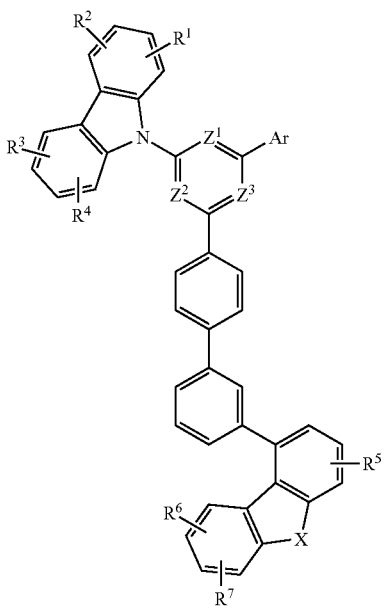

[Chemical Formula 1-2]

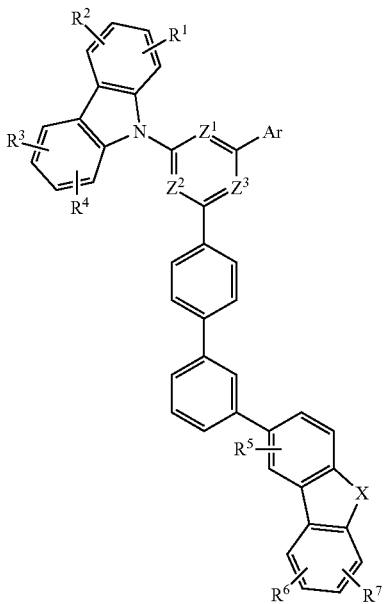

[Chemical Formula 1-3]

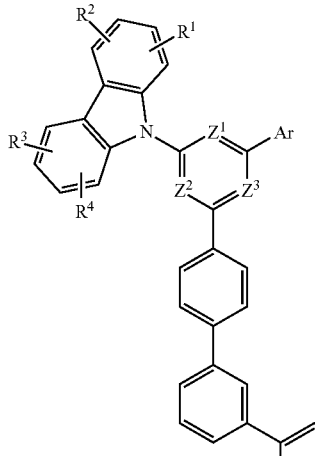

[Chemical Formula 1-4]

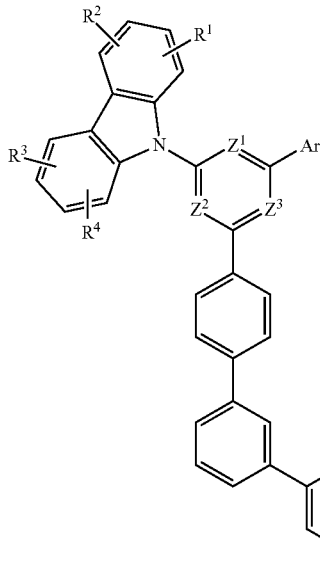

In Chemical Formula 1-1 to Chemical Formula 1-4, X, $Z^1$ to $Z^3$, Ar, and $R^1$ to $R^7$ may be defined the same as those of Chemical Formula 1.

In an implementation, $R^5$ to $R^7$ may be a substituent substituted at a specific position of dibenzofuran (or dibenzothiophene). In an implementation, the compound represented by Chemical Formula 1-1 may be represented by, e.g., one of Chemical Formula 1-1a to Chemical Formula 1-1d, according to the substitution position of $R^7$ on the dibenzofuran (or dibenzothiophene).

[Chemical Formula 1-1a]

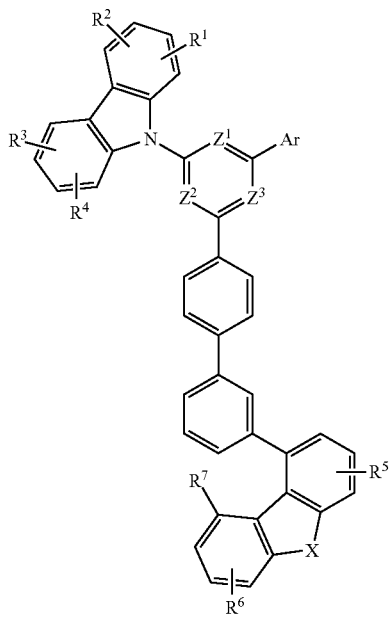

[Chemical Formula 1-1b]

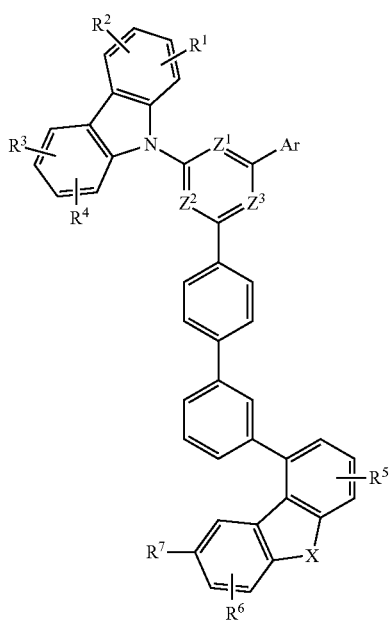

[Chemical Formula 1-1c]

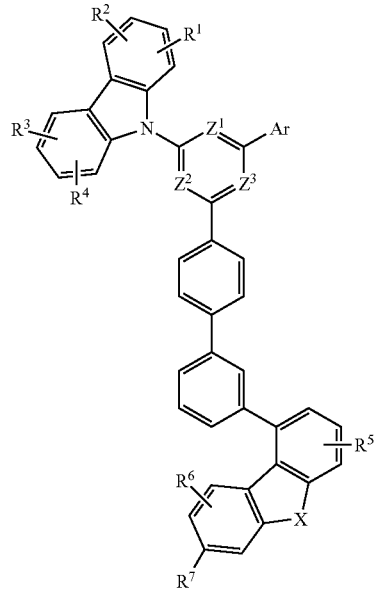

[Chemical Formula 1-1d]

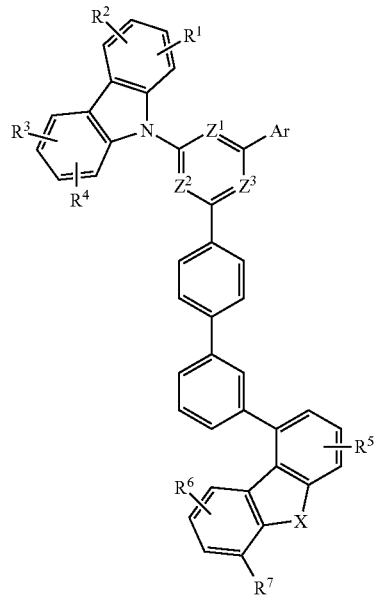

In Chemical Formula 1-1a to Chemical Formula 1-1d, X, $Z^1$ to $Z^3$, Ar, and $R^1$ to $R^7$ may be defined the same as those of Chemical Formula 1. In an implementation, $R^7$ may be or may include, e.g., deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

In an implementation, the compound represented by Chemical Formula 1-2 may be represented by, e.g., one of Chemical Formula 1-2a to Chemical Formula 1-2d, according to the substitution position of $R^7$ on the dibenzofuran (or dibenzothiophene).

[Chemical Formula 1-2a]

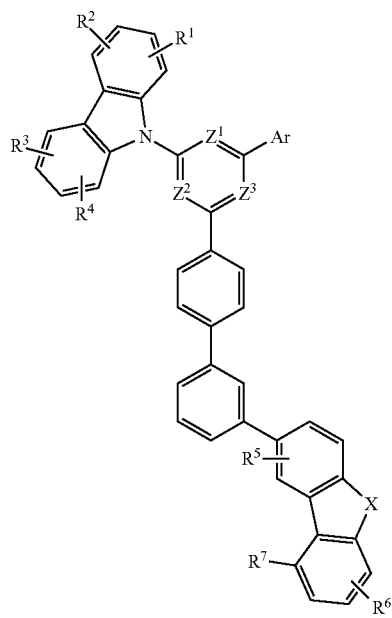

[Chemical Formula 1-2b]

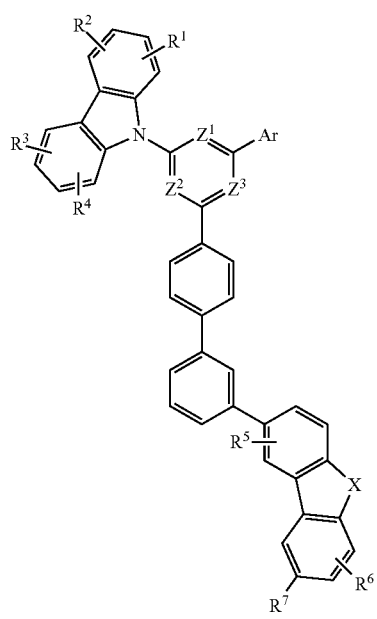

[Chemical Formula 1-2c]

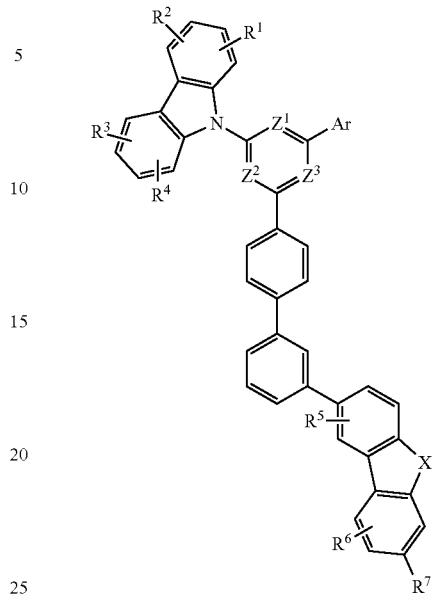

[Chemical Formula 1-2d]

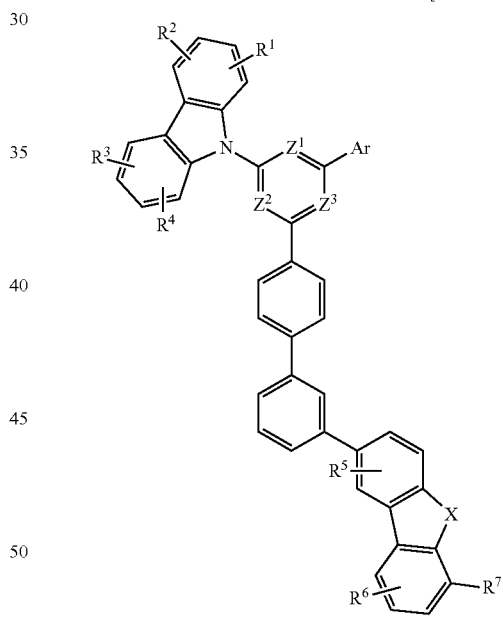

In Chemical Formula 1-2a to Chemical Formula 1-2d, X, $Z^1$ to $Z^3$, Ar, and $R^1$ to $R^7$ may be defined the same as those of Chemical Formula 1. In an implementation, $R^7$ may be or may include, e.g., deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof In an implementation, the compound represented by Chemical Formula 1-3 may be represented by, e.g., one of Chemical Formula 1-3a to Chemical Formula 1-3d, according to the substitution position of $R^7$ on the dibenzofuran (or dibenzothiophene).

[Chemical Formula 1-3a]

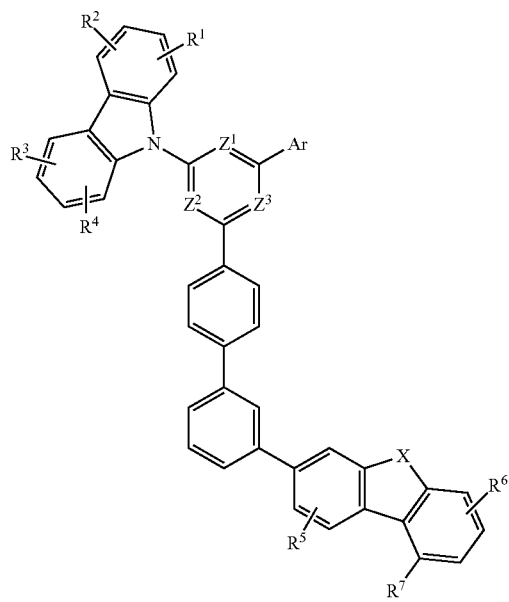

[Chemical Formula 1-3b]

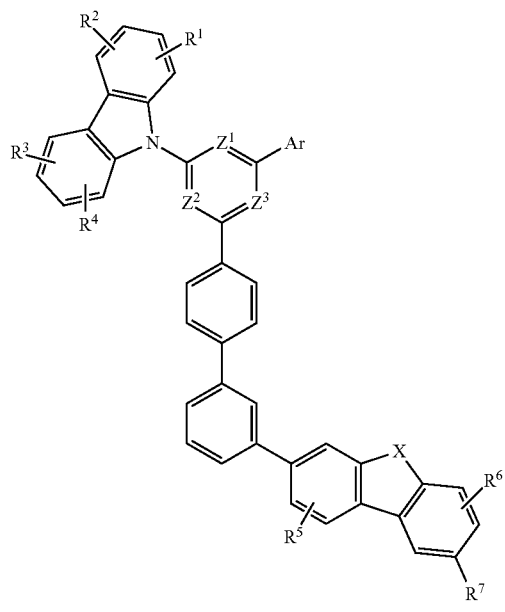

[Chemical Formula 1-3c]

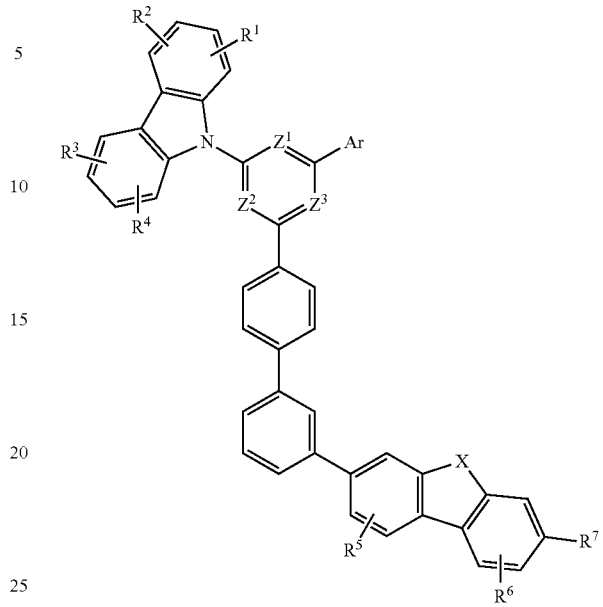

[Chemical Formula 1-3d]

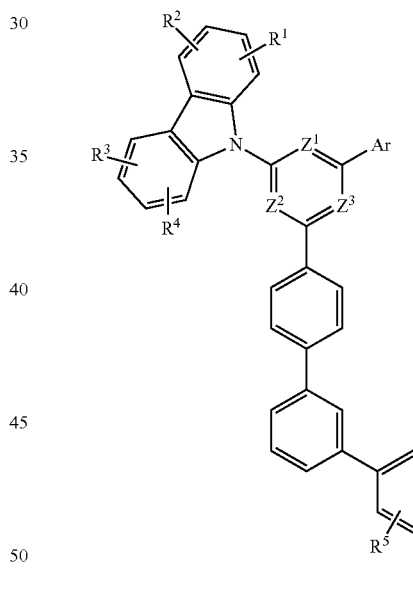

In Chemical Formula 1-3a to Chemical Formula 1-3d, X, $Z^1$ to $Z^3$, Ar, and $R^1$ to $R^7$ may be defined the same as those of Chemical Formula 1. In an implementation, $R^7$ may be or may include, e.g., deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof In an implementation, the compound represented by Chemical Formula 1-4 may be represented by, e.g., one of Chemical Formula 1-4a to Chemical Formula 1-4d, according to the substitution position of $R^7$ on the dibenzofuran (or dibenzothiophene).

[Chemical Formula 1-4a]

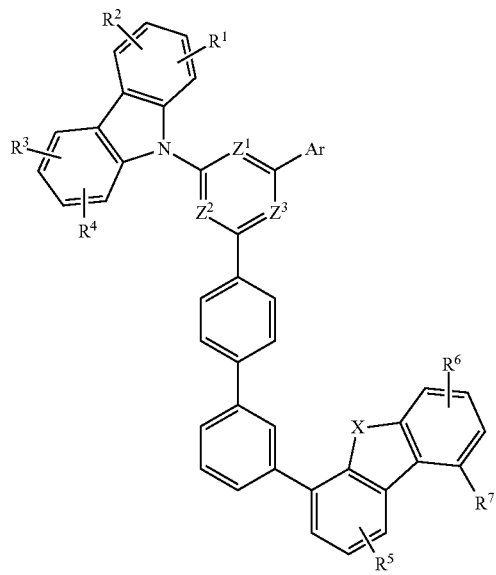

[Chemical Formula 1-4b]

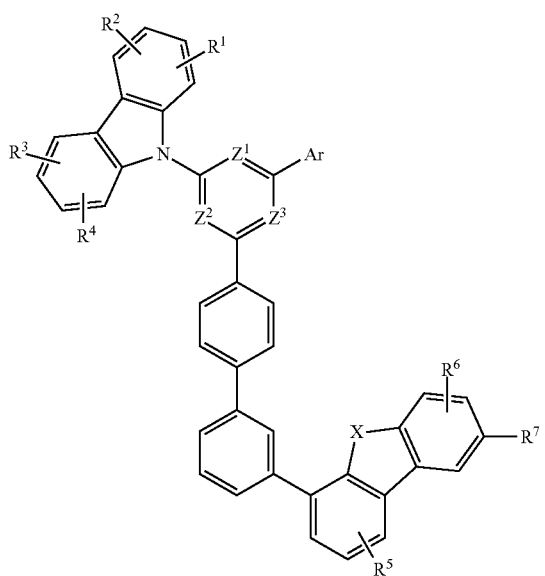

[Chemical Formula 1-4c]

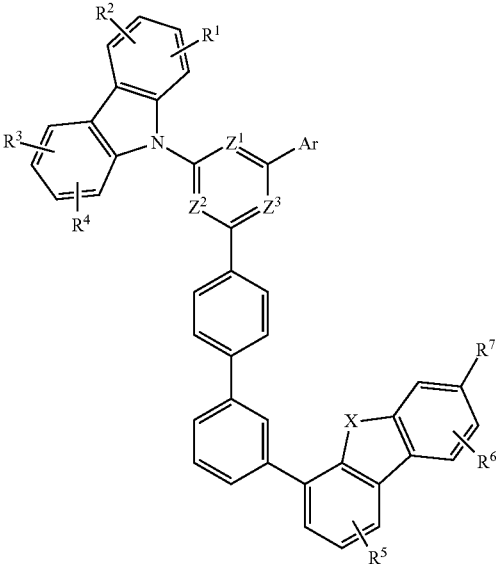

[Chemical Formula 1-4d]

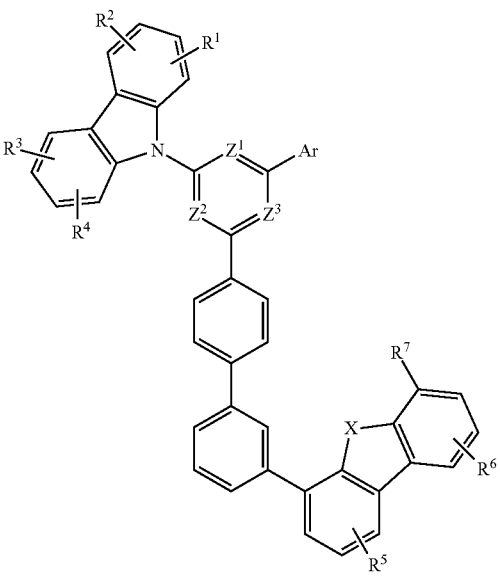

In Chemical Formula 1-4a to Chemical Formula 1-4d, X, $Z^1$ to $Z^3$, Ar, and $R^1$ to $R^7$ may be defined the same as those of Chemical Formula 1. In an implementation, $R^7$ may be or may include, e.g., deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

In an implementation, $R^1$ to $R^4$ may each independently be or include, e.g., hydrogen, deuterium, a cyano group, a halogen, a substituted or unsubstituted C1 to C10 alkyl group, a substituted or unsubstituted C6 to C12 aryl group, or a combination thereof. In an implementation, $R^1$ to $R^4$ may each independently be or include, e.g., hydrogen, deuterium, a cyano group, a substituted or unsubstituted C1 to C10 alkyl group, a substituted or unsubstituted C6 to C12 aryl group, or a combination thereof. In an implementation, $R^1$ to $R^4$ may all be hydrogen.

In an implementation, $R^5$ to $R^7$ may each independently be or include, e.g., hydrogen, deuterium, a cyano group, a halogen, a substituted or unsubstituted C1 to C10 alkyl group, a substituted or unsubstituted C6 to C12 aryl group, or a combination thereof. In an implementation, $R^5$ to $R^7$ may each independently be or include, e.g., hydrogen, deuterium, a cyano group, a substituted or unsubstituted C6 to C12 aryl group, or a combination thereof. In an implementation, $R^5$ to $R^7$ may be all hydrogen or one of $R^5$ to $R^7$ may be a cyano group or a substituted or unsubstituted phenyl group.

In an implementation, the compound represented by Chemical Formula 1 may be represented by, e.g., one of Chemical Formula 1-1a, Chemical Formula 1-1b, Chemical Formula 1-3a, Chemical Formula 1-3b, Chemical Formula 1-4a, and Chemical Formula 1-4b.

In an implementation, the compound represented by Chemical Formula 1 may be represented by, e.g., Chemical Formula 1-3a or Chemical Formula 1-4a.

In an implementation, the compound represented by Chemical Formula 1 may be, e.g., a compound of the following Group 1.

[Group 1]

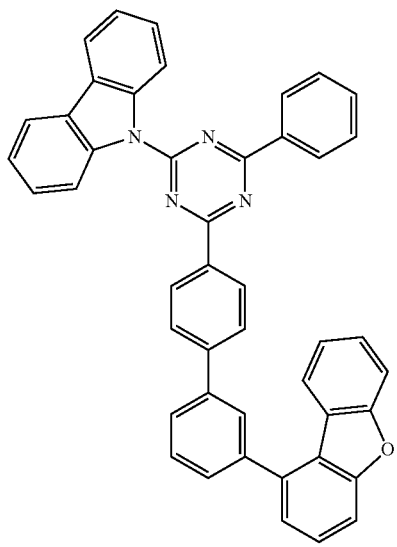

1

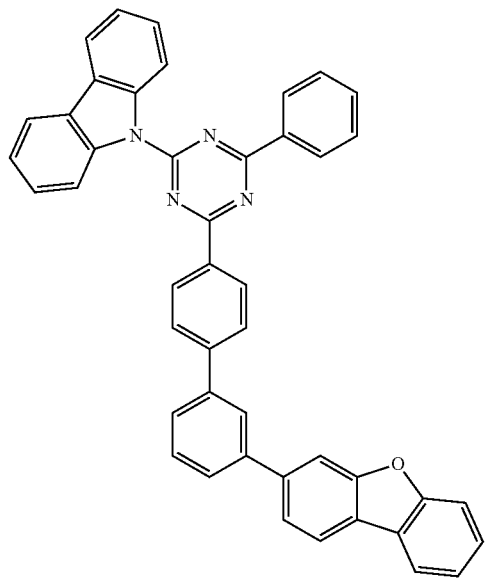

2

3

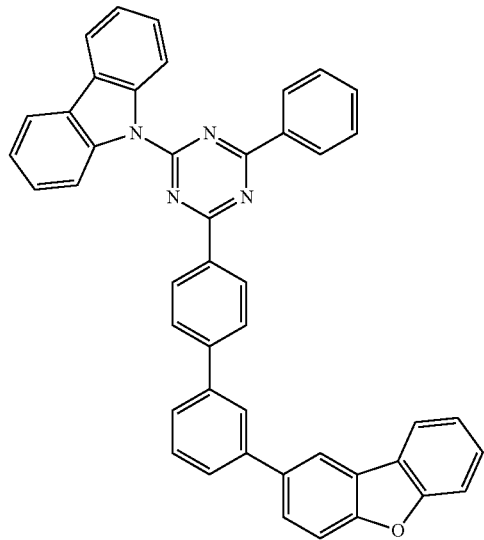

4

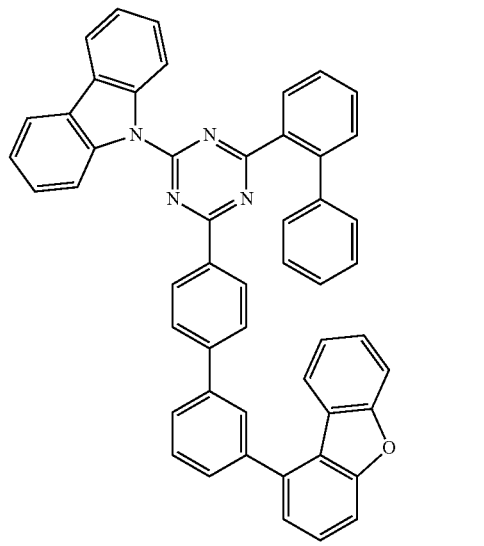

5

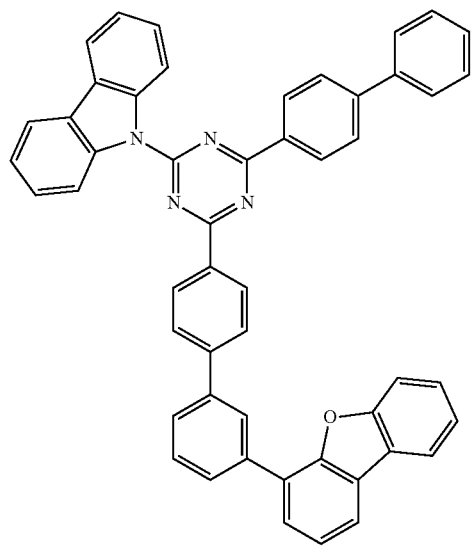
6
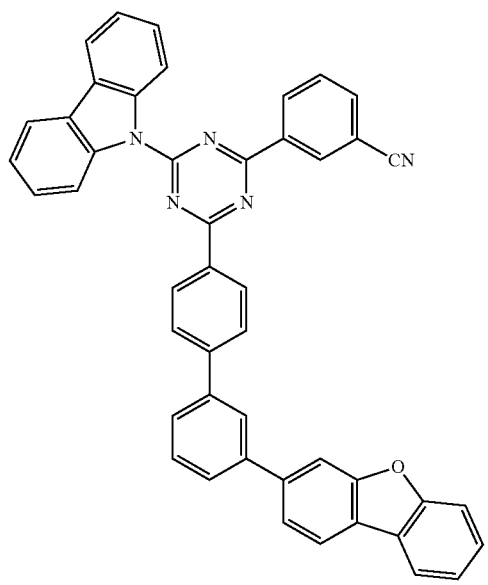
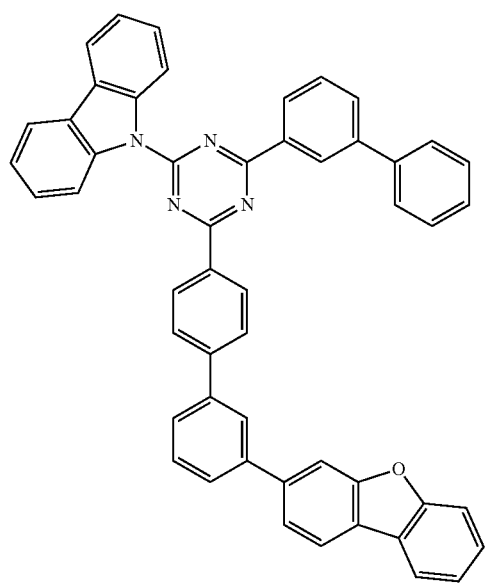
7
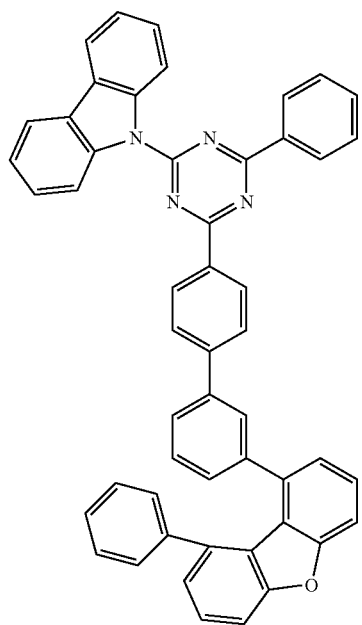

10
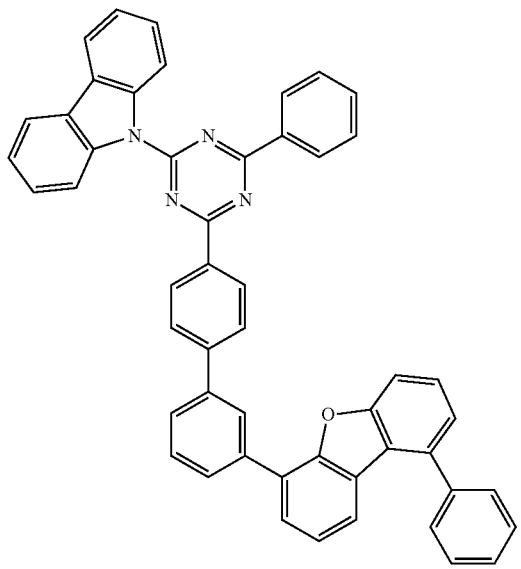
11
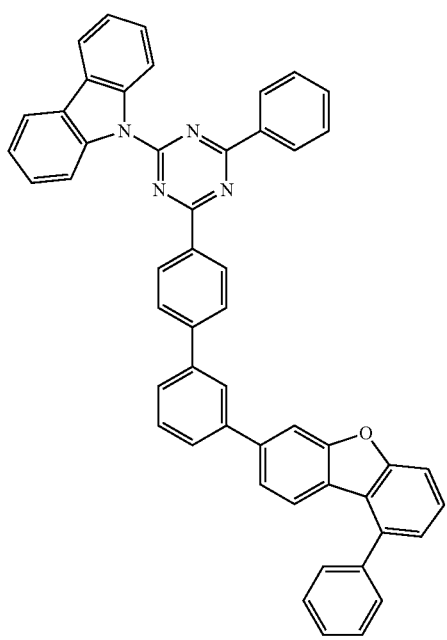
12
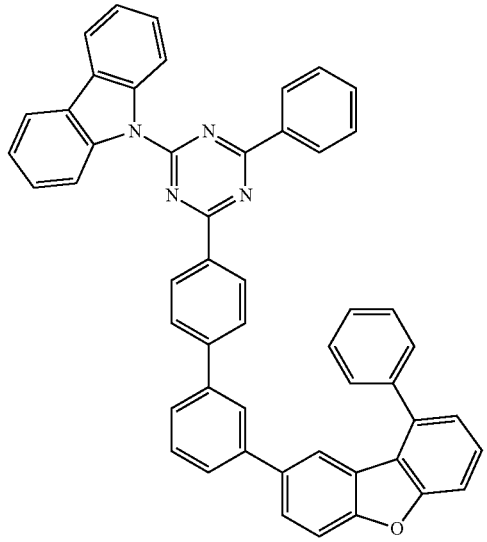
13
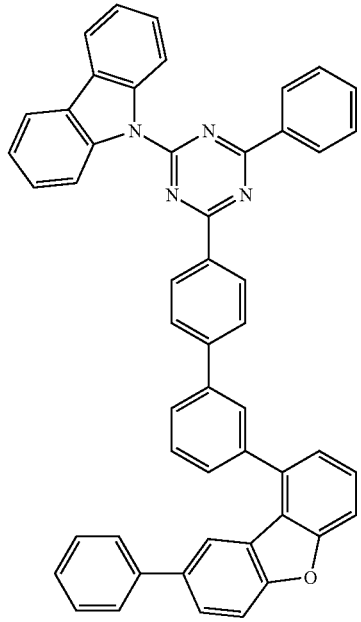

14
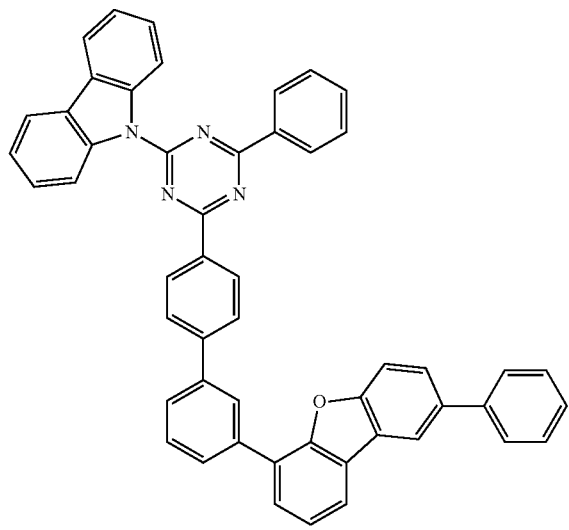
16
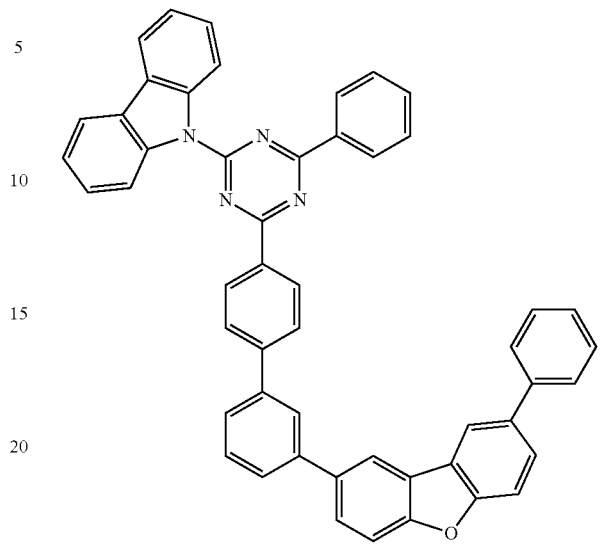
15
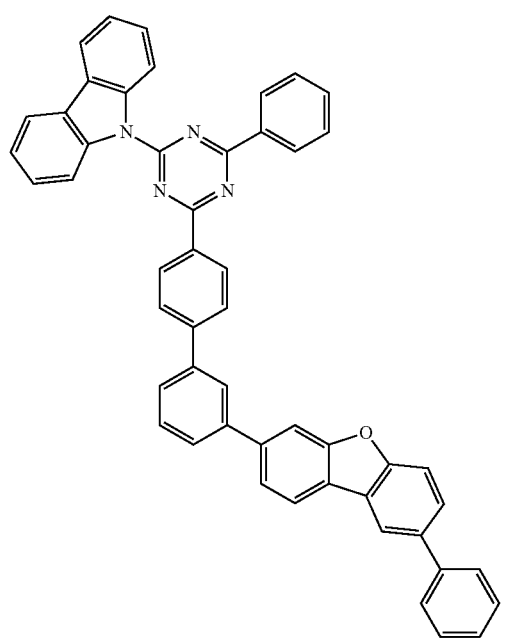
17
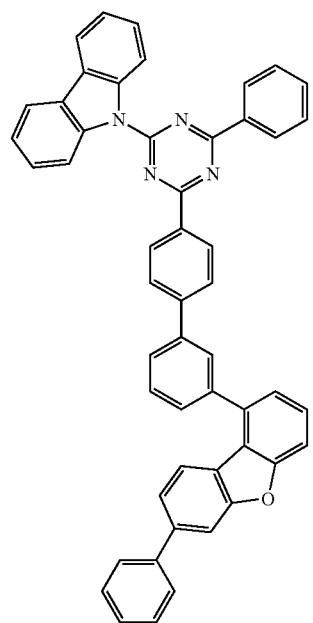

18
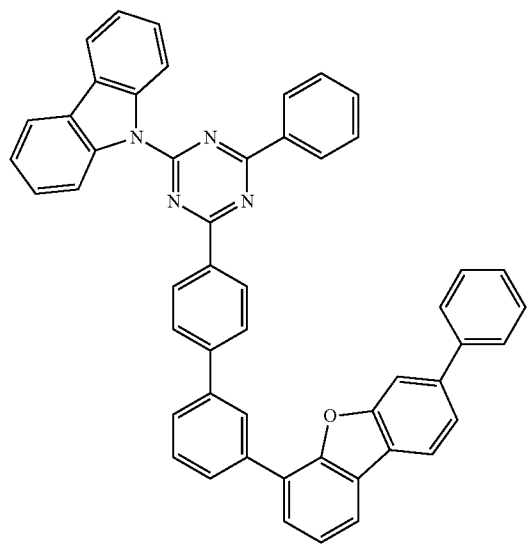
19
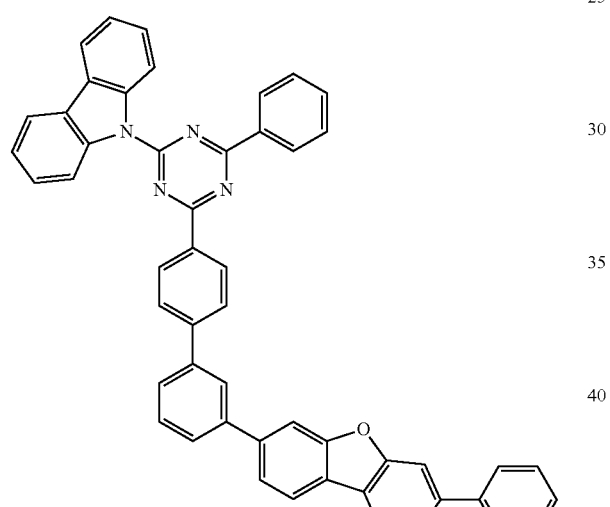
20
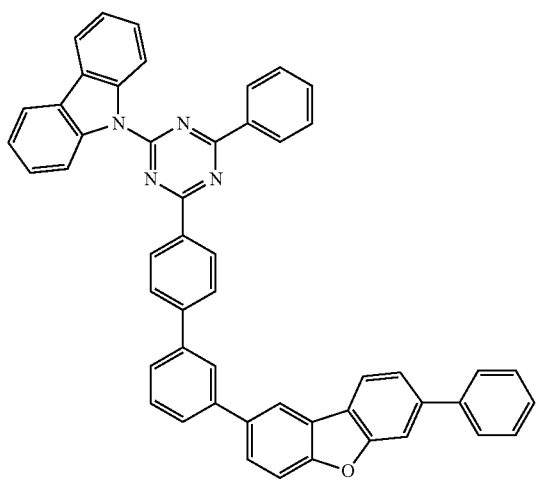
21
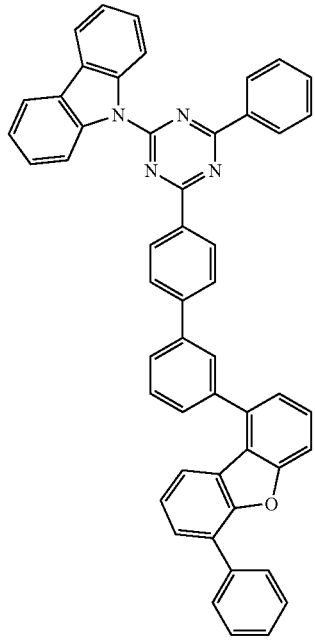
22
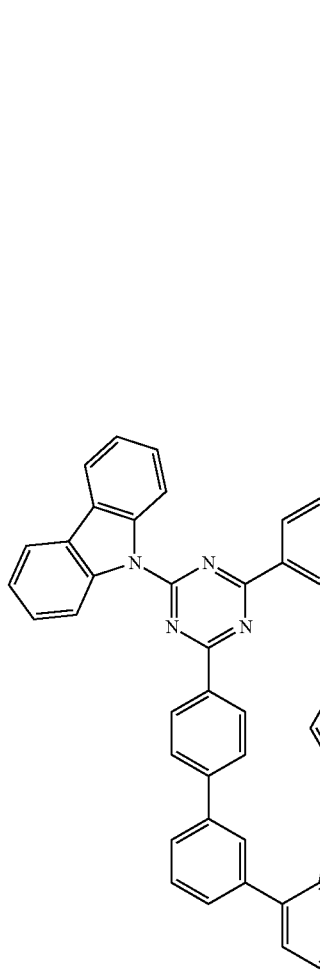

23
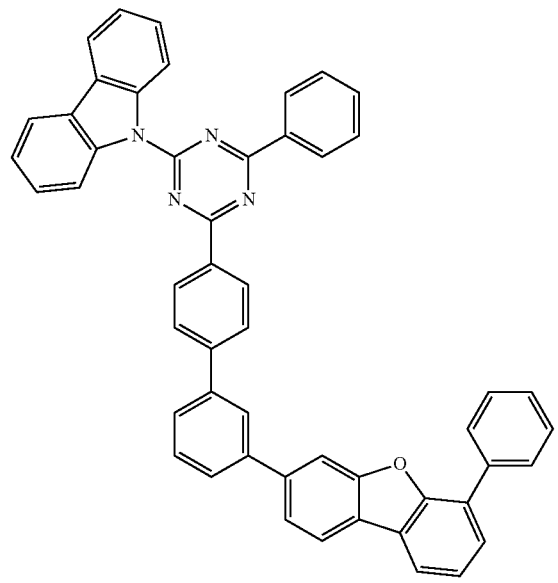
24
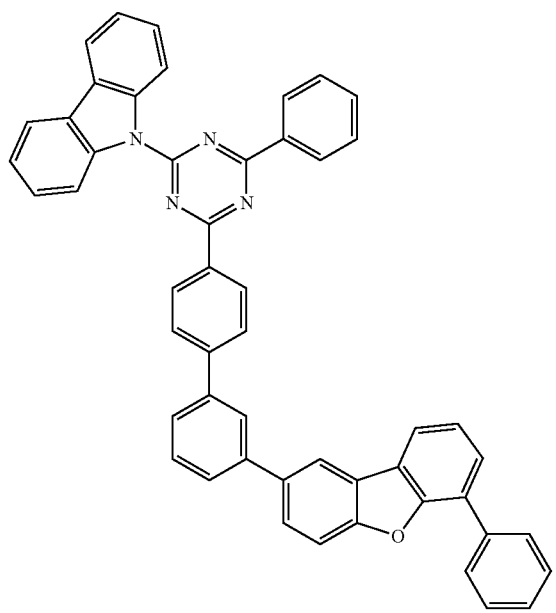
25
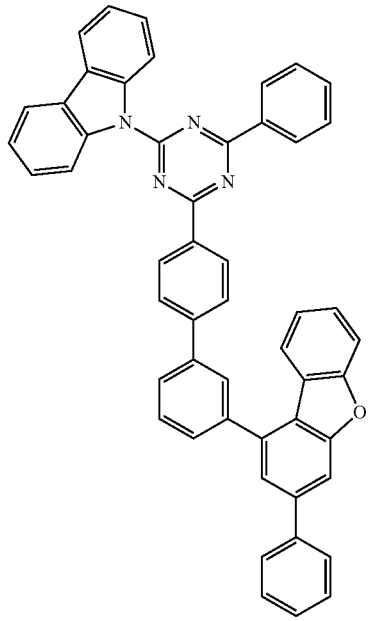
26
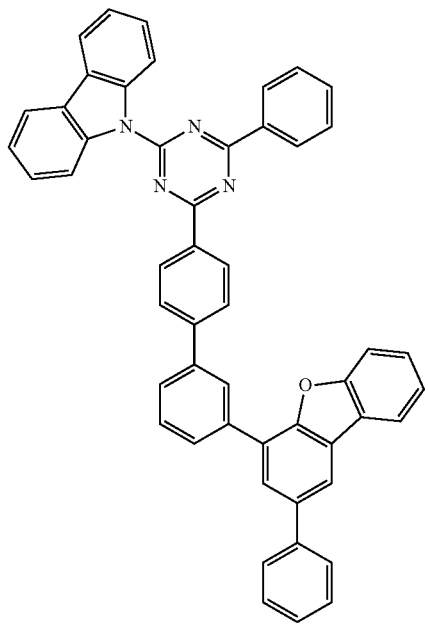

27
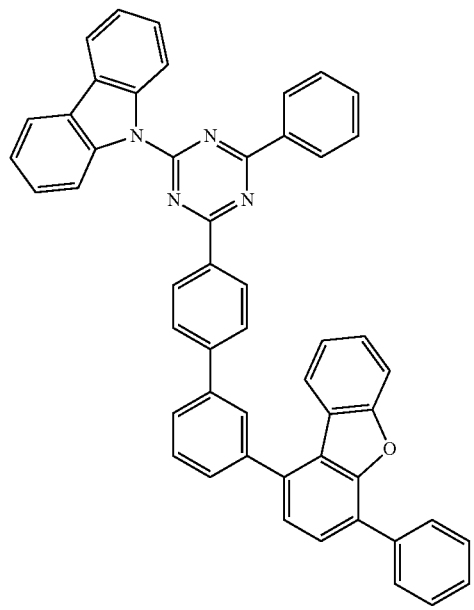
28
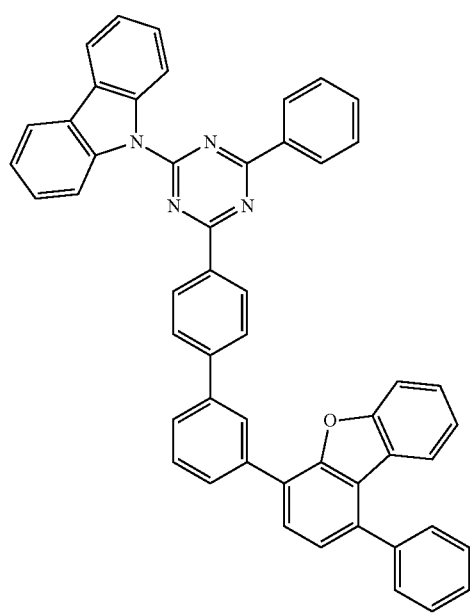
29
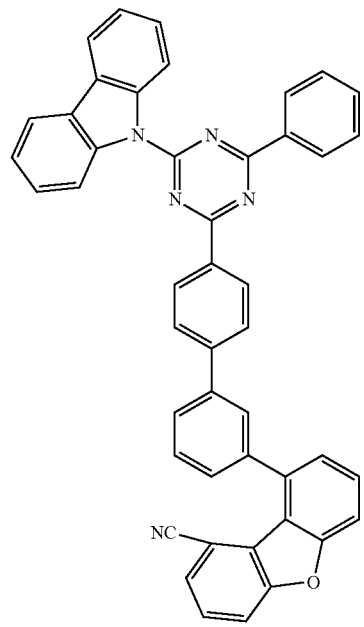
30
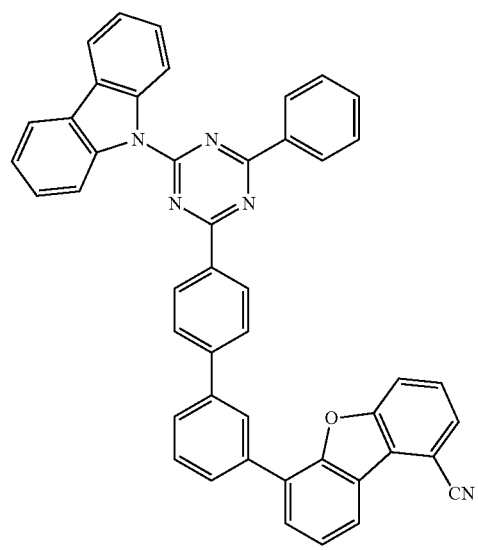

31
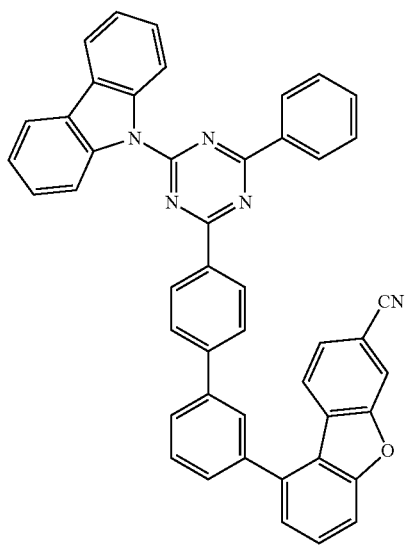
32
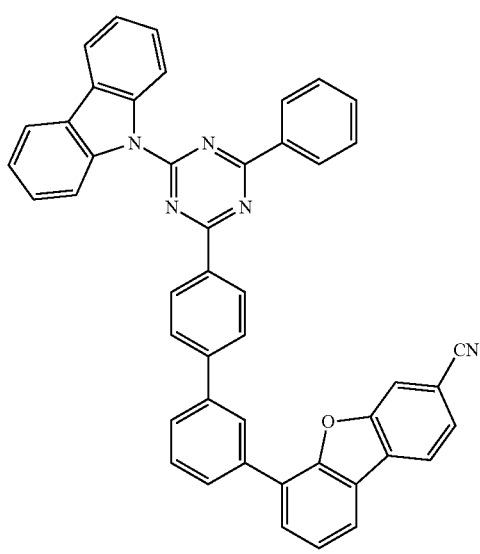
33
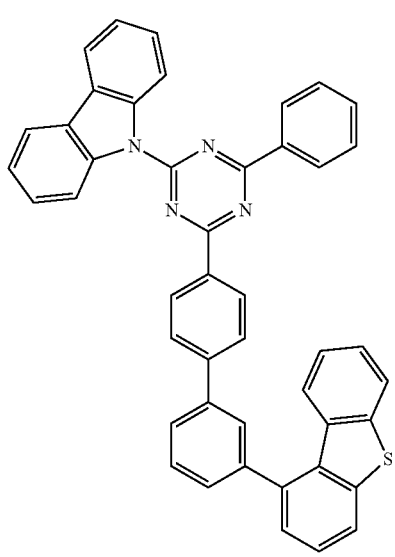
34
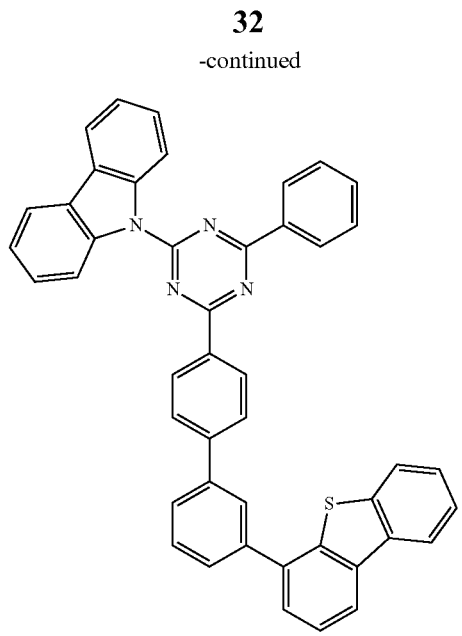
35
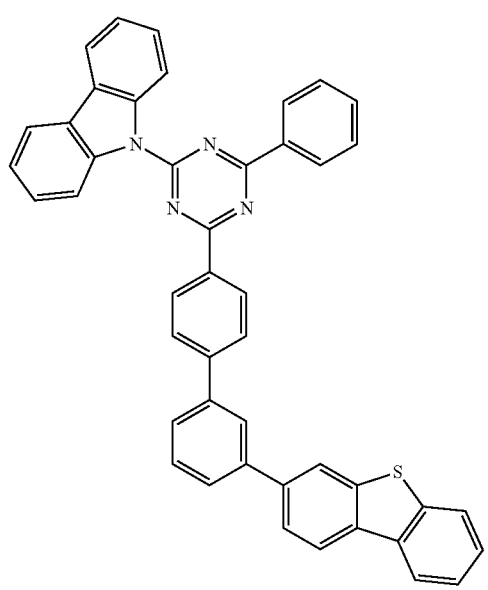
36
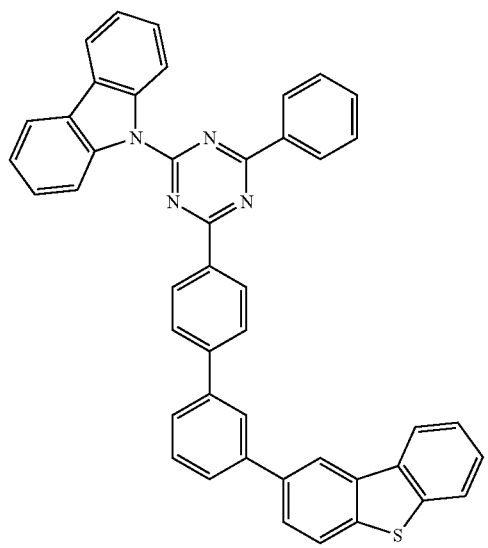

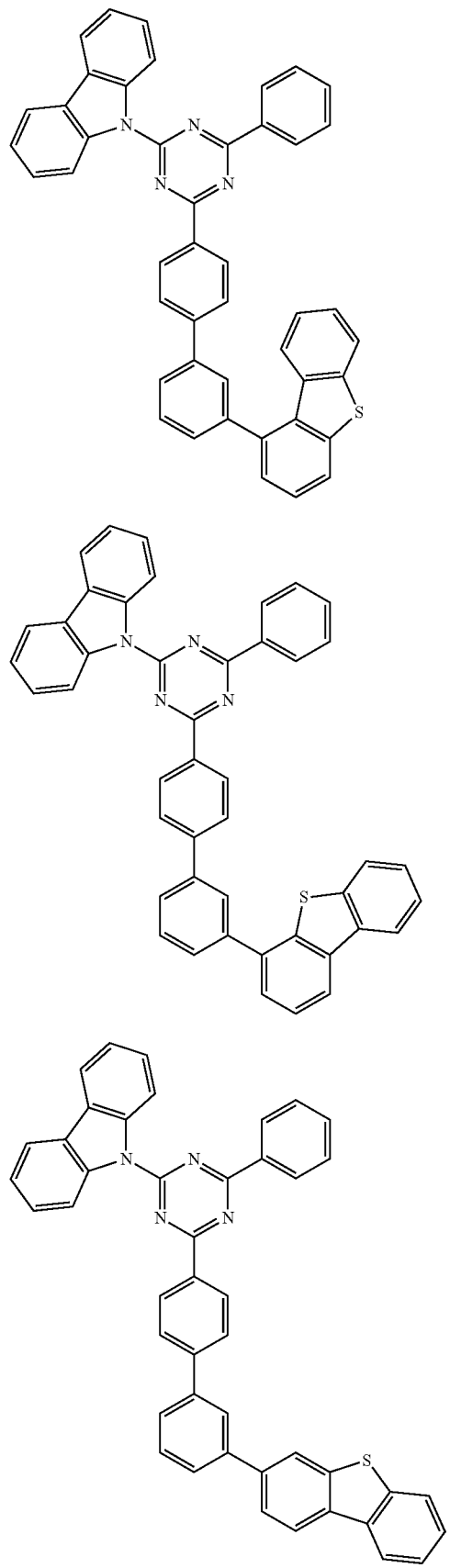
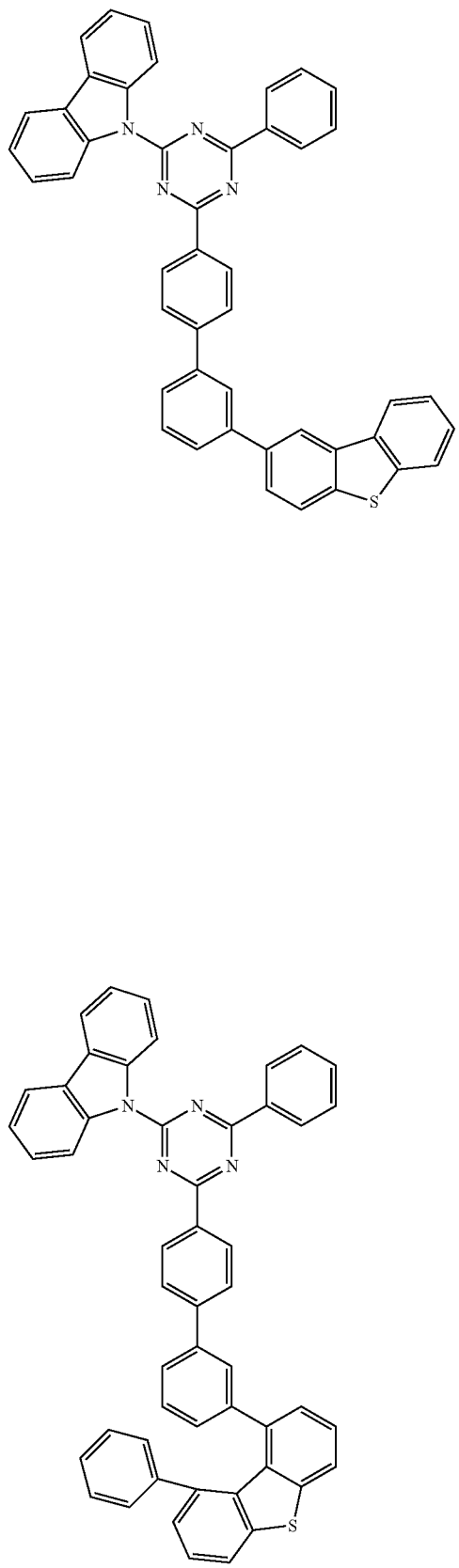

42
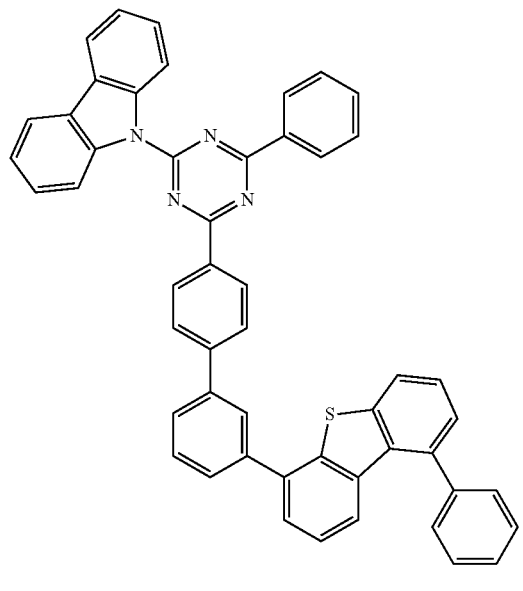
43
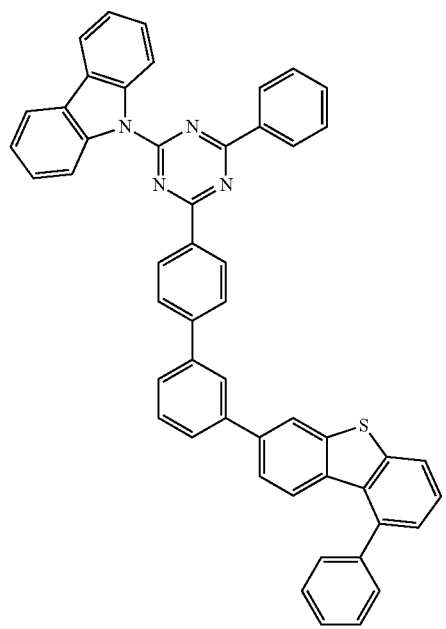
44
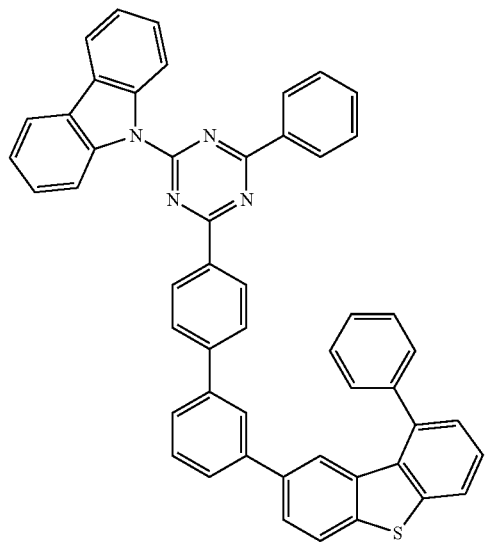
45
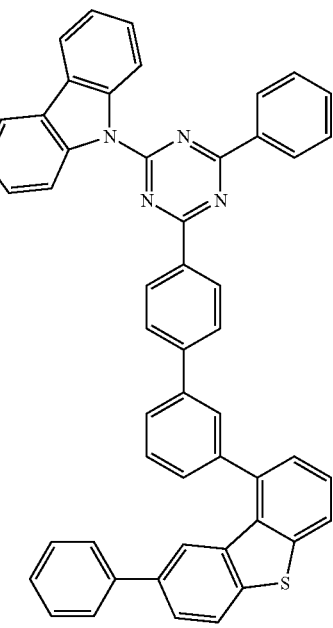

46
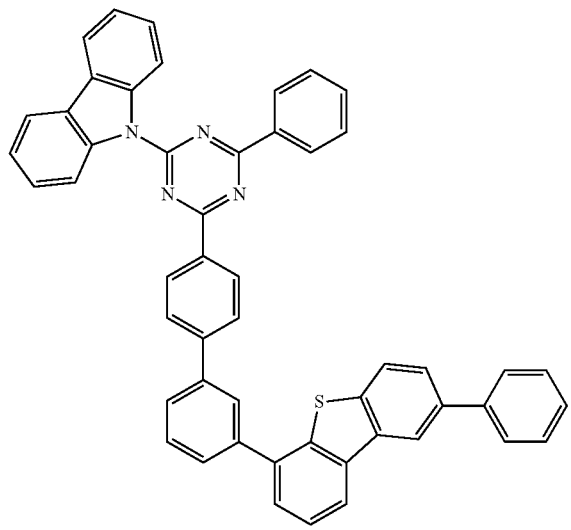
47
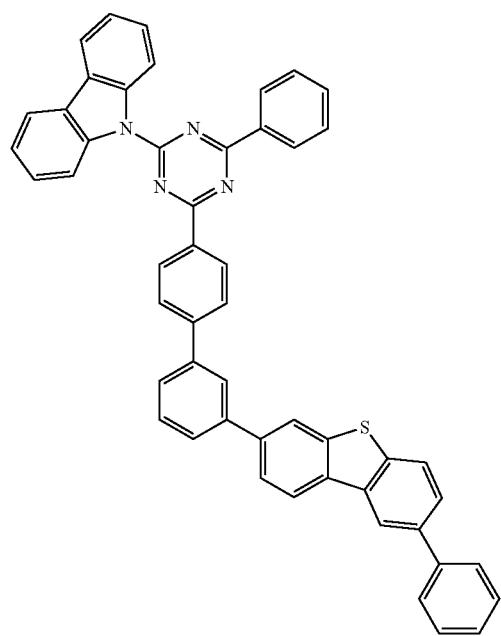
48
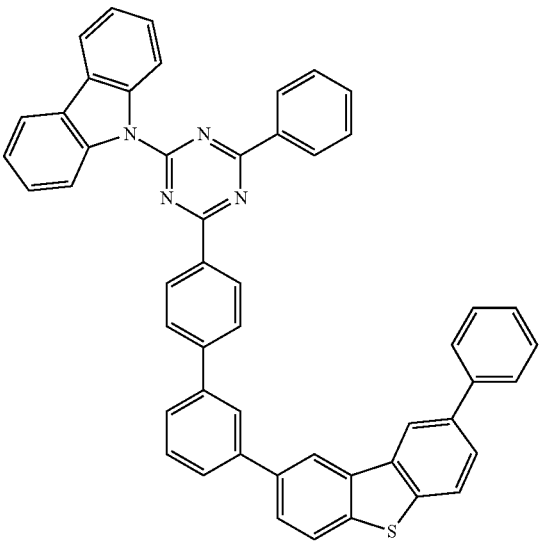
49
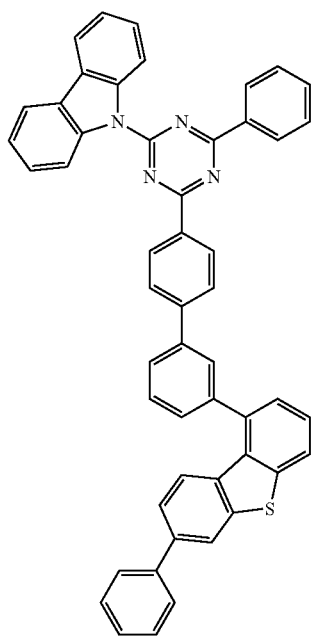

50
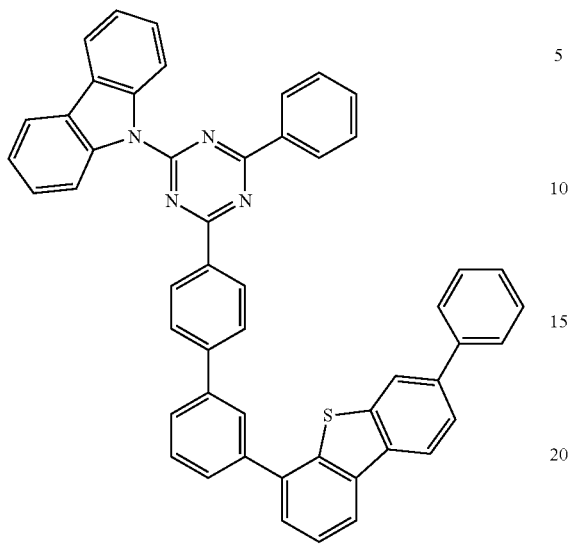
51
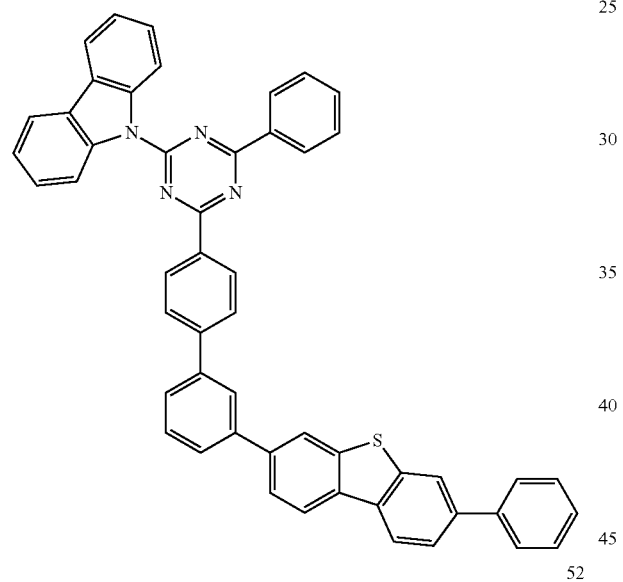
52
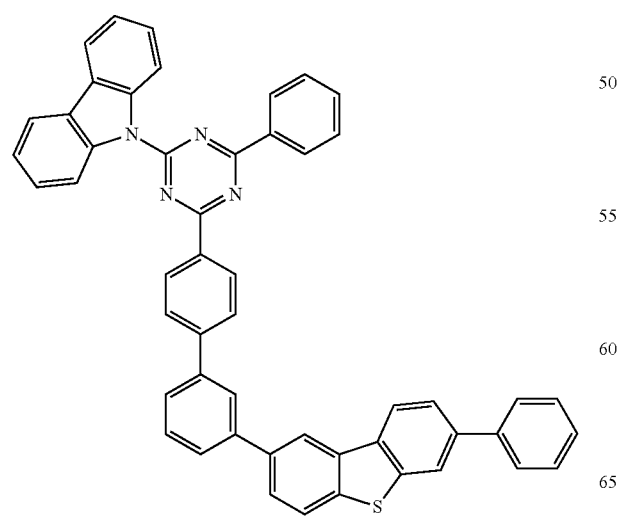
53
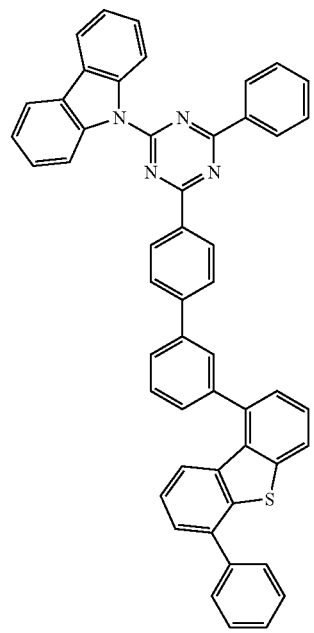
54
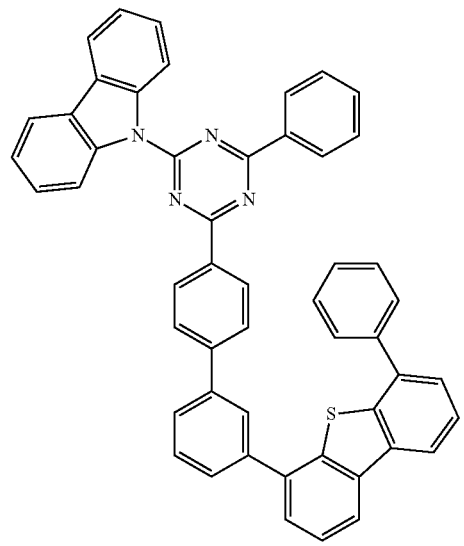

55
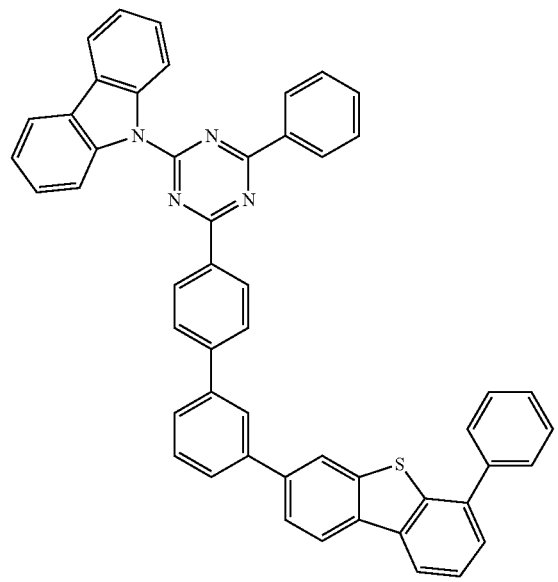
56
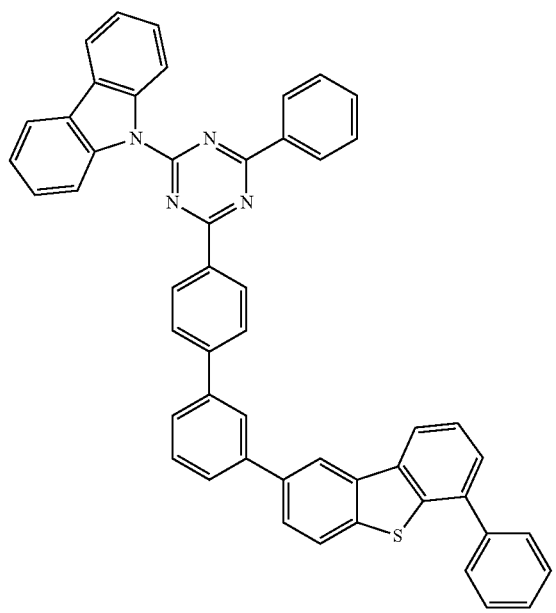
57
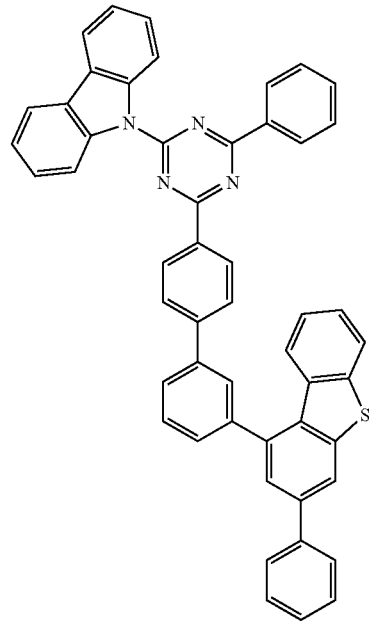
58
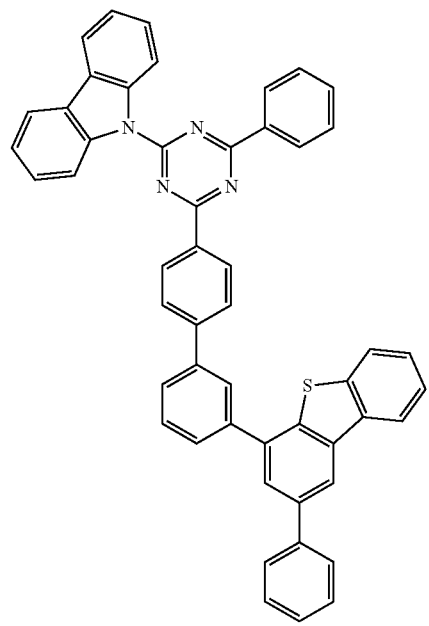

59
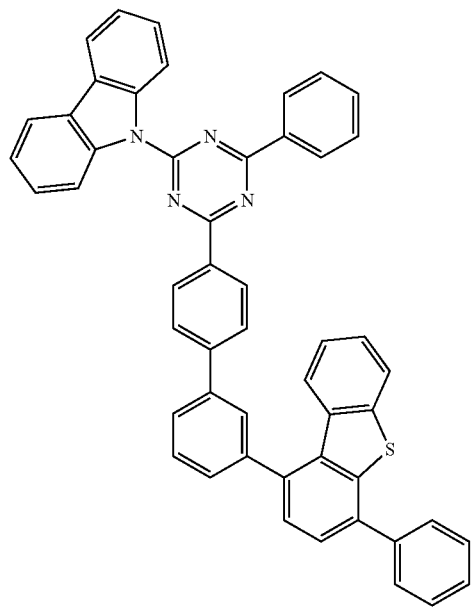
61
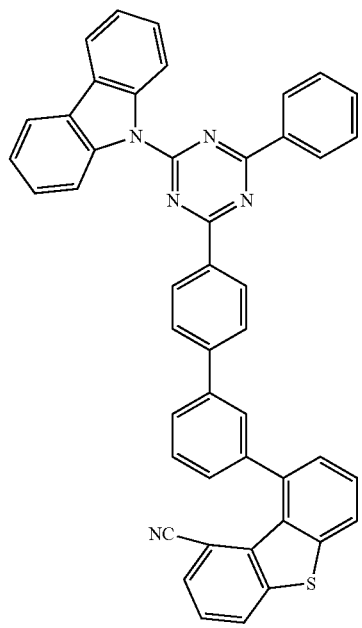
60
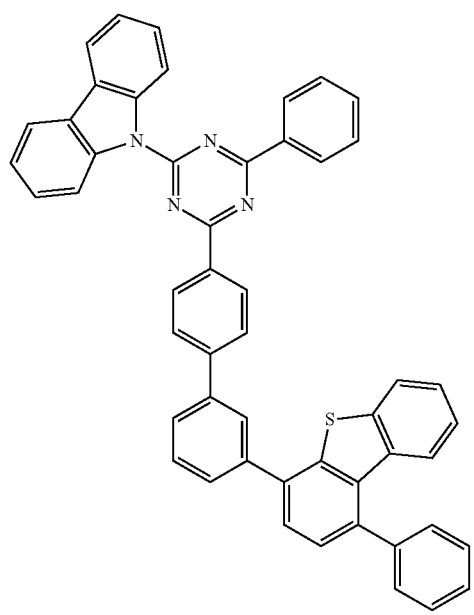
62
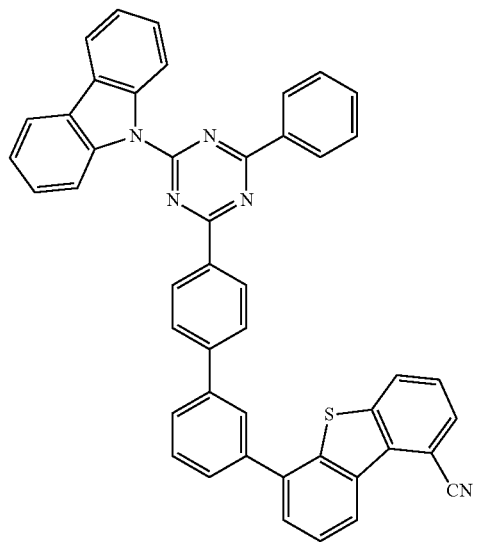

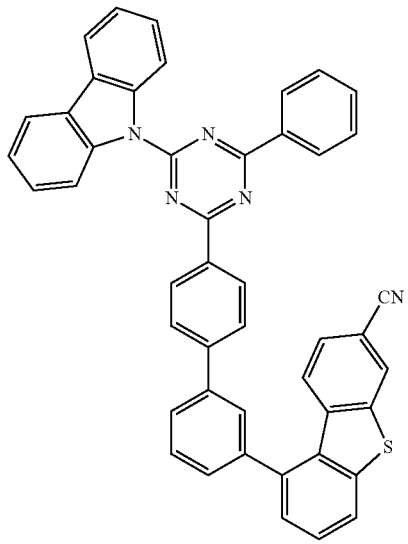

63

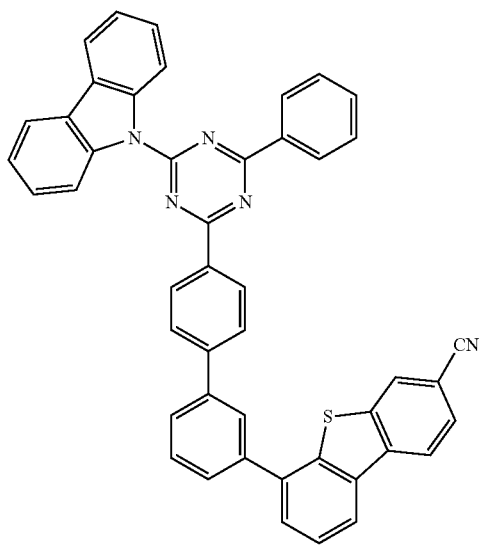

64

A composition according to an embodiment may include, e.g., the aforementioned compound for an organic optoelectronic device (represented by Chemical Formula 1) in a mixture with one or more additional compound.

In an implementation, the composition may include a mixture of, e.g., the compound represented by Chemical Formula 1 and a compound for an organic optoelectronic device represented by Chemical Formula 2.

[Chemical Formula 2]

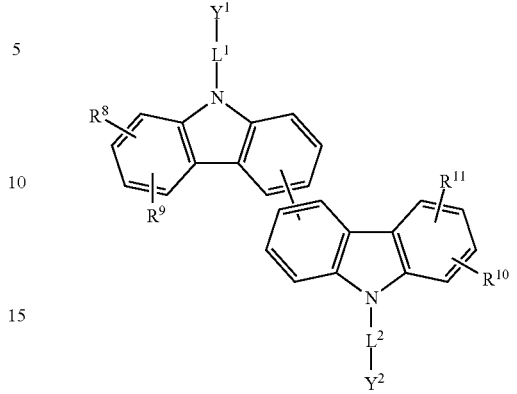

In Chemical Formula 2, $L^1$ and $L^2$ may each independently be or include, e.g., a single bond or a substituted or unsubstituted C6 to C30 arylene group, $Y^1$ and $Y^2$ may each independently be or include, e.g., a substituted or unsubstituted C6 to C30 aryl group, a substituted or unsubstituted C2 to C30 heterocyclic group, or a combination thereof, and $R^8$ to $R^{11}$ may each independently be or include, e.g., hydrogen, deuterium, a cyano group, a halogen, a substituted or unsubstituted C1 to C10 alkyl group, a substituted or unsubstituted C6 to C12 aryl group, or a combination thereof.

In an implementation, the compound for an organic optoelectronic device represented by Chemical Formula 1 may be included as a first host, and the compound for an organic optoelectronic device represented by Chemical Formula 2 may be included as a second host. In an implementation, the first host and the second host may be included as a composition (e.g., as a mixture).

In an implementation, the compound represented by Chemical Formula 2 may be represented by Chemical Formula 2A.

[Chemical Formula 2A]

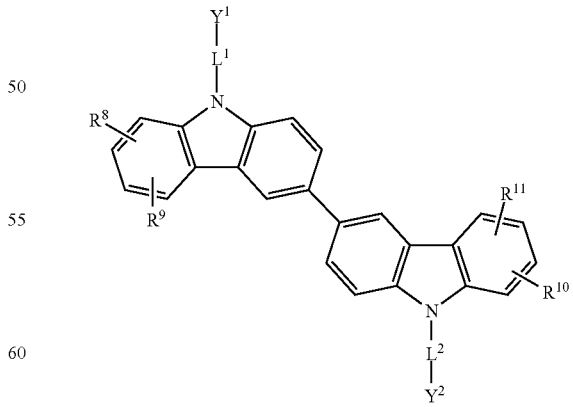

In Chemical Formula 2A, $L^1$, $L^2$, $Y^1$, $Y^2$, and $R^8$ to $R^{11}$ may be defined the same as those of Chemical Formula 2.

In an implementation, the aforementioned compound or composition (e.g., host) may further include a dopant.

The dopant may be, e.g., a phosphorescent dopant. In an implementation, the dopant may be, e.g., a red, green, or blue phosphorescent dopant. In an implementation, the dopant may be, e.g., a red or green phosphorescent dopant.

The dopant may be mixed with the compound or composition in a small amount to cause light emission, and may be, e.g., a metal complex that emits light by multiple excitation into a triplet or more. The dopant may be, e.g., an inorganic, organic, or organic/inorganic compound, and one or more types thereof may be used.

Examples of the dopant may include a phosphorescent dopant, and examples of the phosphorescent dopant may include organometallic compounds including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by the following Chemical Formula Z.

$$L^cMX^c$$ [Chemical Formula Z]

In Chemical Formula Z, M may be, e.g., a metal, and $L^c$ and $X^c$ may each independently be, e.g., a ligand to form a complex compound with M.

The M may be, e.g., Ir, Pt, Os, Ti, Zr, Hf, Eu, Tb, Tm, Fe, Co, Ni, Ru, Rh, Pd, or a combination thereof and the $L^c$ and $X^c$ may be, e.g., a bidendate ligand.

The aforementioned compound for an organic optoelectronic device may provide a film using a dry film-forming method such as chemical vapor deposition.

Hereinafter, an organic optoelectronic device including the aforementioned compound for an organic optoelectronic device is described.

The organic optoelectronic device may be a suitable device to convert electrical energy into photoenergy and vice versa, e.g., an organic photoelectric device, an organic light emitting diode, an organic solar cell, or an organic photoconductor drum.

Herein, an organic light emitting diode as one example of an organic optoelectronic device is described referring to drawings.

Figure 2:
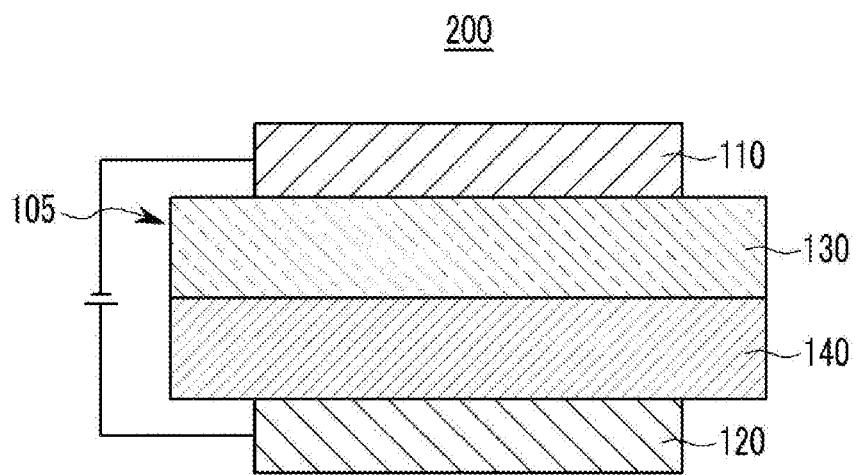

FIGS. 1 and 2 are cross-sectional views of each organic light emitting diode according to one embodiment.

Referring to FIG. 1, an organic light emitting diode 100 according to an embodiment may include an anode 120 and a cathode 110 facing each other and an organic layer 105 between the anode 120 and cathode 110.

The anode 120 may be made of a conductor having a large work function to help hole injection, and may be, e.g., a metal, a metal oxide and/or a conductive polymer. In an implementation, the anode 120 may be, e.g., a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline.

The cathode 110 may be made of a conductor having a small work function to help electron injection, and may be, e.g., a metal, a metal oxide and/or a conductive polymer. In an implementation, the cathode 110 may be, e.g., a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al, and $BaF_2$/Ca.

The organic layer 105 may include the aforementioned compound for an organic optoelectronic device or composition for an organic optoelectronic device.

The organic layer 105 may include a light emitting layer 130, and the light emitting layer 130 may include the aforementioned compound for an organic optoelectronic device or composition for an organic optoelectronic device.

The composition for an organic optoelectronic device further including the dopant may be, e.g., a green light emitting composition.

The light emitting layer 130 may include, e.g., the aforementioned first compound for an organic optoelectronic device and second compound for an organic optoelectronic device as phosphorescent hosts, respectively.

The organic layer may further include an auxiliary layer in addition to the light emitting layer.

The auxiliary layer may be, e.g., a hole auxiliary layer 140.

Referring to FIG. 2, an organic light emitting diode 200 may further include a hole auxiliary layer 140 as well as the light emitting layer 130. The hole auxiliary layer 140 may further increase hole injection and/or hole mobility between the anode 120 and the light emitting layer 130 and block electrons.

The hole auxiliary layer 140 may include, e.g., a compound of the following Group A.

In an implementation, the hole auxiliary layer 140 may include a hole transport layer between the anode 120 and the light emitting layer 130, and a hole transport auxiliary layer between the light emitting layer 130 and the hole transport layer, and at least one compound of Group A may be included in the hole transport auxiliary layer.

[Group A]

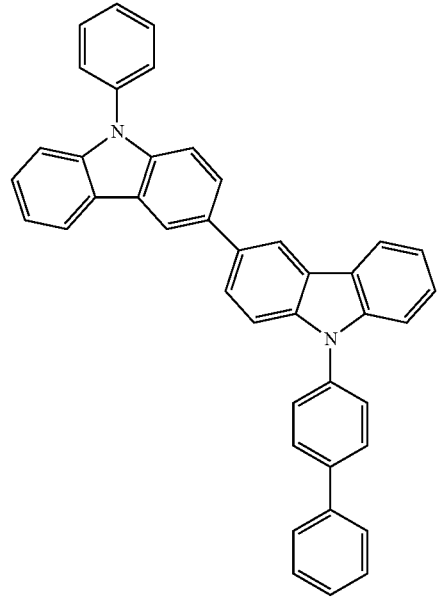

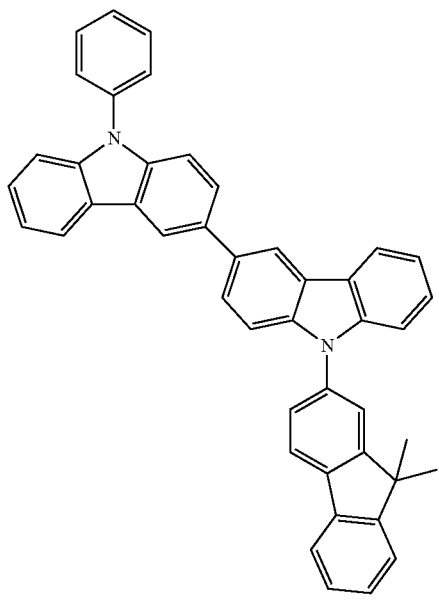
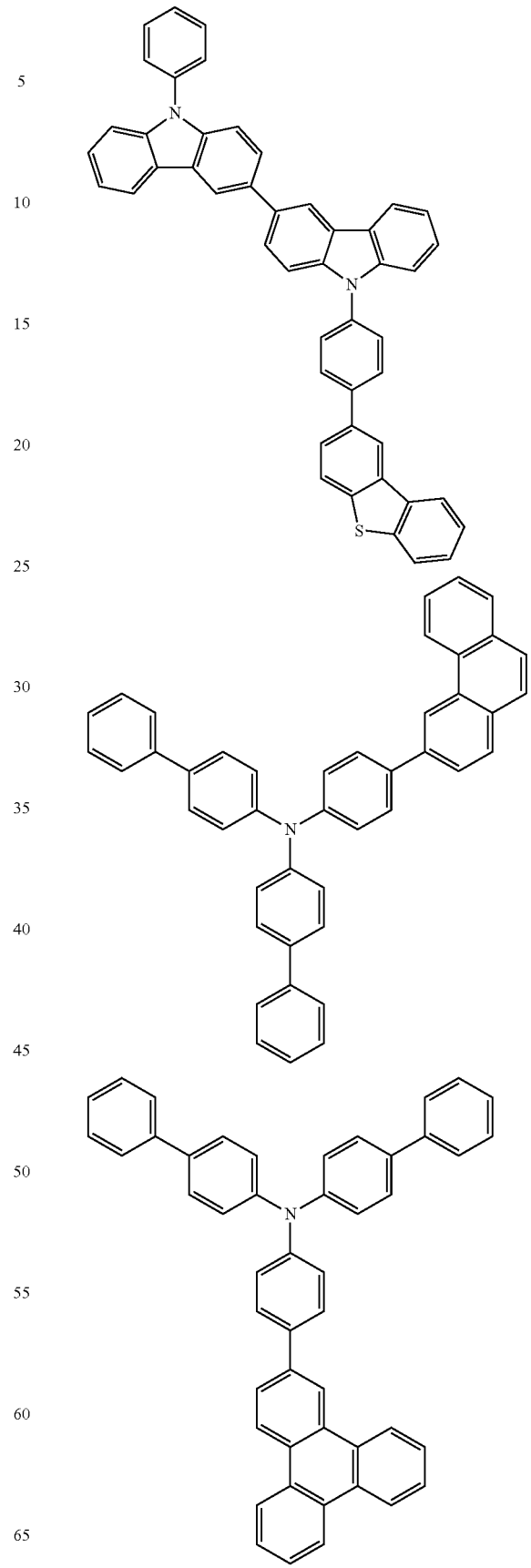

51
-continued
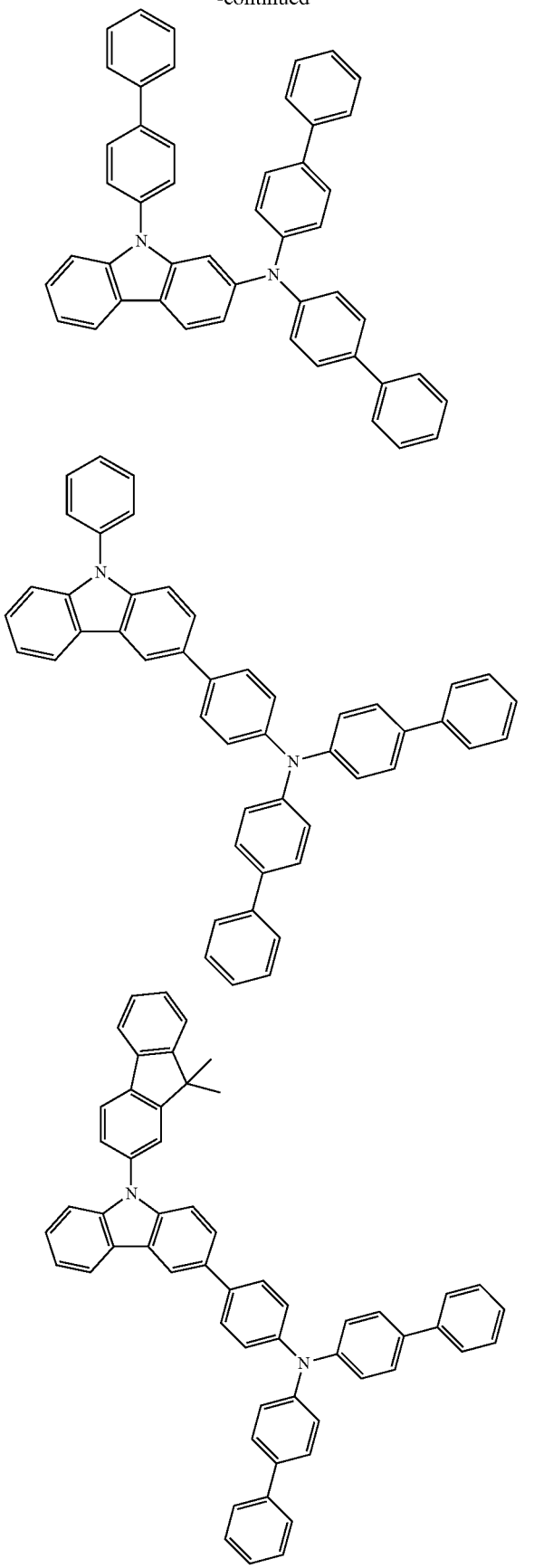
52
-continued
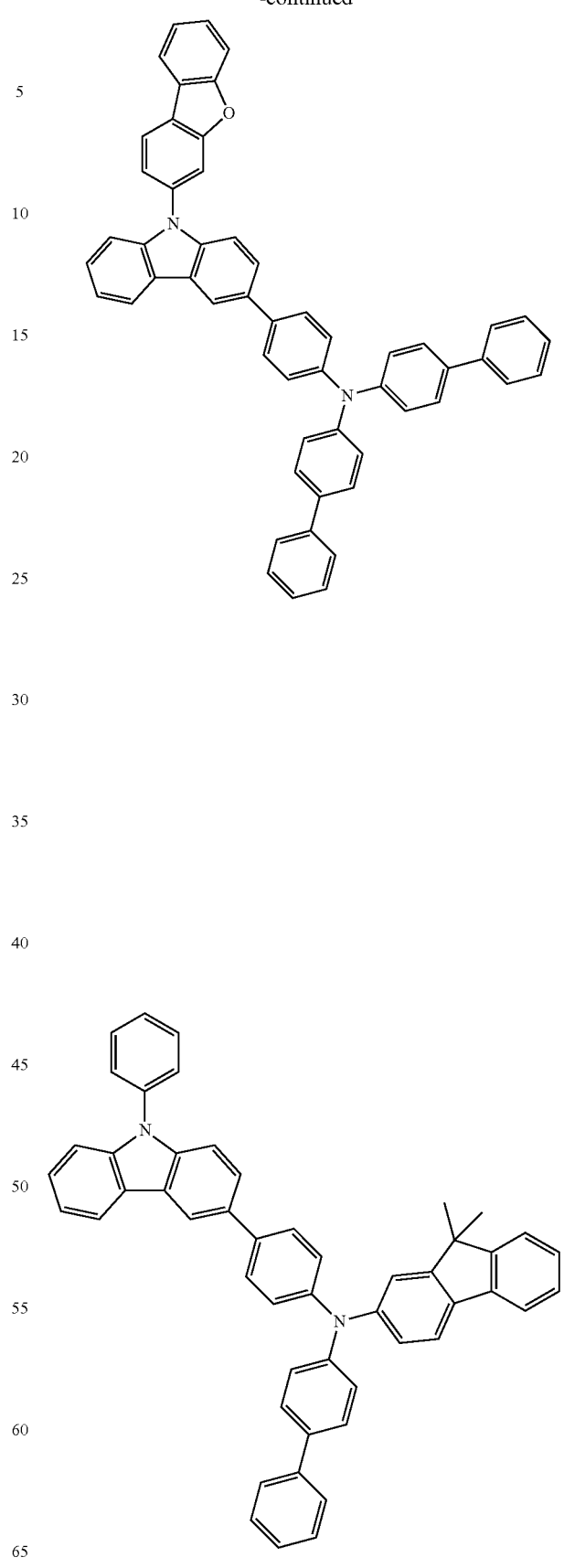

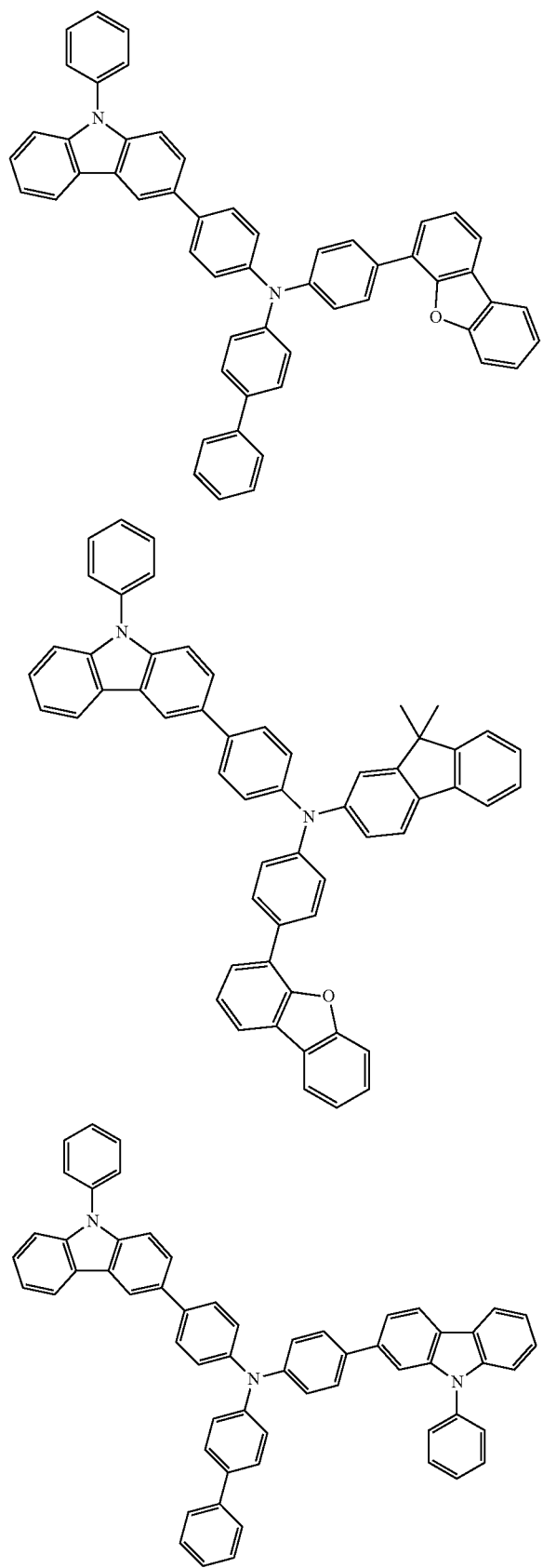
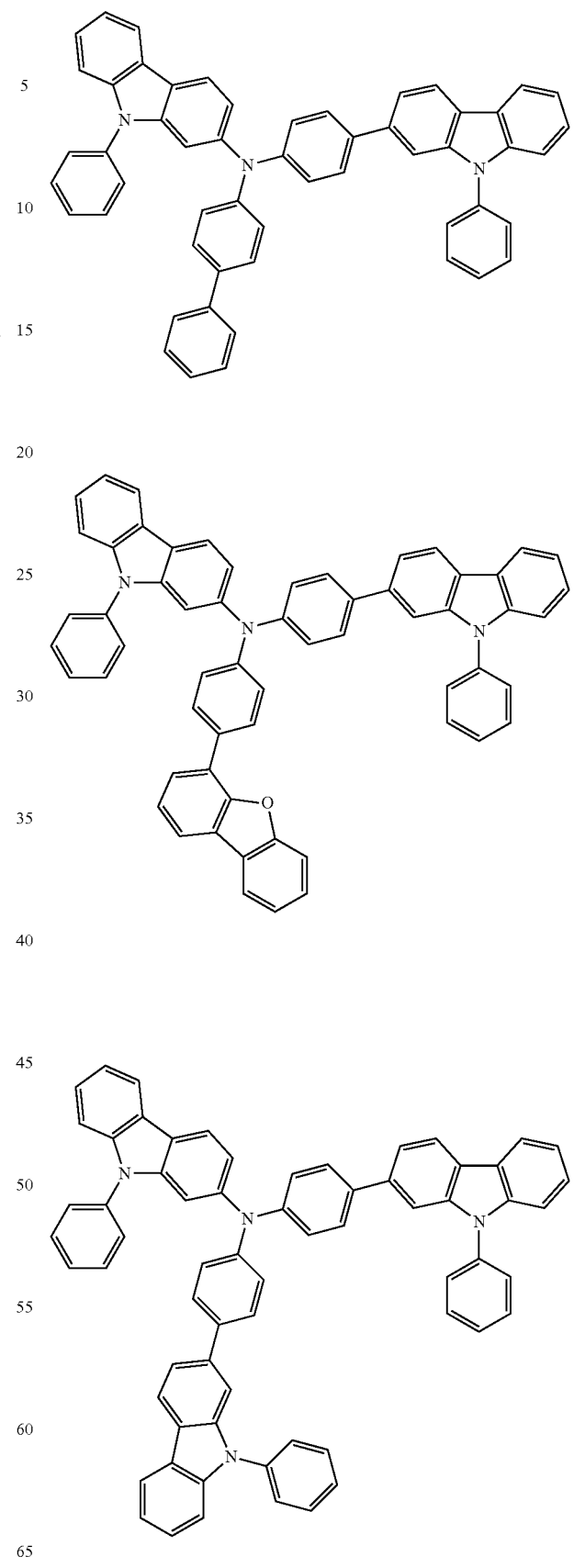

55
-continued
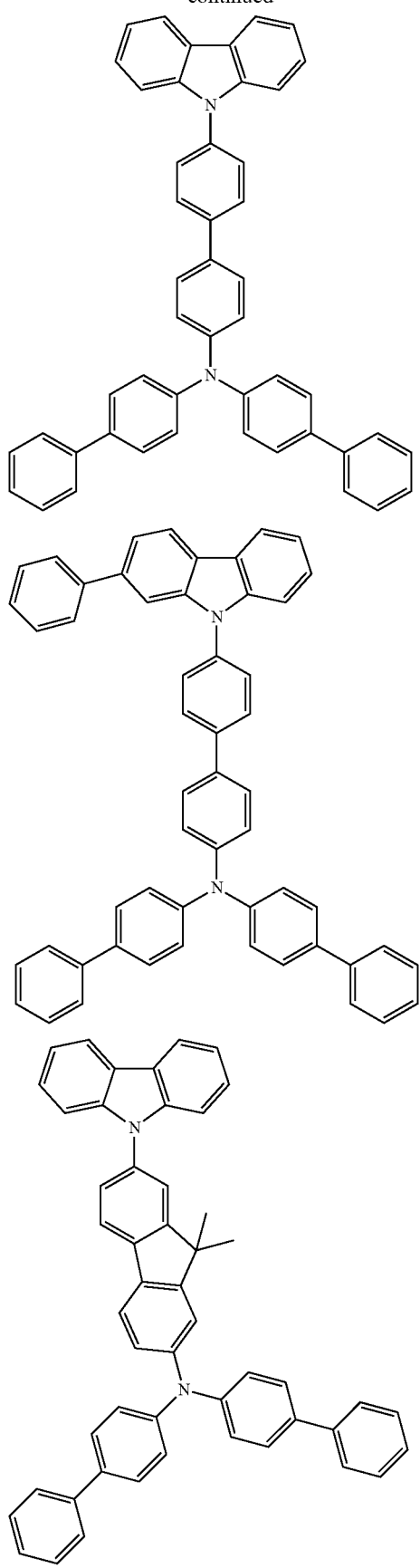
56
-continued
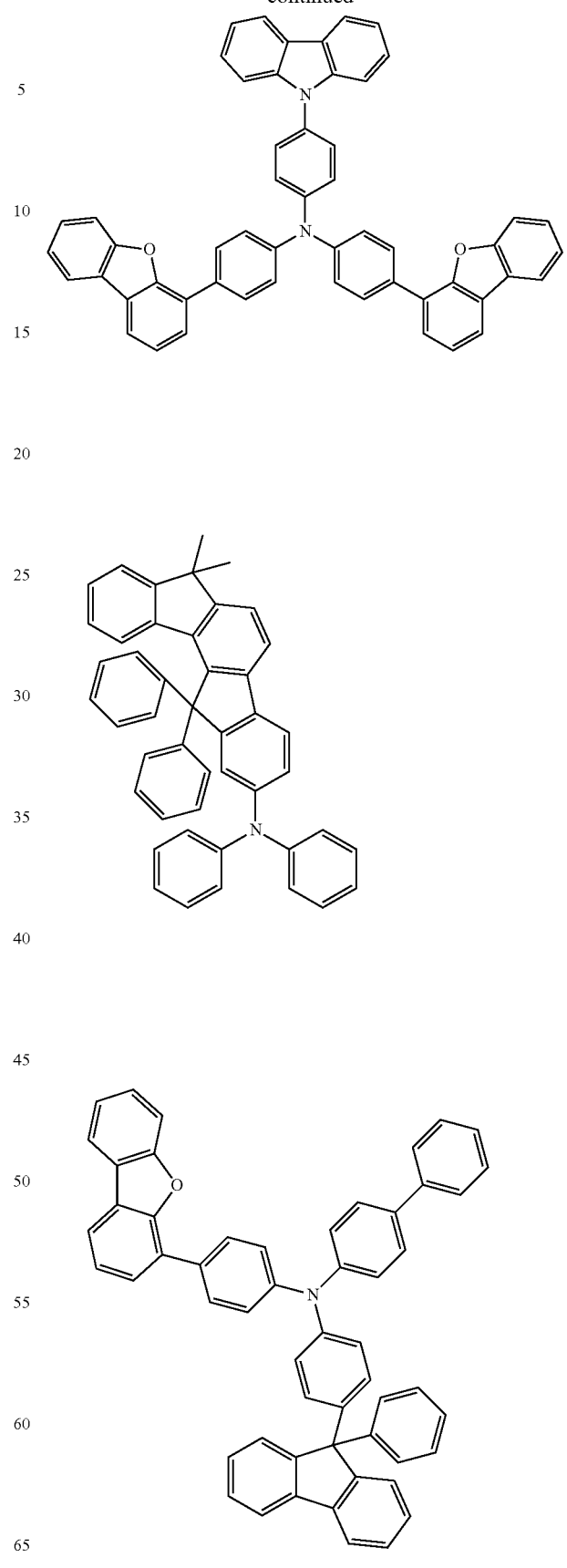

57
-continued
58
-continued
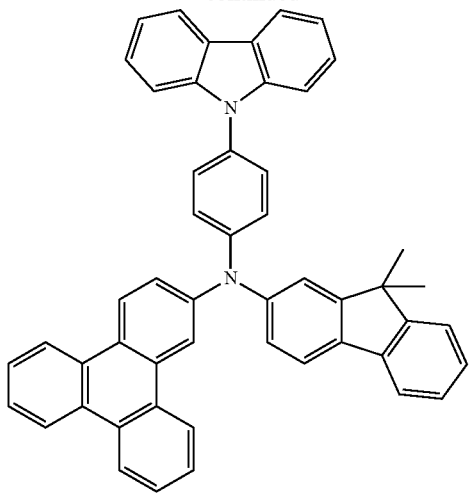
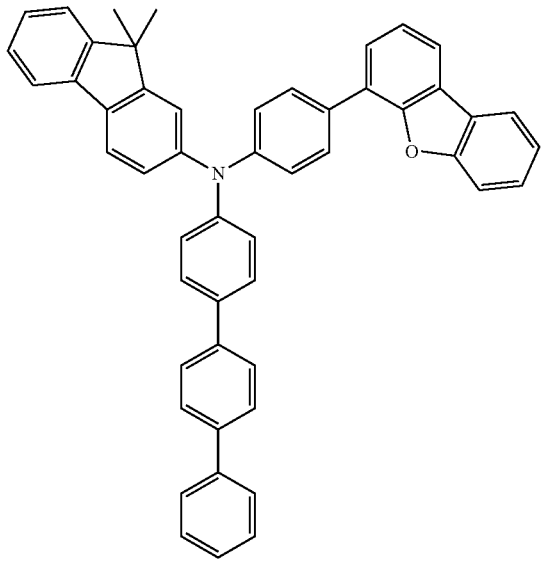
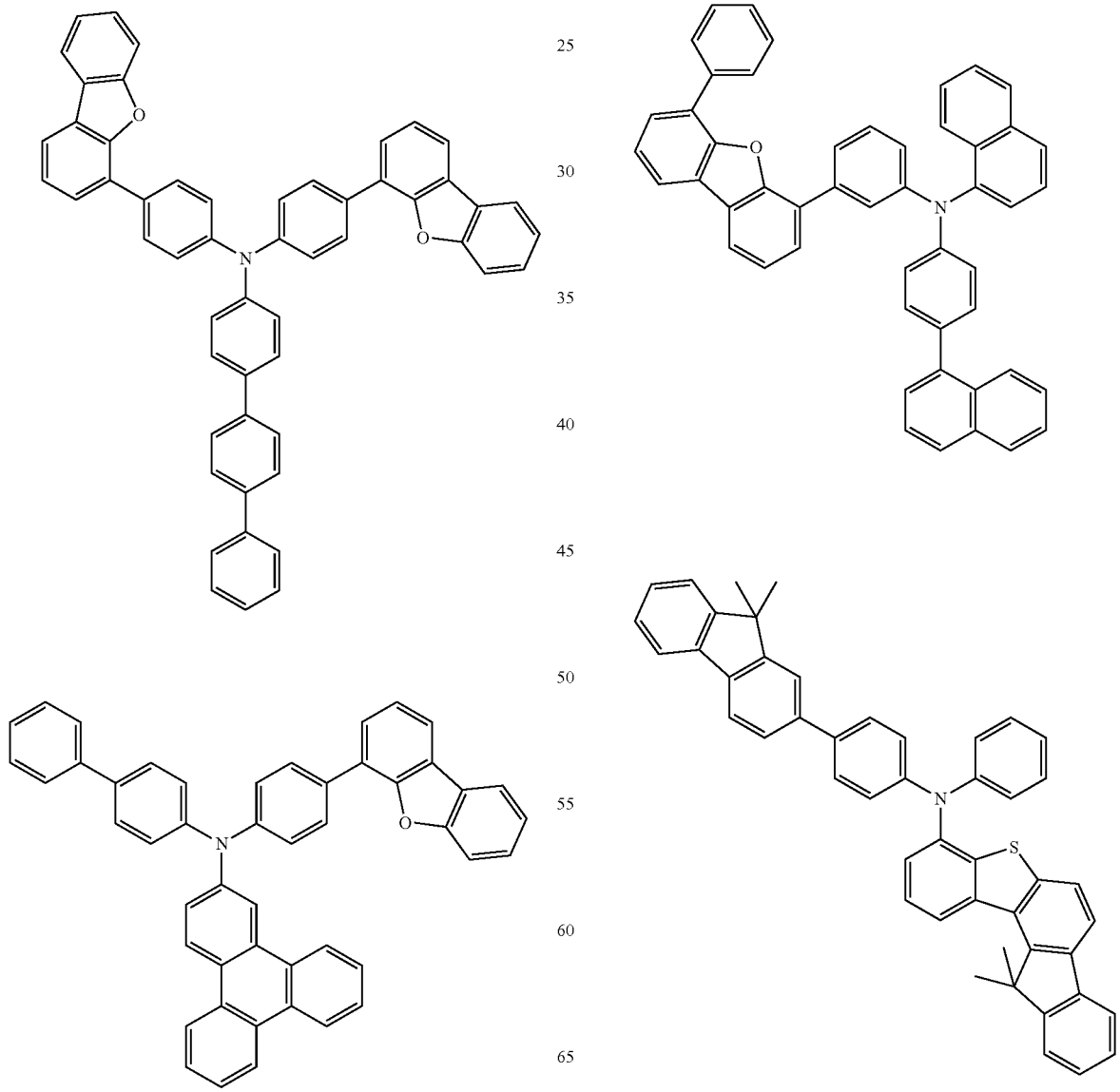

59
-continued
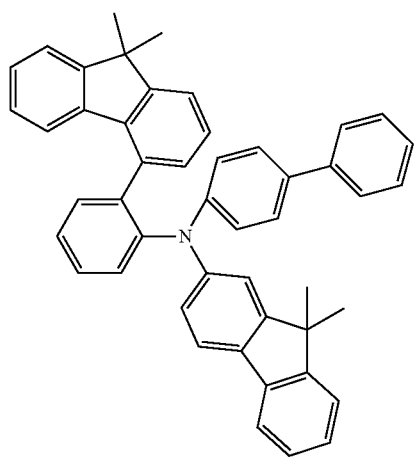
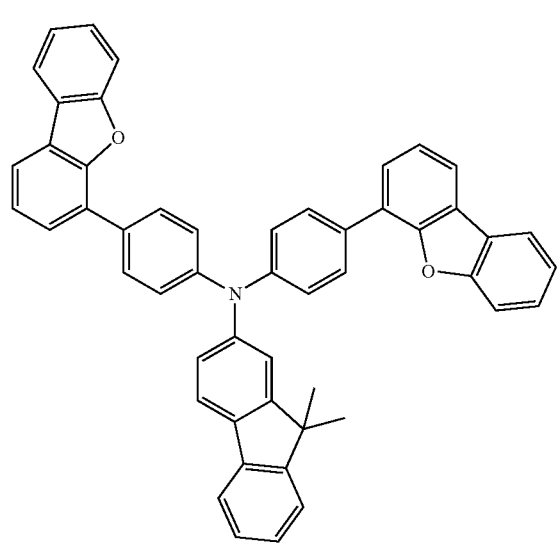
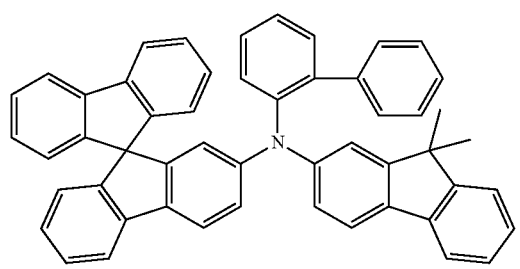
60
-continued
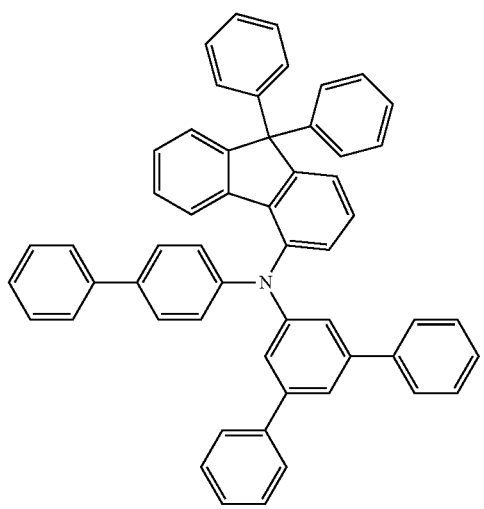
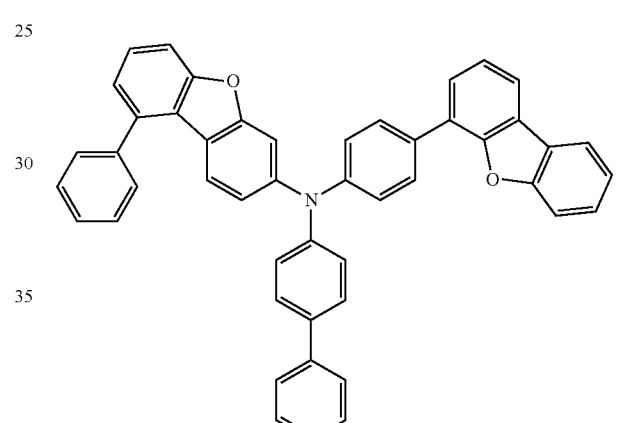
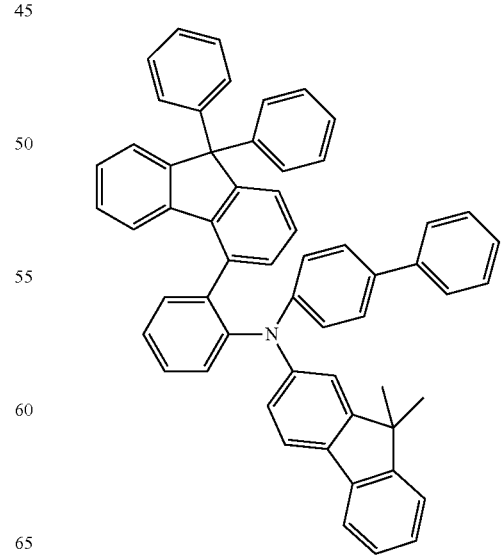

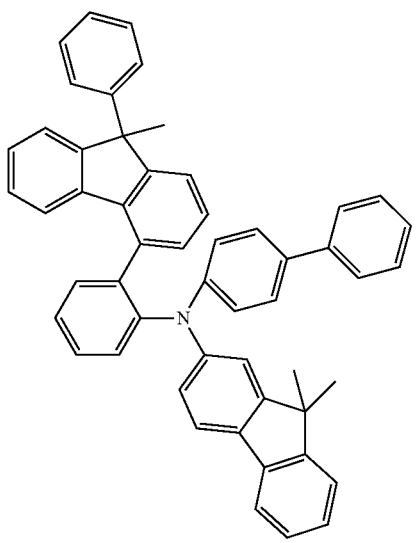
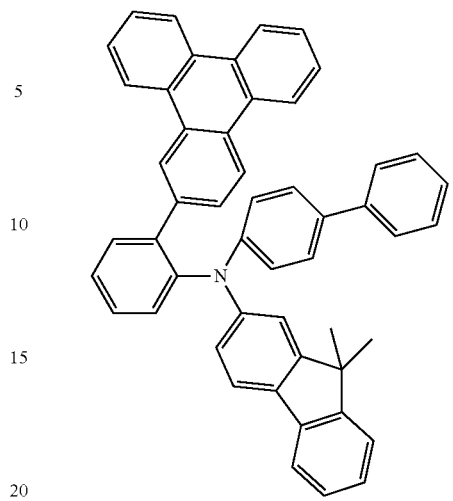
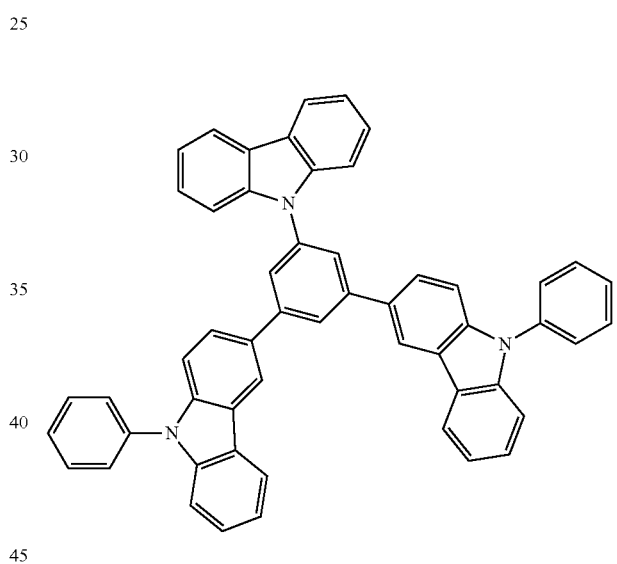
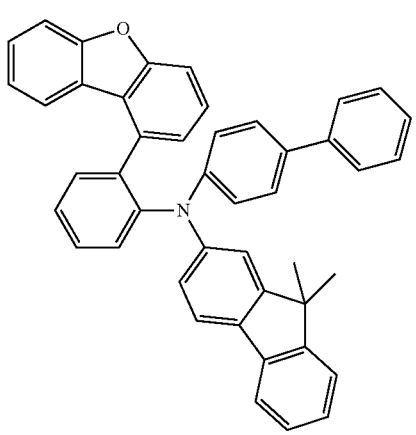
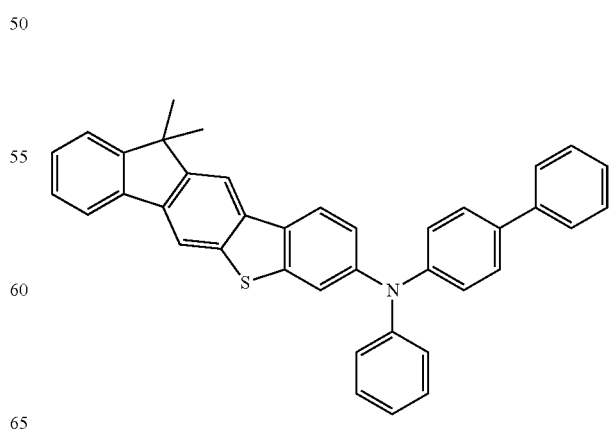

63
-continued
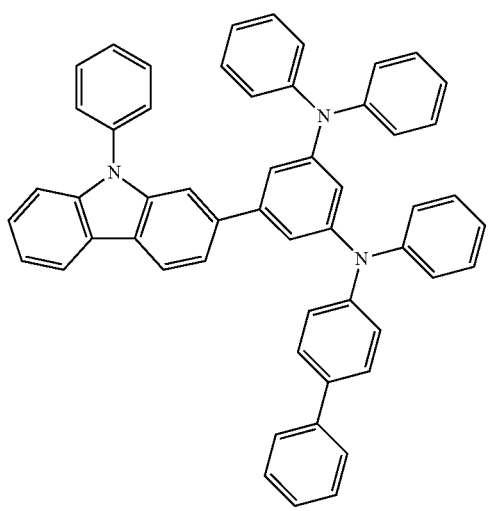
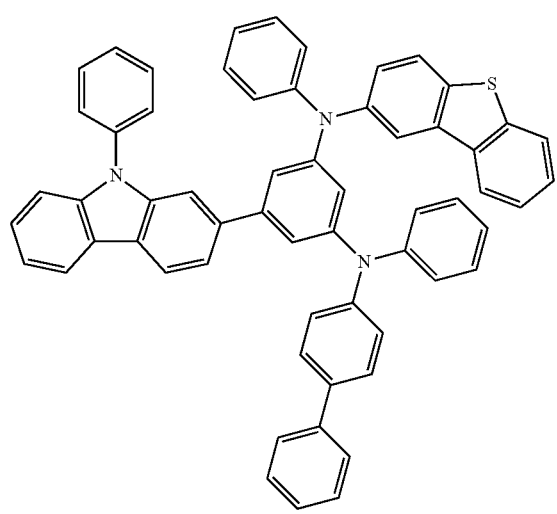
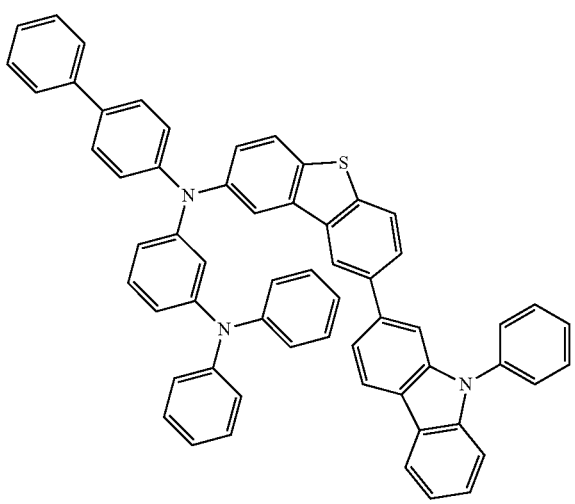
64
-continued
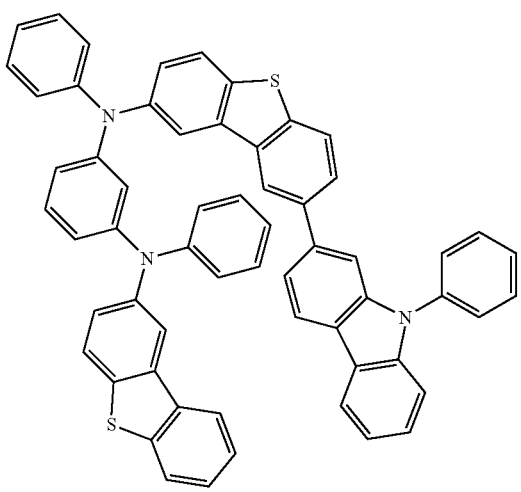
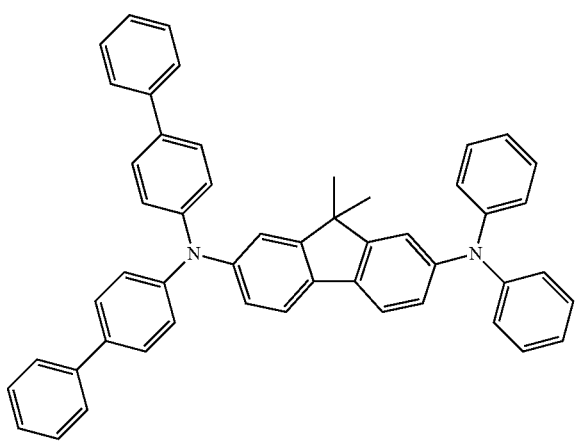

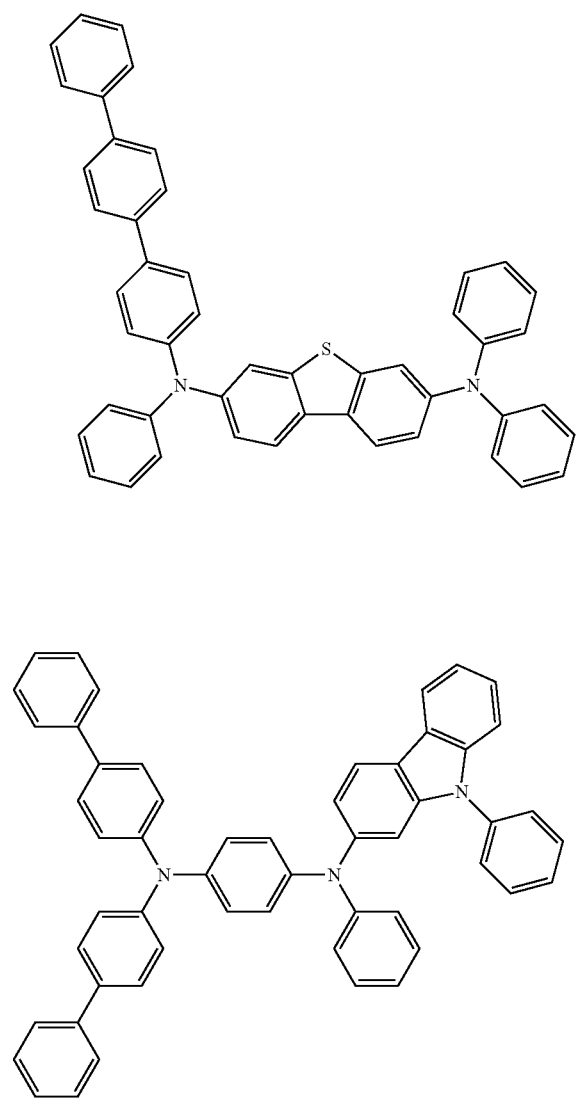
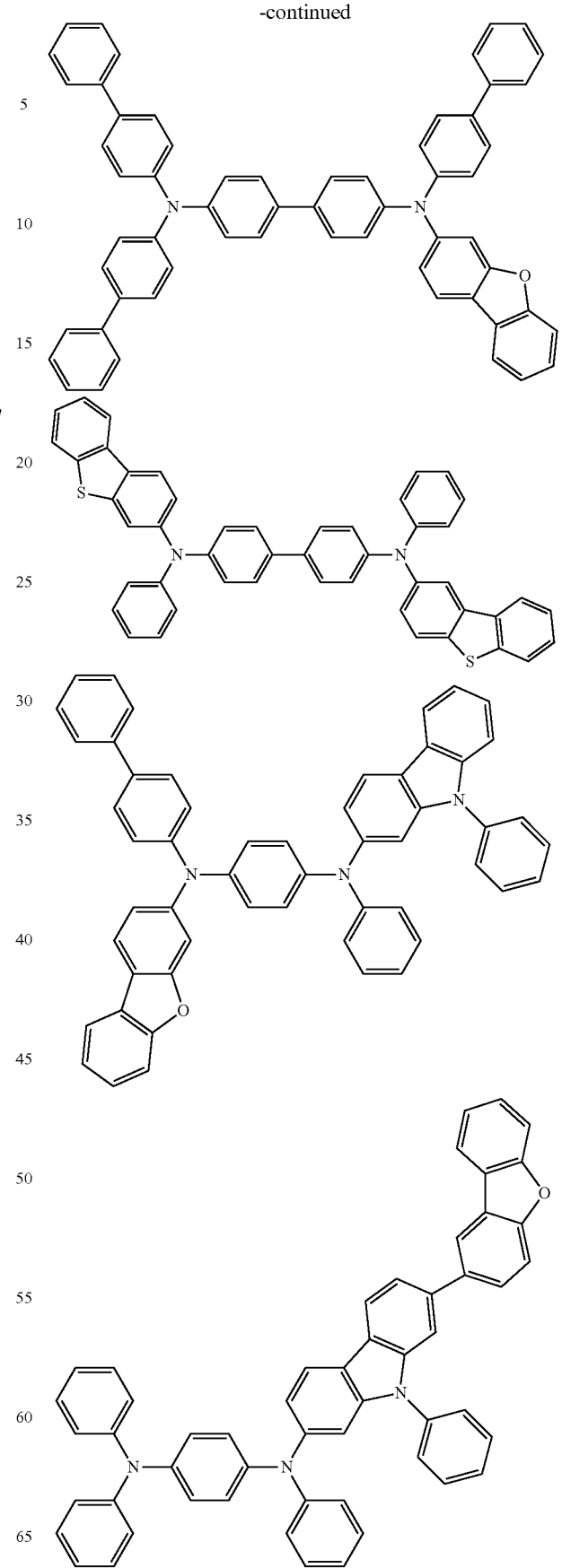

-continued
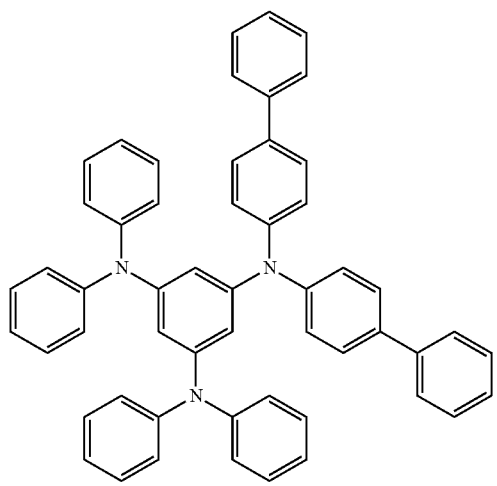
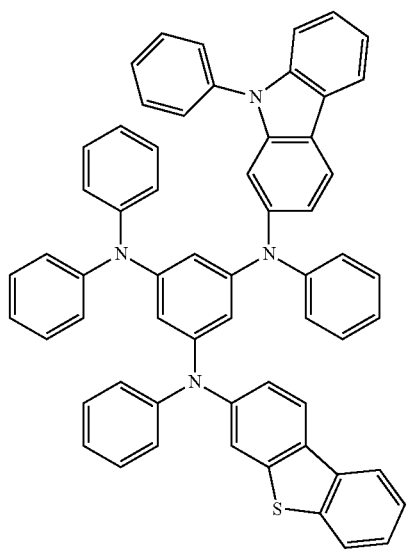
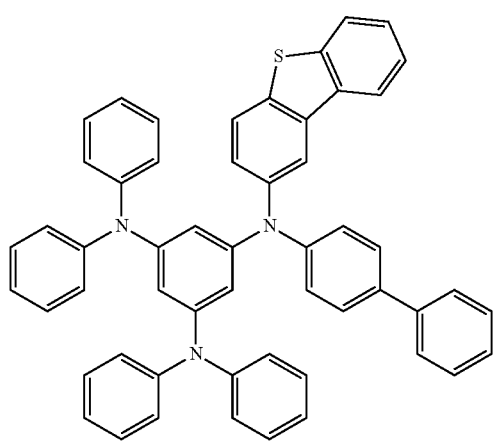
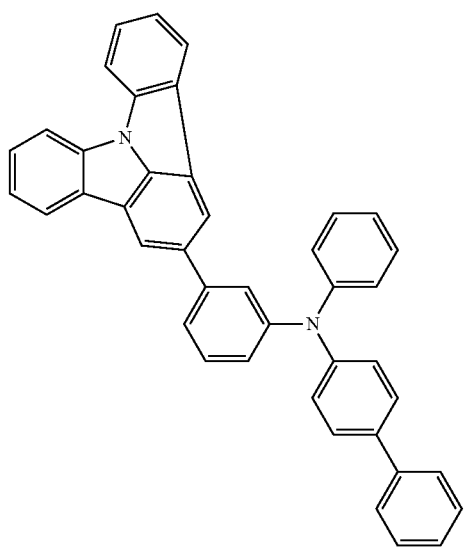
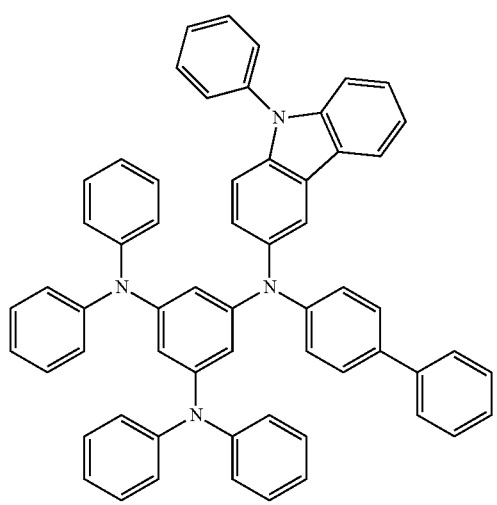
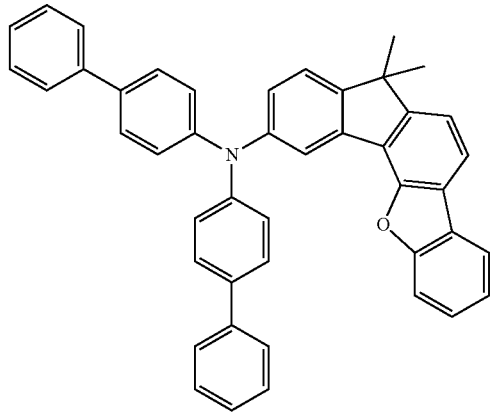

69
-continued
70
-continued
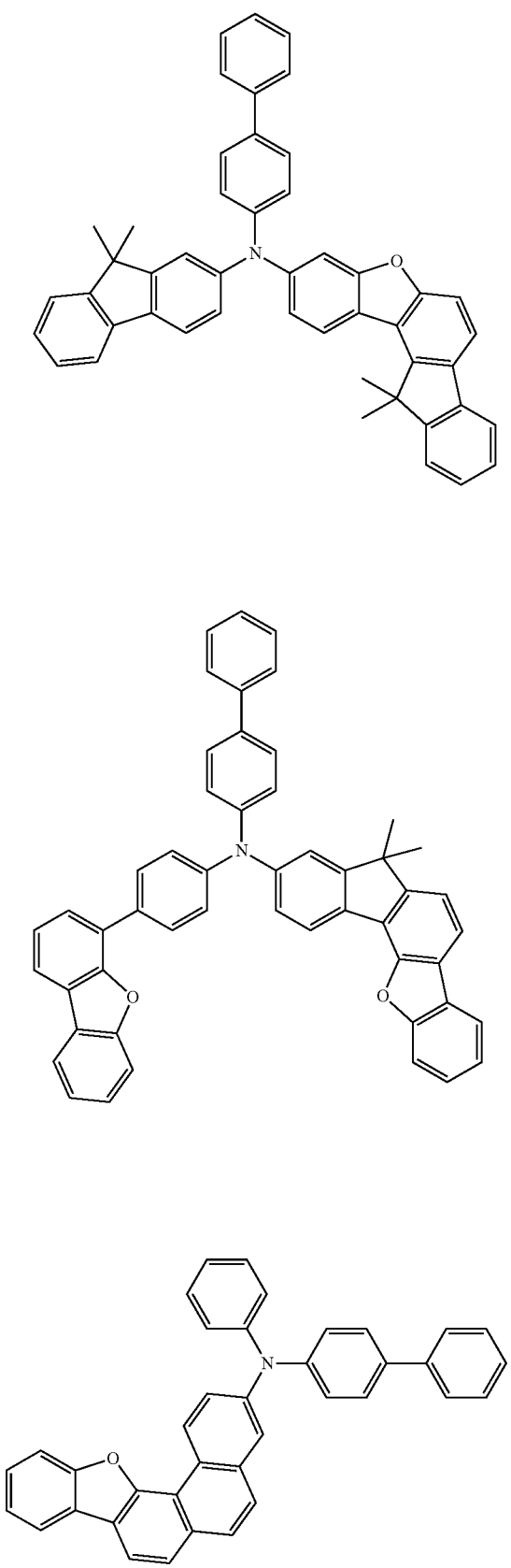
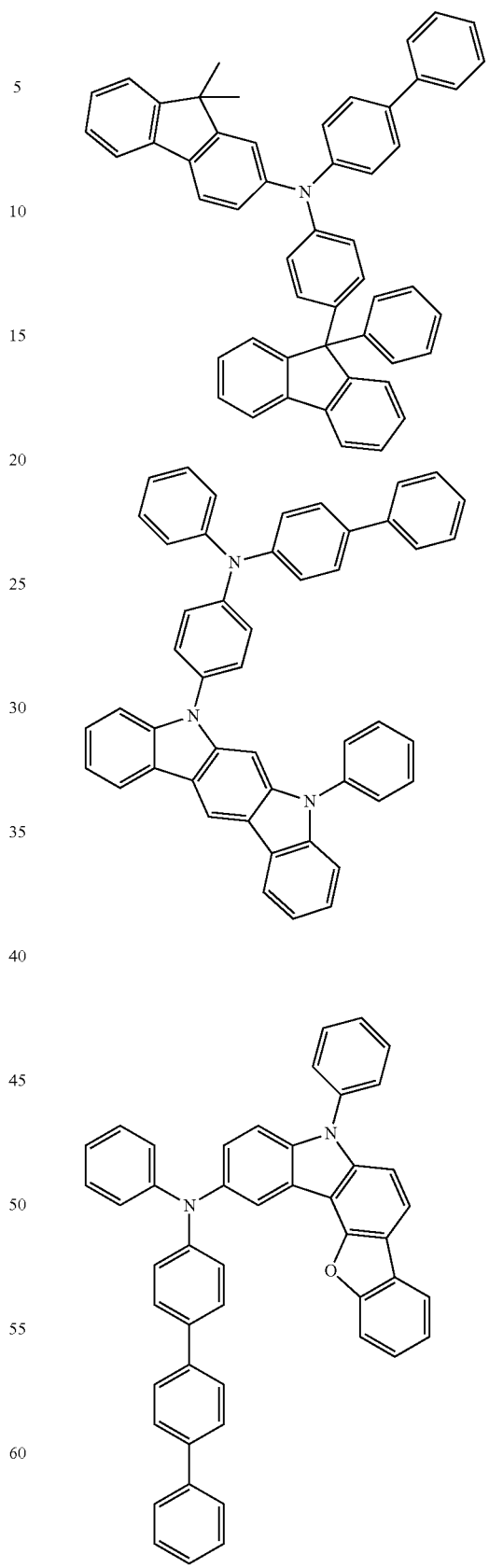

-continued

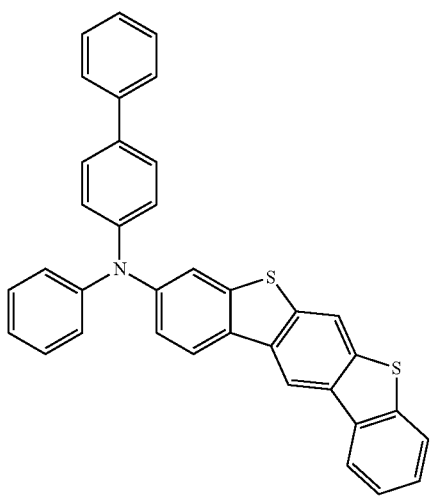
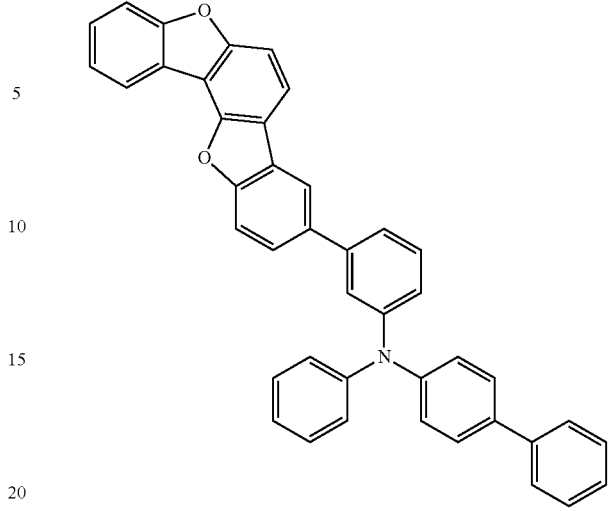
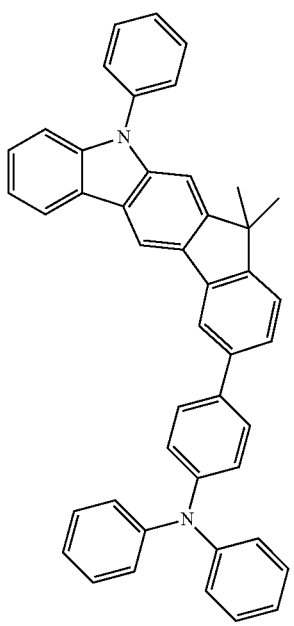
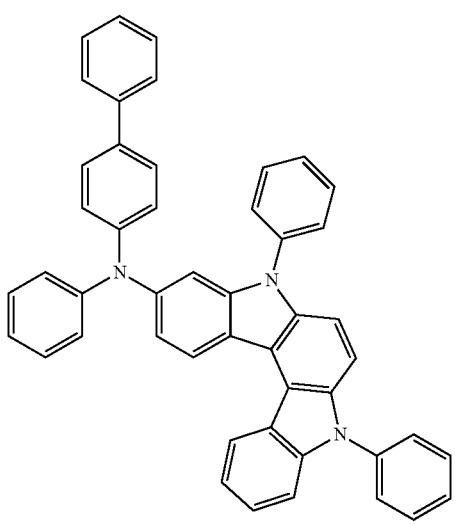

In the hole transport auxiliary layer, compounds disclosed in U.S. Pat. No. 5,061,569A, JP1993-009471A, WO1995-009147A1, JP1995-126615A, JP1998-095973A, and the like and compounds similar thereto may be used in addition to the aforementioned compounds.

In an implementation, in FIG. 1 or 2, an organic light emitting diode may further include an electron transport layer, an electron injection layer, or a hole injection layer as the organic layer 105.

The organic light emitting diodes 100 and 200 may be produced by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in Examples and Synthesis Examples were purchased from Sigma-Aldrich Co. Ltd., TCI Inc., Tokyo chemical industry or P&H tech as far as there in no particular comment or were synthesized by suitable methods.

(Preparation of Compound for Organic Optoelectronic Device)

The compound was synthesized through the following steps.

Preparation of First Compound for Organic Optoelectronic Device

Synthesis Example 1: Synthesis of Intermediate I-1

[Reaction Scheme 1]

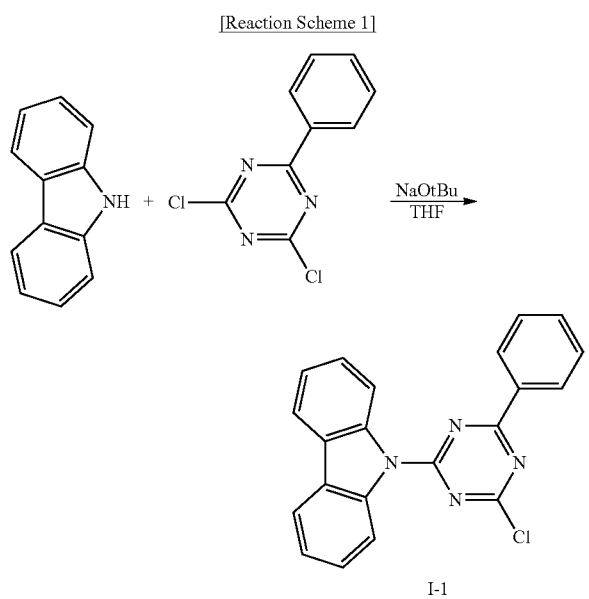

9H-carbazole (70 g, 419 mmol) purchased from Tokyo Chemical Industry Co., Ltd. (http://www.tcichemicals.com/) and 2,4-dichloro-6-phenyl-1,3,5-triazine (142 g, 628 mmol) were dissolved in 1 L of tetrahydrofuran (THF) under a nitrogen atmosphere, and sodium tert-butoxide (44.3 g, 461 mmol) was slowly added thereto and stirred therewith at 0° C. After 12 hours, water was added to the reaction solution, and the mixture was filtered. This obtained residue was separated and purified through flash column chromatography to obtain Intermediate I-1 (142 g, 95%).

HRMS (70 eV, EI+): m/z calcd for C21H13ClN: 356.0829, found: 356.

Elemental Analysis: C, 71%; H, 4%

Synthesis Example 2: Synthesis of Intermediate I-2

[Reaction Scheme 2]

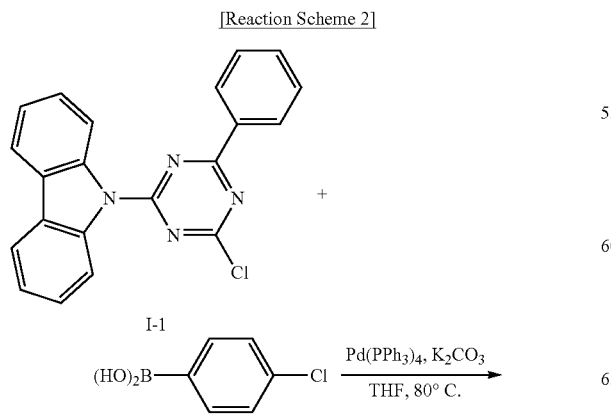

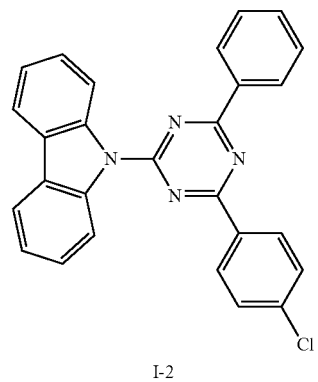

Intermediate I-1 (130 g, 364 mmol) was dissolved in 1.0 L of tetrahydrofuran (THF) under a nitrogen atmosphere, and 4-chlorophenylboronic acid (68.4 g, 437 mmol) purchased from Tokyo Chemical Industry Co., Ltd., and tetrakis (triphenylphosphine) palladium (8.41 g, 7.28 mmol) were added thereto and stirred therewith. Potassium carbonate (126 g, 910 mmol) saturated in water was added thereto and then, heated and refluxed at 80° C. for 12 hours. When a reaction was complete, water was added to the reaction solution, and the mixture was extracted with dichloromethane (DCM), treated with anhydrous magnesium sulfate to remove moisture, and filtered under a reduced pressure. This obtained residue was separated and purified through flash column chromatography to obtain Intermediate I-2 (147 g, 93%).

HRMS (70 eV, EI+): m/z calcd for C27H17ClN4: 432.1142, found: 432.

Elemental Analysis: C, 75%; H, 4%

Synthesis Example 3: Synthesis of Intermediate I-3

[Reaction Scheme 3]

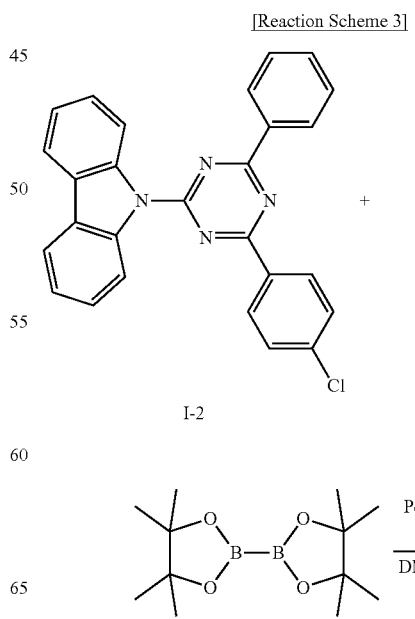

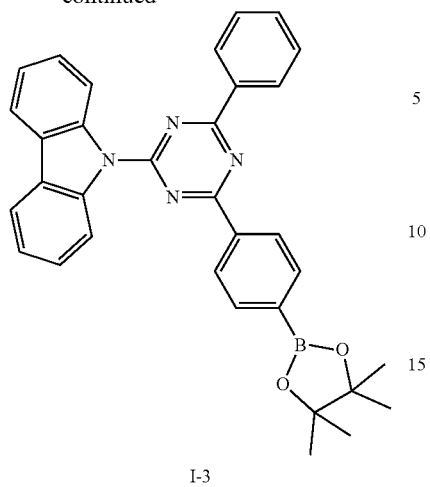

I-3

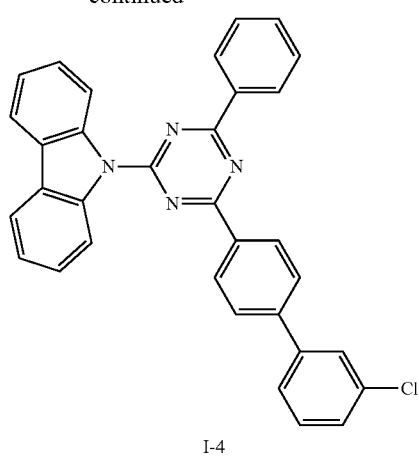

I-4

Intermediate I-2 (130 g, 300 mmol) was dissolved in 1.1 L of dimethylformamide (DMF) under a nitrogen environment, and bis(pinacolato) diboron (91.5 g, 360 mmol), (1,1'-bis(diphenylphosphine)ferrocene)dichloropalladium (II) (4.90 g, 6.0 mmol), and potassium acetate (88.3 g, 900 mmol) were added thereto and then, heated and refluxed at 150° C. for 10 hours. When a reaction was complete, water was added to the reaction solution, and the mixture was filtered and dried in a vacuum oven. This obtained residue was separated and purified through flash column chromatography to obtain Intermediate I-3 (115 g, 73%).

HRMS (70 eV, EI+): m/z calcd for C33H29BN4O2: 524.2384, found: 524.

Elemental Analysis: C, 76%; H, 6%

Synthesis Example 4: Synthesis of Intermediate I-4

[Reaction Scheme 4]

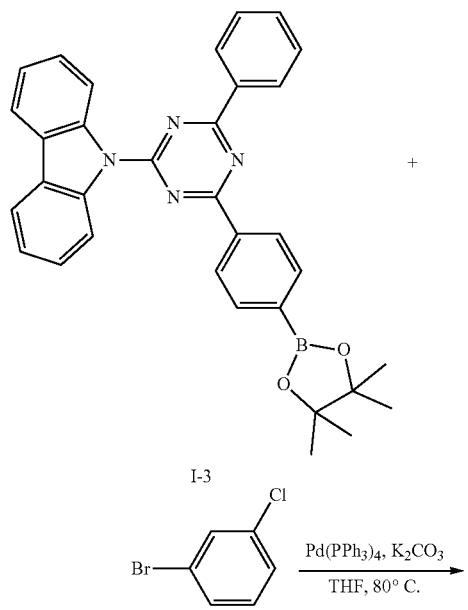

Intermediate I-4 (102 g, 95%) was obtained according to the same method as Synthesis Example 2 except that Intermediate I-3 (110 g, 210 mmol) and 2-bromo-3-chlorobenzene (48.2 g, 252 mmol) purchased from Tokyo Chemical Industry Co., Ltd. were used.

HRMS (70 eV, EI+): m/z calcd for C33H21ClN4: 508.1455, found: 508.

Elemental Analysis: C, 78%; H, 4%

Synthesis Example 5: Synthesis of Intermediate I-5

[Reaction Scheme 5]

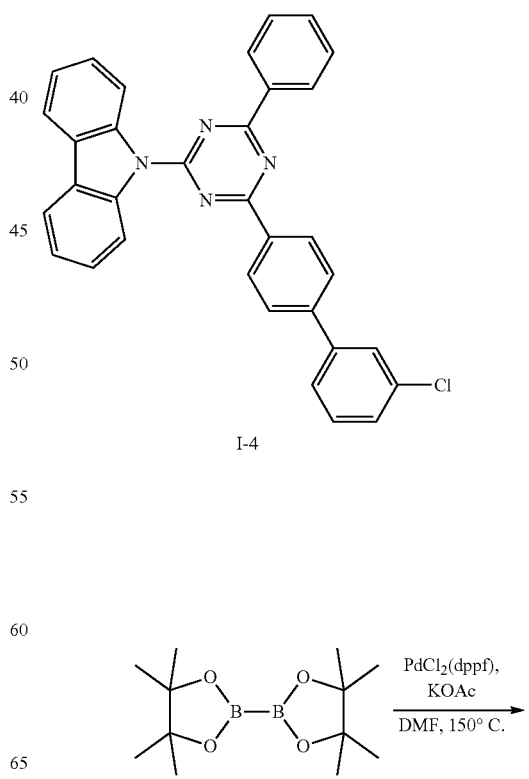

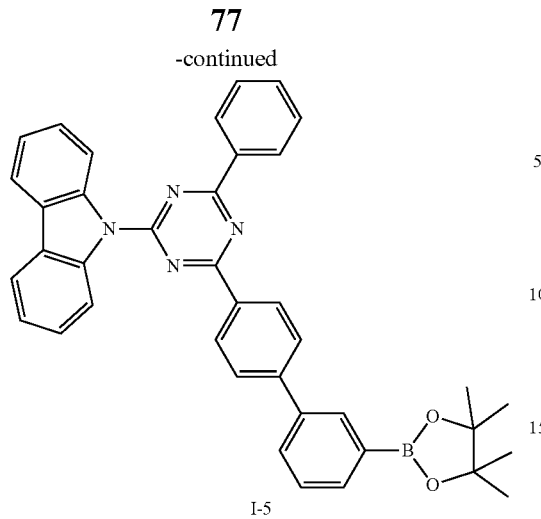

I-5

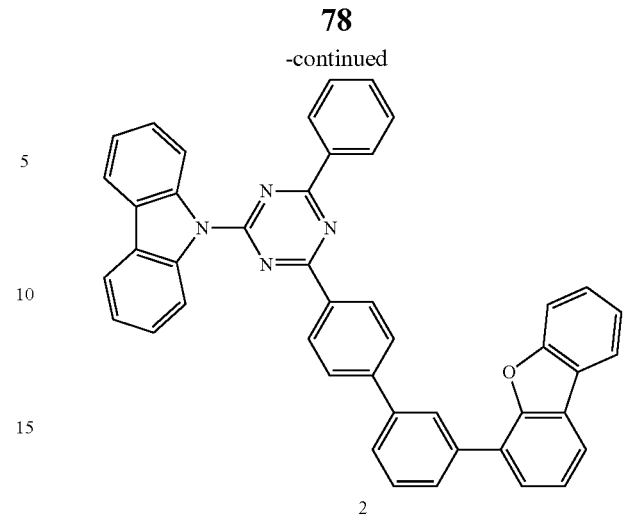

2

Intermediate I-5 (57.4 g, 54%) was obtained according to the same method as Synthesis Example 3 except that Intermediate I-4 (90 g, 177 mmol) was used.

HRMS (70 eV, EI+): m/z calcd for $C_{39}H_{33}BN_4O_2$: 600.2697, found: 600.

Elemental Analysis: C, 78%; H, 6%

Synthesis Example 6: Synthesis of Compound 2

Compound 2 (9.84 g, 92%) was obtained according to the same method as Synthesis Example 2 except that Intermediate I-5 (10 g, 16.7 mmol) and 4-bromodibenzofuran (11.7 g, 18.3 mmol) purchased from Tokyo Chemical Industry Co., Ltd. were used.

HRMS (70 eV, EI+): m/z calcd for $C_{45}H_{28}N_4O$: 640.2263, found: 640.

Elemental Analysis: C, 84%; H, 4%

Synthesis Example 7: Synthesis of Compound 3

[Reaction Scheme 6]

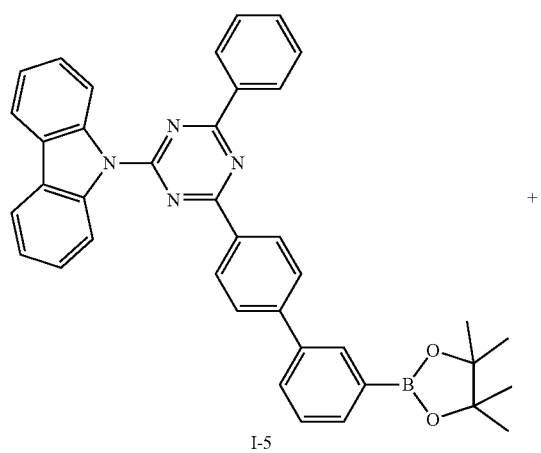

I-5

+

[Reaction Scheme 7]

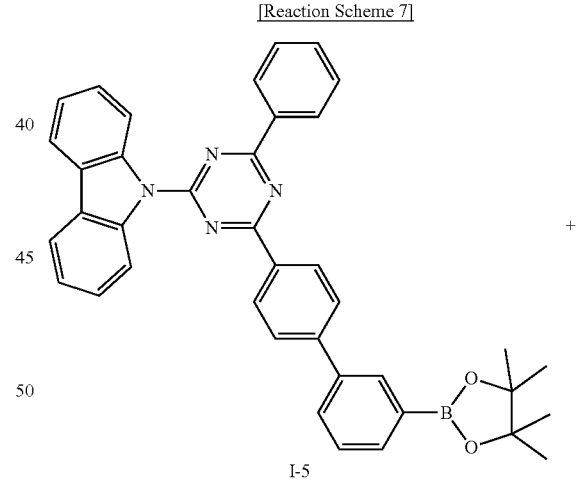

I-5

+

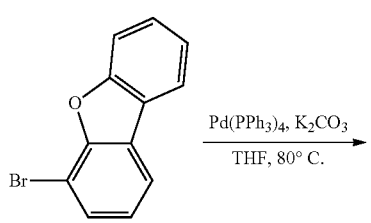

$\xrightarrow{\text{Pd(PPh}_3)_4\text{, K}_2\text{CO}_3}{\text{THF, 80° C.}}$

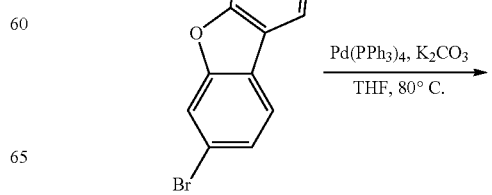

$\xrightarrow{\text{Pd(PPh}_3)_4\text{, K}_2\text{CO}_3}{\text{THF, 80° C.}}$

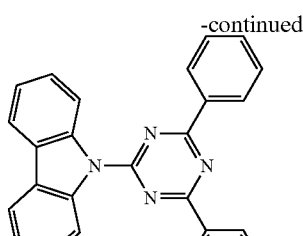

3

Compound 3 (10.2 g, 95%) was obtained according to the same method as Synthesis Example 2 except that Intermediate I-5 (10 g, 16.7 mmol) and 3-bromodibenzofuran (11.7 g, 18.3 mmol) purchased from Tokyo Chemical Industry Co., Ltd. were used.

HRMS (70 eV, EI+): m/z calcd for $C_{45}H_{28}N_4O$: 640.2263, found: 640.

Elemental Analysis: C, 84%; H, 4%

Synthesis Example 8: Synthesis of Intermediate I-6

HRMS (70 eV, EI+): m/z calcd for $C_{27}H_{17}ClN_4$: 432.1142, found: 432.

Elemental Analysis: C, 75%; H, 4%

Synthesis Example 9: Synthesis of Intermediate I-7

[Reaction Scheme 9]

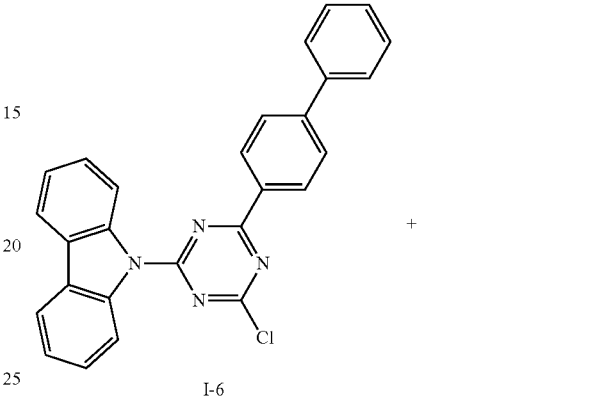

[Reaction Scheme 8]

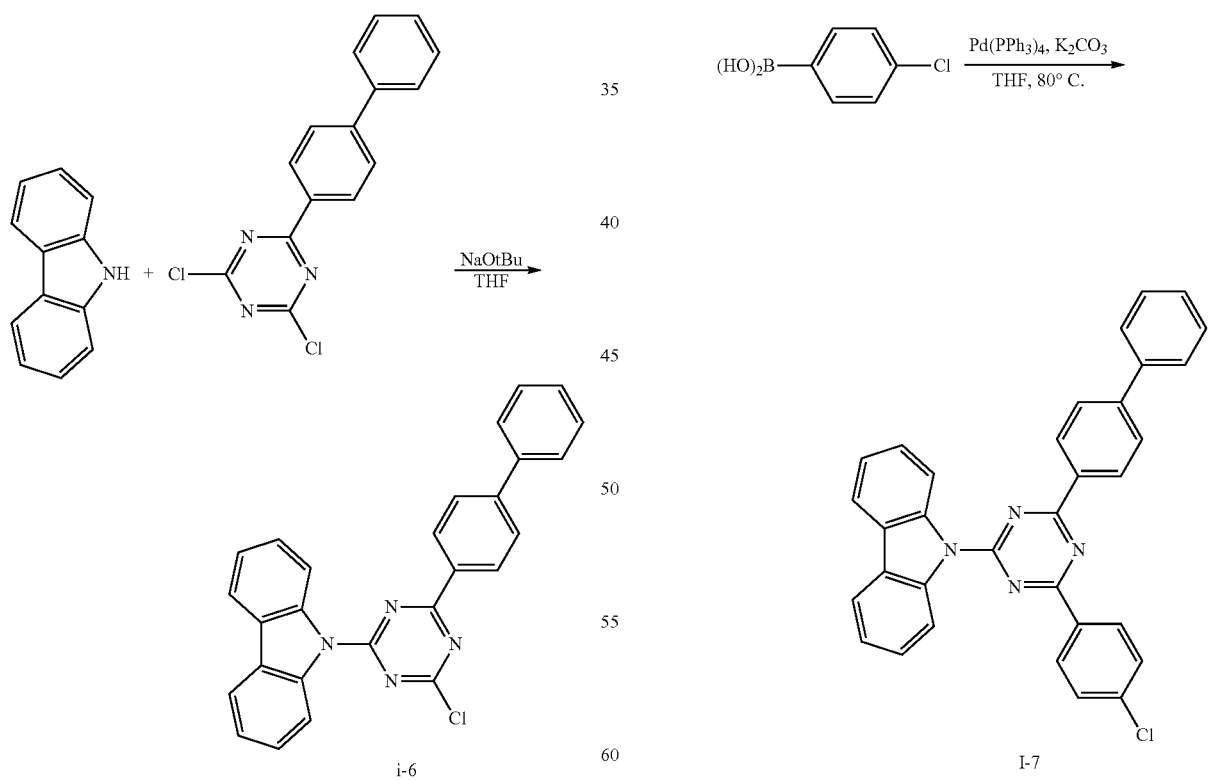

Intermediate I-6 (233 g, 90%) was obtained according to the same method as Synthesis Example 1 except that 9H-carbazole (100 g, 598 mmol) purchased from Tokyo Chemical Industry Co., Ltd. and 2-(biphenyl-4-yl)-4,6-dichloro-1,3,5-triazine (271 g, 897 mmol) were used.

Intermediate I-7 (230 g, 89%) was obtained according to the same method as Synthesis Example 2 except that Intermediate I-6 (220 g, 508 mmol) and 4-chlorophenylboronic acid (87.4 g, 559 mmol) purchased from Tokyo Chemical Industry Co., Ltd. were used.

HRMS (70 eV, EI+): m/z calcd for $C_{33}H_{21}ClN_4$: 508.1455, found: 508.

Elemental Analysis: C, 78%; H, 4%

Synthesis Example 10: Synthesis of Intermediate I-8

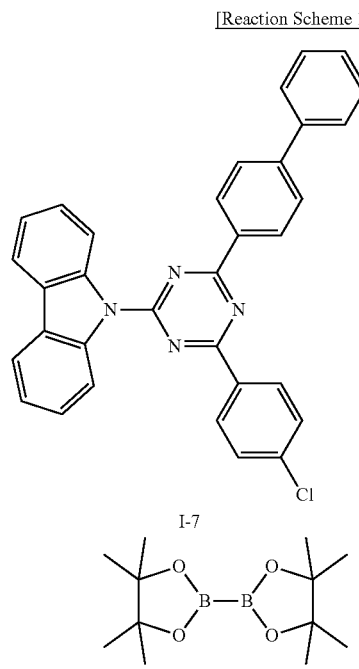

Intermediate I-8 (70.8 g, 60%) was obtained according to the same method as Synthesis Example 3 except that Intermediate I-7 was used.

HRMS (70 eV, EI+): m/z calcd for $C_{39}H_{33}BN_4O_2$: 600.2697, found: 600.

Elemental Analysis: C, 78%; H, 6%

Synthesis Example 11: Synthesis of Intermediate I-9

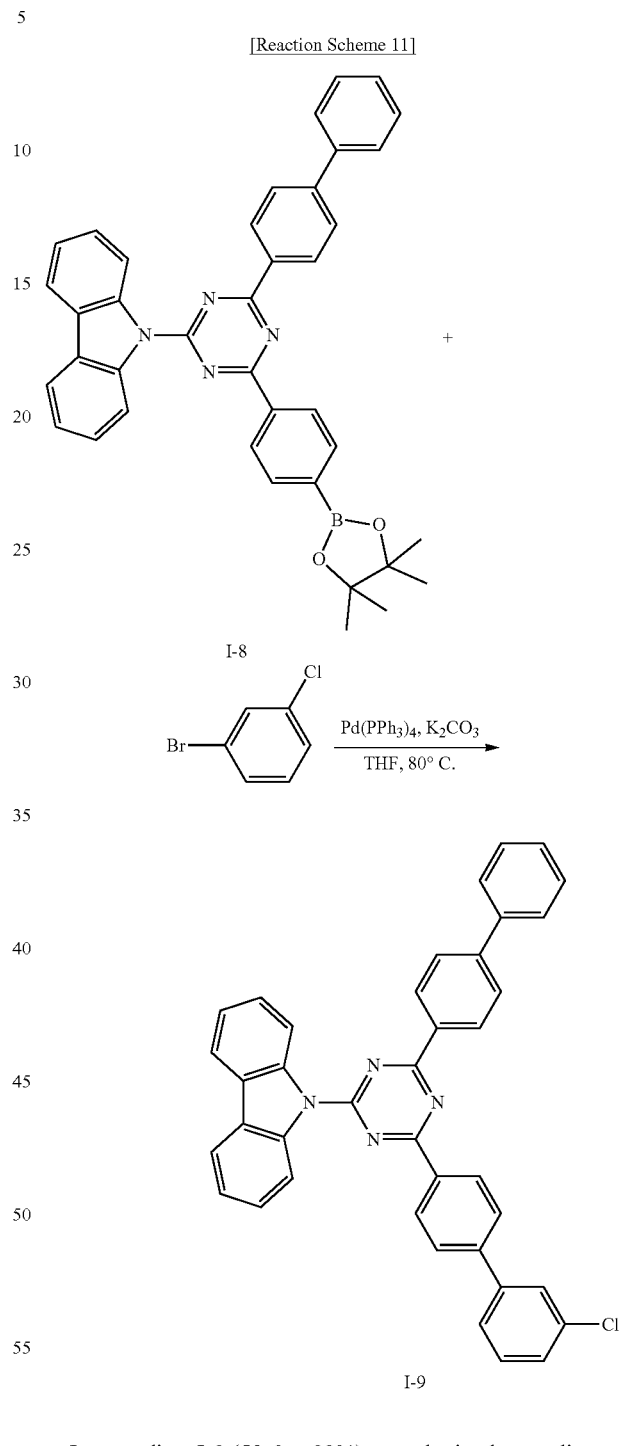

Intermediate I-9 (52.6 g, 90%) was obtained according to the same method as Synthesis Example 2 except that Intermediate I-8 (60 g, 99.9 mmol) and 1-bromo-3-chlorobenzene (23.0 g, 120 mmol) purchased from Tokyo Chemical Industry Co., Ltd. were used.

HRMS (70 eV, EI+): m/z calcd for $C_{39}H_{25}ClN_4$: 584.1768, found: 584.

Elemental Analysis: C, 80%; H, 4%

Synthesis Example 12: Synthesis of Intermediate I-10

[Reaction Scheme 12]

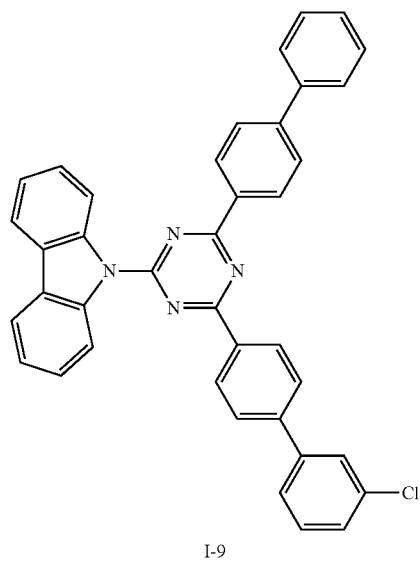

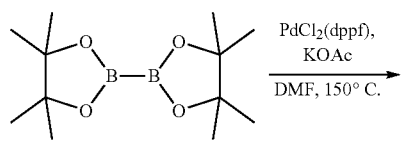

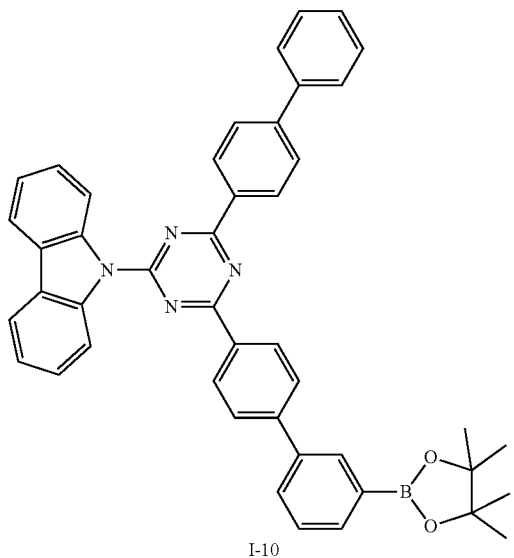

Intermediate I-10 (28.6 g, 55%) was obtained according to the same method as Synthesis Example 3 except that Intermediate I-9 (45 g, 76.9 mmol) was used.

HRMS (70 eV, EI+): m/z calcd for C45H37BN4O2: 676.3010, found: 676.

Elemental Analysis: C, 80%; H, 6%

Synthesis Example 13: Synthesis of Compound 6

[Reaction Scheme 13]

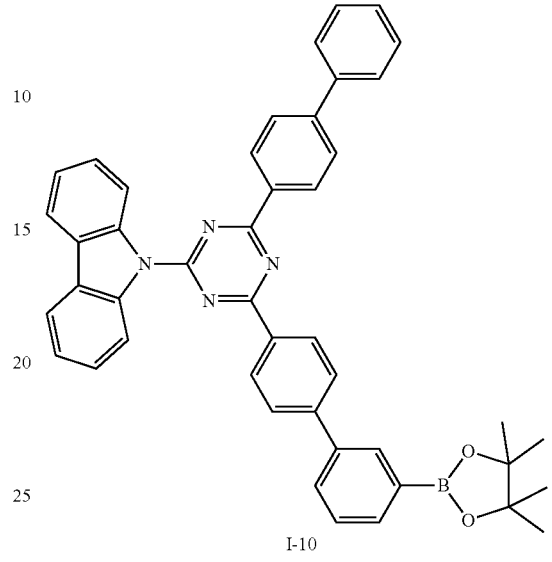

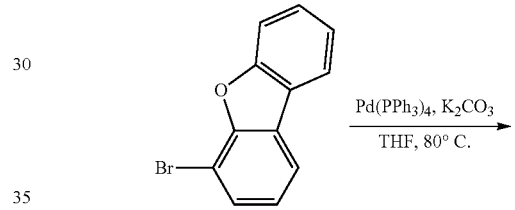

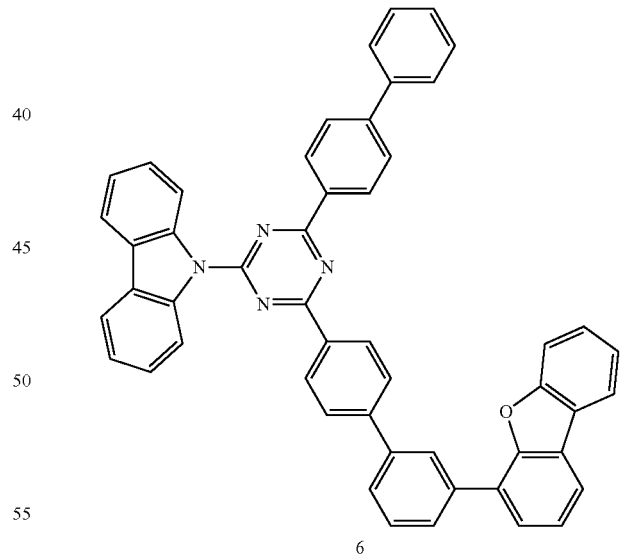

Compound 6 (10.1 g, 95%) was obtained according to the same method as Synthesis Example 2 except that Intermediate I-10 (10 g, 14.8 mmol) and 4-bromodibenzofuran (4.02 g, 16.3 mmol) purchased from Tokyo Chemical Industry Co., Ltd. were used.

HRMS (70 eV, EI+): m/z calcd for C51H32N4O: 716.2576, found: 716.

Elemental Analysis: C, 85%; H, 5%

Synthesis Example 14: Synthesis of Intermediate I-11

[Reaction Scheme 14]

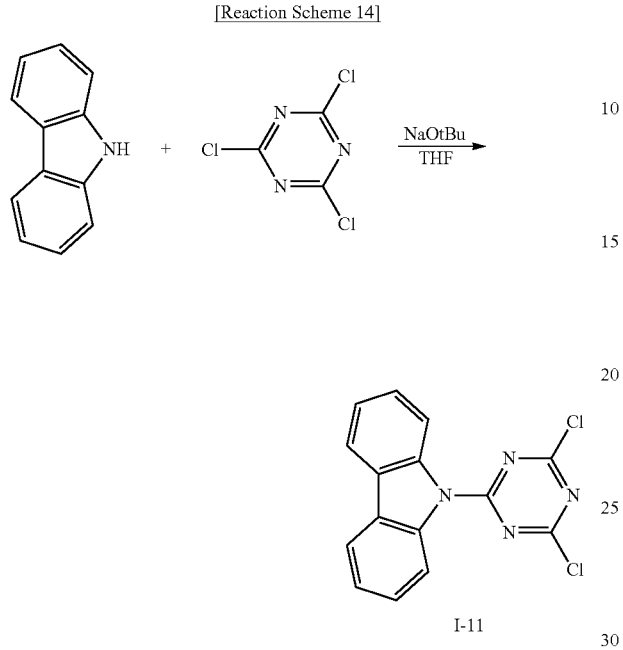

Intermediate I-11 (141 g, 75%) was obtained according to the same method as Synthesis Example 1 except that 9H-carbazole (100 g, 598 mmol) purchased from Tokyo Chemical Industry Co., Ltd. and cyanuric chloride (165 g, 897 mmol) were used.

HRMS (70 eV, EI+): m/z calcd for C15H8Cl2N4: 314.0126, found: 314.

Elemental Analysis: C, 57%; H, 3%

Synthesis Example 15: Synthesis of Intermediate I-12

[Reaction Scheme 15]

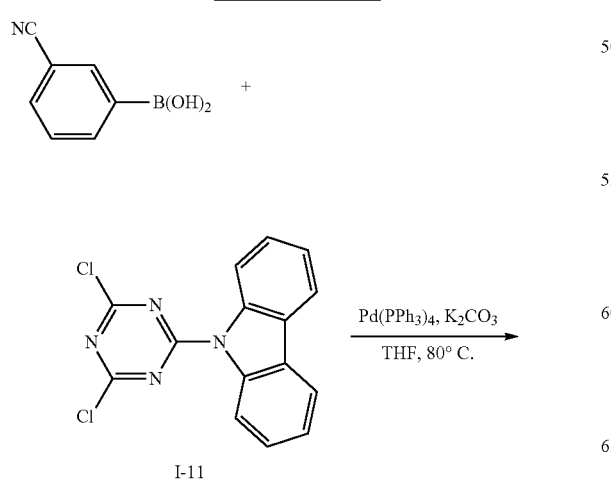

Intermediate I-12 (106 g, 81%) was obtained according to the same method as Synthesis Example 1 except that 3-cyanophenylboronic acid (50.5 g, 344 mmol) purchased from Tokyo Chemical Industry Co., Ltd. and Intermediate I-11 (130 g, 412 mmol) were used.

HRMS (70 eV, EI+): m/z calcd for C22H12ClN5: 381.0781, found: 381.

Elemental Analysis: C, 69%; H, 3%

Synthesis Example 16: Synthesis of Intermediate I-13

[Reaction Scheme 16]

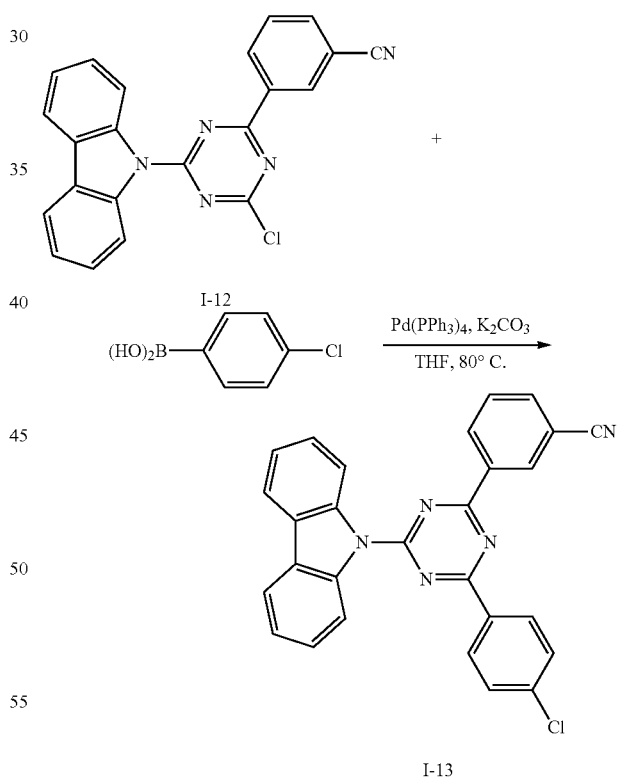

Intermediate I-13 (101 g, 84%) was obtained according to the same method as Synthesis Example 2 except that Intermediate I-12 (100 g, 262 mmol) and 4-chlorophenylboronic acid (49.2 g, 314 mmol) purchased from Tokyo Chemical Industry Co., Ltd. were used.

HRMS (70 eV, EI+): m/z calcd for C28H16ClN5: 457.1094, found: 457.

Elemental Analysis: C, 73%; H, 4%

Synthesis Example 17: Synthesis of Intermediate I-14

Synthesis Example 18: Synthesis of Intermediate I-15

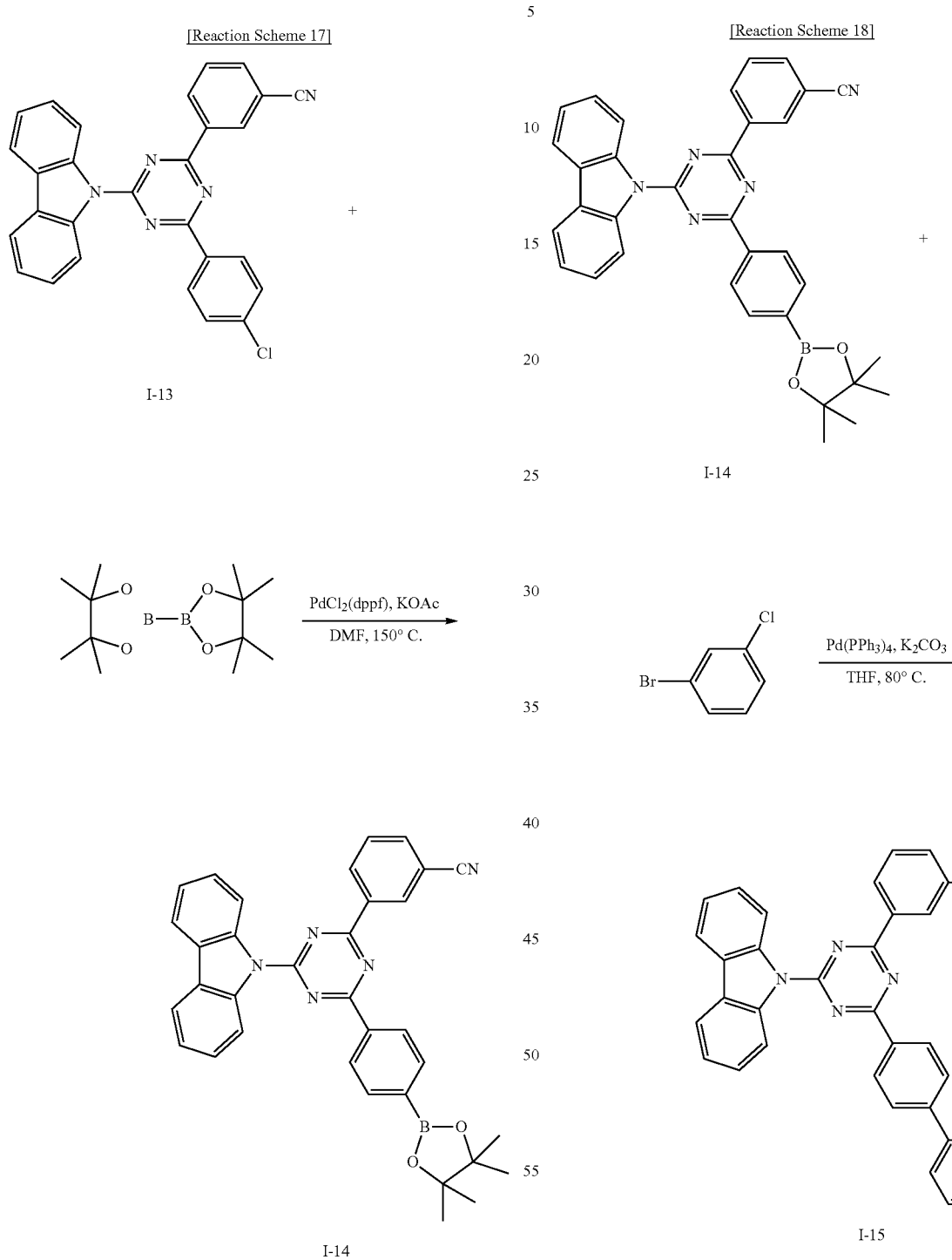

Intermediate I-14 (42.2 g, 37%) was obtained according to the same method as Synthesis Example 3 except that Intermediate I-13 (95 g, 207 mmol) was used.

HRMS (70 eV, EI+): m/z calcd for $C_{34}H_{28}BN_5O_2$: 549.2336, found: 549.

Elemental Analysis: C, 74%; H, 5%

Intermediate I-15 (27.6 g, 71%) was obtained according to the same method as Synthesis Example 2 except that Intermediate I-14 (40 g, 72.8 mmol) and 1-bromo-3-chlorobenzene (16.7 g, 87.4 mmol) purchased from Tokyo Chemical Industry Co., Ltd. were used.

HRMS (70 eV, EI+): m/z calcd for $C_{34}H_{20}ClN_5$: 533.1407, found: 533.

Elemental Analysis: C, 76%; H, 4%

Synthesis Example 19: Synthesis of Intermediate I-16

Synthesis Example 20: Synthesis of Compound 8

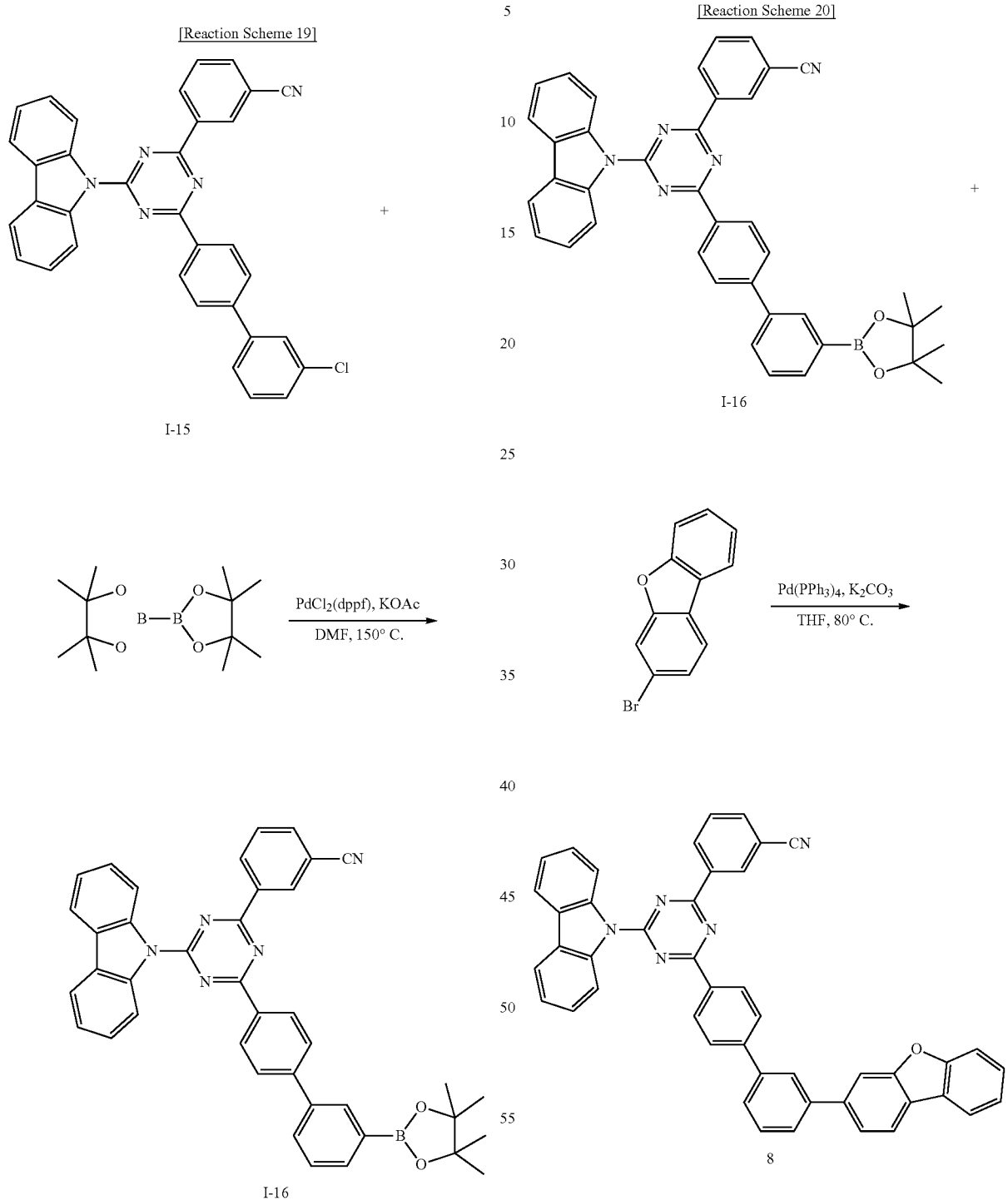

Intermediate I-16 (5.56 g, 19%) was obtained according to the same method as Synthesis Example 3 except that Intermediate I-15 (25 g, 46.8 mmol) was used.

HRMS (70 eV, EI+): m/z calcd for $C_{40}H_{32}BN_5O_2$: 625.2649, found: 625.

Elemental Analysis: C, 77%; H, 5%

Compound 8 (2.82 g, 53%) was obtained according to the same method as Synthesis Example 2 except that Intermediate I-16 (5 g, 7.99 mmol) and 3-bromodibenzofuran (2.17 g, 8.79 mmol) purchased from Tokyo Chemical Industry Co., Ltd. were used.

HRMS (70 eV, EI+): m/z calcd for $C_{46}H_{27}N_5O$: 665.2216, found: 665.

Elemental Analysis: C, 83%; H, 4%

Synthesis Example 21: Synthesis of Intermediate I-17

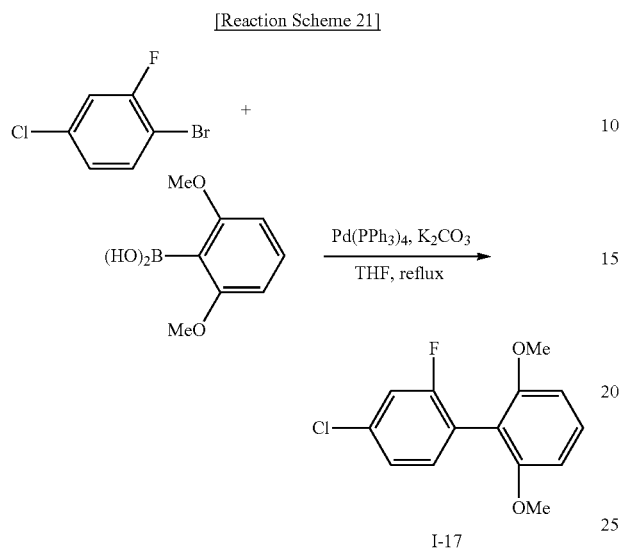

Intermediate I-17 (46.5 g, 73%) was obtained according to the same method as Synthesis Example 2 except that 1-bromo-4-chloro-2-fluorobenzene (50 g, 239 mmol) and 2,6-dimethoxyphenylboronic acid (43.4 g, 239 mmol) purchased from Sigma Aldrich Co., Ltd. (http://www.sigmaaldrich.com/) were used.

HRMS (70 eV, EI+): m/z calcd for $C_{14}H_{12}ClFO_2$: 266.0510, found: 266.

Elemental Analysis: C, 63%; H, 5%

Synthesis Example 22: Synthesis of Intermediate I-18

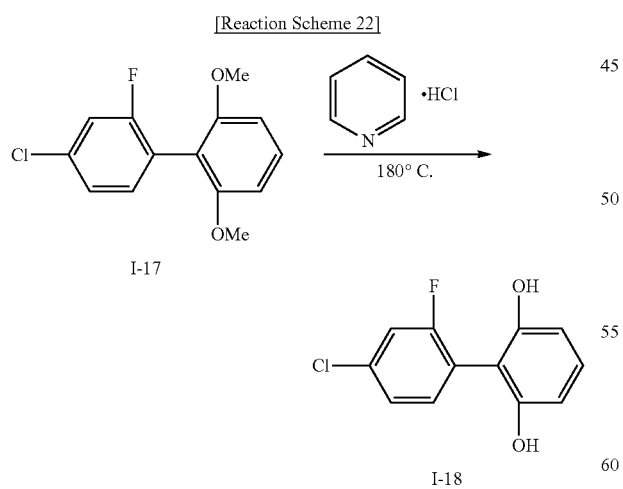

Intermediate I-17 (45 g, 169 mmol) and pyridine hydrochloride (347 g, 1,687 mmol) were put under a nitrogen atmosphere and then, heated and refluxed at 180° C. for 12 hours. When a reaction was complete, water was added to the reaction solution, and the mixture was extracted with ethyl acetate (EA), treated with anhydrous magnesium sulfate to remove moisture, filtered, and concentrated under a reduced pressure. This obtained residue was separated and purified through flash column chromatography to obtain Intermediate I-18 (31.9 g, 79%).

HRMS (70 eV, EI+): m/z calcd for $C_{12}H_8ClFO_2$: 238.0197, found: 238.

Elemental Analysis: C, 60%; H, 3%

Synthesis Example 23: Synthesis of Intermediate I-19

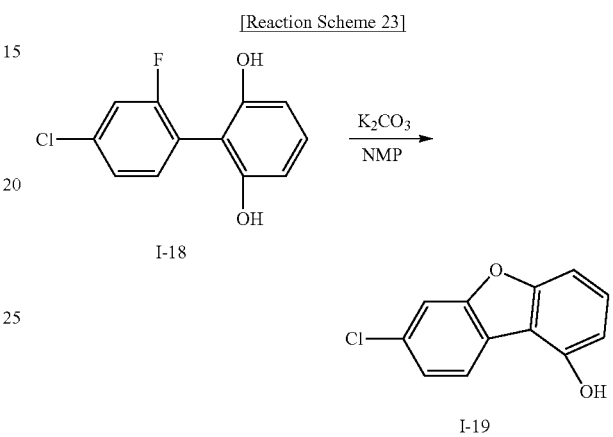

Intermediate I-18 (30 g, 12 6 mmol) was dissolved in 0.3 L of N-methyl-2-pyrrolidone (NMP) under a nitrogen atmosphere, and potassium carbonate (34.8 g, 252 mmol) was added thereto and then, heated and refluxed for 14 hours. When a reaction was complete, after removing the solvent therefrom through distillation, water was added to the reaction solution, and the mixture was extracted with dichloromethane (DCM), treated with anhydrous magnesium sulfate to remove moisture, filtered, and concentrated under a reduced pressure. This obtained residue was separated and purified through flash column chromatography to obtain Intermediate I-19 (19.3 g, 70%).

HRMS (70 eV, EI+): m/z calcd for $C_{12}H_7ClO_2$: 218.0135, found: 218.

Elemental Analysis: C, 66%; H, 3%

Synthesis Example 24: Synthesis of Intermediate I-20

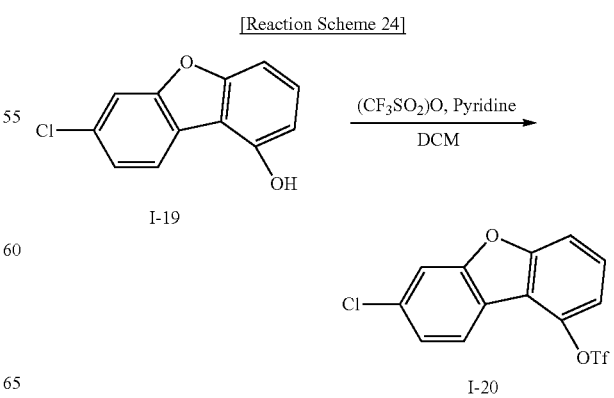

Intermediate I-19 (18 g, 82.3 mmol) was dissolved in 0.3 L of dichloromethane (DCM) under a nitrogen atmosphere and then, cooled down to 0° C. Then, pyridine (7.8 g, 98.8 mmol) was added thereto and stirred for 30 minutes, and tifluoromethanesulfonic anhydride (27.9 g, 98.8 mmol) was added thereto and stirred therewith. After 14 hours, the reaction solution was cooled down to 0° C., water was slowly added thereto for 30 minutes, and the mixture was extracted with dichloromethane (DCM), treated with anhydrous magnesium sulfate to remove moisture, and concentrated under a reduced pressure. This obtained residue was separated and purified through flash column chromatography to obtain Intermediate I-20 (27.4 g, 95%).

HRMS (70 eV, EI+): m/z calcd for C13H6ClF3O4S: 349.9627, found: 350.

Elemental Analysis: C, 45%; H, 2%

Synthesis Example 25: Synthesis of Intermediate I-21

[Reaction Scheme 25]

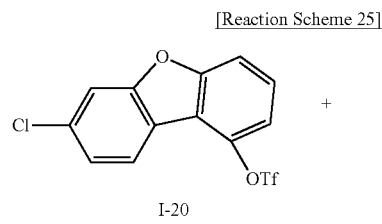

I-20

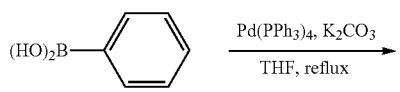

$\xrightarrow{\text{Pd(PPh}_3)_4, \text{K}_2\text{CO}_3}_{\text{THF, reflux}}$

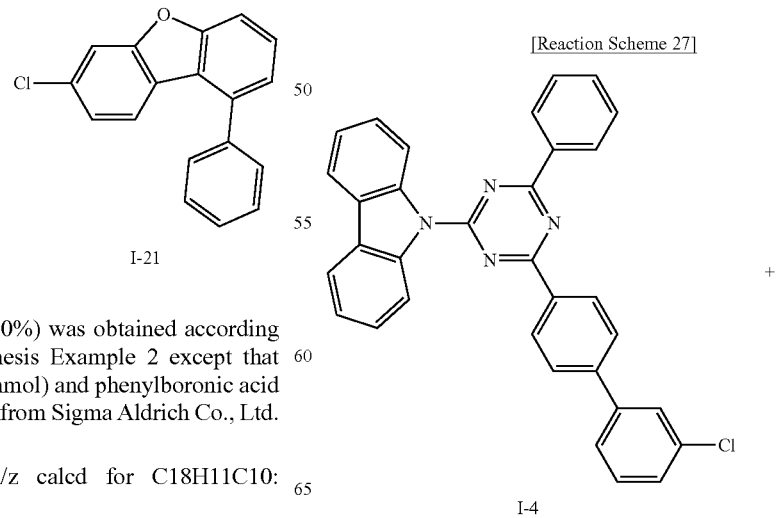

I-21

Intermediate I-21 (17.9 g, 90%) was obtained according to the same method as Synthesis Example 2 except that Intermediate I-20 (25 g, 71.3 mmol) and phenylboronic acid (10.4 g, 85.5 mmol) purchased from Sigma Aldrich Co., Ltd. were used.

HRMS (70 eV, EI+): m/z calcd for C18H11ClO: 278.0498, found: 278.

Elemental Analysis: C, 78%; H, 4%

Synthesis Example 26: Synthesis of Intermediate I-22

[Reaction Scheme 26]

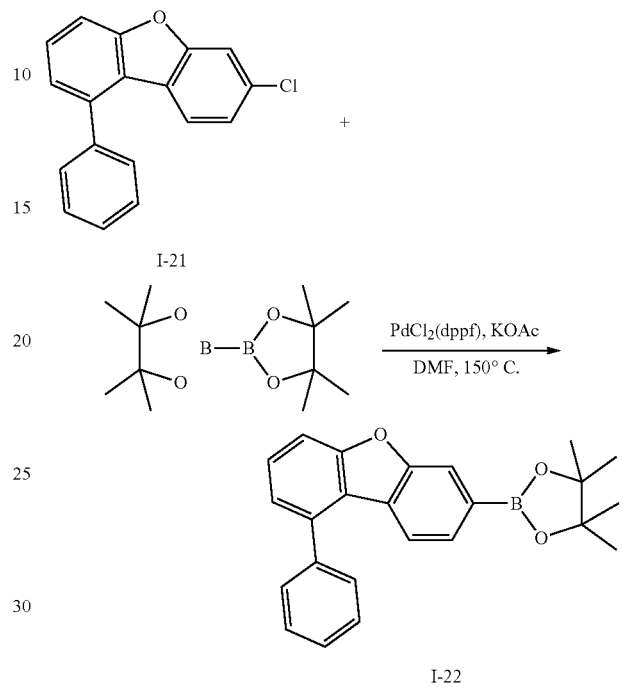

Intermediate I-22 (13.7 g, 69%) was obtained according to the same method as Synthesis Example 3 except that Intermediate I-21 (15 g, 53.8 mmol) was used.

HRMS (70 eV, EI+): m/z calcd for C24H23BO3: 370.1740, found: 370.

Elemental Analysis: C, 78%; H, 6%

Synthesis Example 27: Synthesis of Compound 11

[Reaction Scheme 27]

I-4

95

-continued

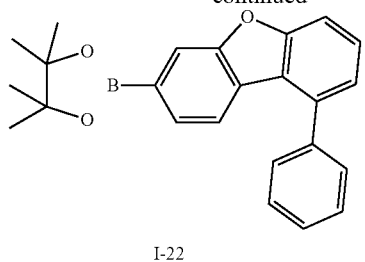

I-22

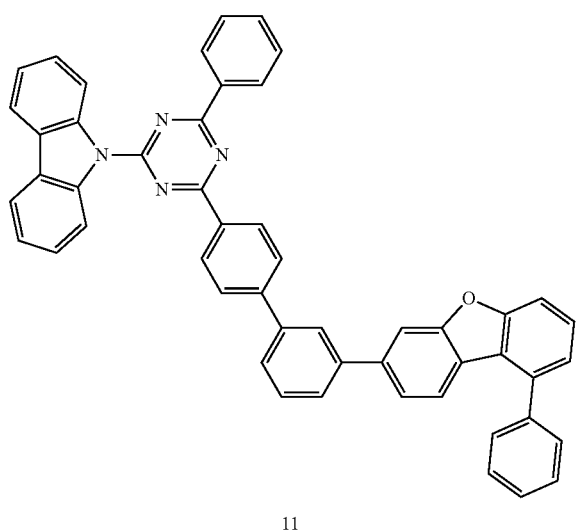

11

Intermediate I-4 (10 g, 19.6 mmol) was dissolved in 0.1 L of dioxane under a nitrogen atmosphere, and Intermediate I-22 (7.27 g, 19.6 mmol), tris(diphenylideneacetone) dipalladium (0) (0.18 g, 0.20 mmol), tris(tert butyl) phosphine (0.20 g, 0.98 mmol), and cesium carbonate (16.0 g, 49.0 mmol) were sequentially added thereto and then, heated and refluxed at 110° C. for 25 hours. When a reaction was complete, water was added to the reaction solution, and the mixture was extracted with dichloromethane (DCM), treated with anhydrous magnesium sulfate to remove moisture, filtered, and concentrated under a reduced pressure. This obtained residue was separated and purified through flash column chromatography to obtain Compound 11 (6.88 g, 49%).

HRMS (70 eV, EI+): m/z calcd for $C_{51}H_{32}N_4O$: 716.2576, found: 716.

Elemental Analysis: C, 85%; H, 5%

96

Synthesis Example 28: Synthesis of Compound 34

[Reaction Scheme 28]

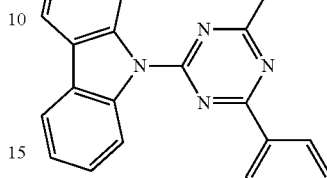

I-5

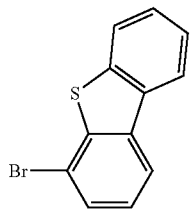

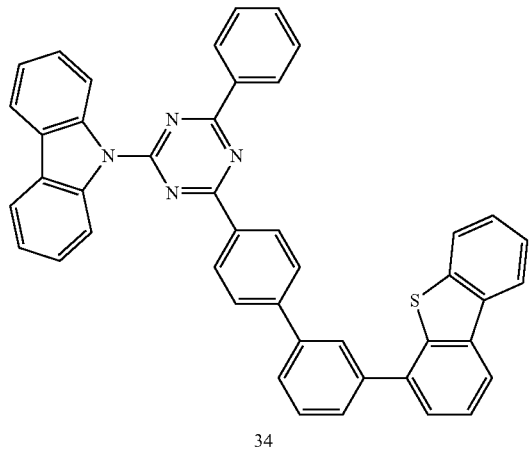

34

Compound 34 (10.4 g, 95%) was obtained according to the same method as Synthesis Example 2 except that Intermediate I-5 (10 g, 16.7 mmol) and 4-bromodibenzothiophene (4.82 g, 18.3 mmol) purchased from Tokyo Chemical Industry Co., Ltd were used.

HRMS (70 eV, EI+): m/z calcd for $C_{45}H_{28}N_4S$: 656.2035, found: 656.

Elemental Analysis: C, 82%; H, 4%

Synthesis Example 29: Synthesis of Host-1

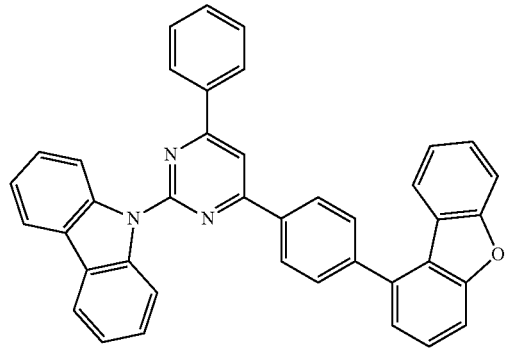

Host-1

Host-1 was synthesized by referring to the synthesis method of U.S. Pat. No. 9,847,501.

HRMS (70 eV, EI+): m/z calcd for $C_{40}H_{25}N_3O$: 563.1998, found: 563.

Elemental Analysis: C, 85%; H, 4%

Synthesis Example 30: Synthesis of Host-2

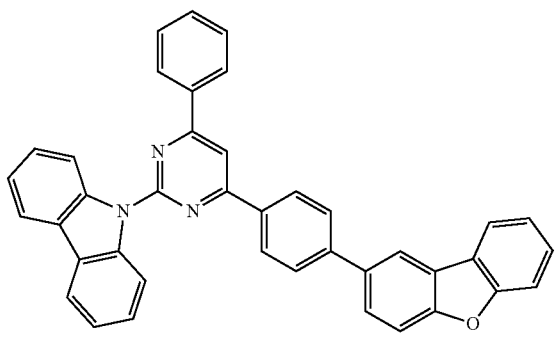

Host-2

Host-2 was synthesized by referring to the synthesis method of U.S. Pat. No. 9,847,501.

HRMS (70 eV, EI+): m/z calcd for $C_{40}H_{25}N_3O$: 563.1998, found: 563.

Elemental Analysis: C, 85%; H, 4%

Synthesis Example 31: Synthesis of Host-3

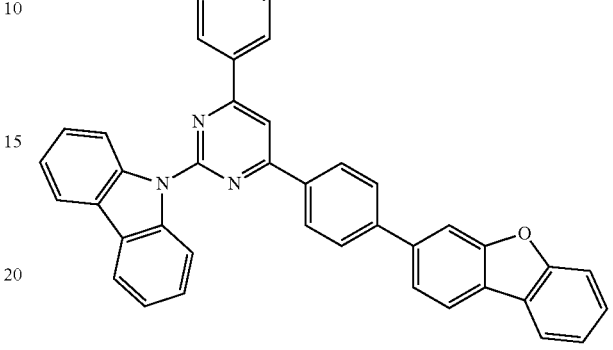

Host-3

Host-3 was synthesized by referring to the synthesis method of U.S. Pat. No. 9,847,501.

HRMS (70 eV, EI+): m/z calcd for $C_{40}H_{25}N_3O$: 563.1998, found: 563.

Elemental Analysis: C, 85%; H, 4%

Synthesis Example 32: Synthesis of Host-4

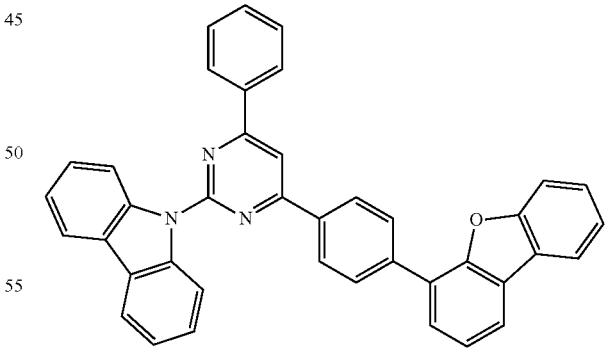

Host-4

Host-4 was synthesized by referring to the synthesis method of U.S. Pat. No. 9,847,501.

HRMS (70 eV, EI+): m/z calcd for $C_{40}H_{25}N_3O$: 563.1998, found: 563.

Elemental Analysis: C, 85%; H, 4%

Synthesis Example 33: Synthesis of Host-5

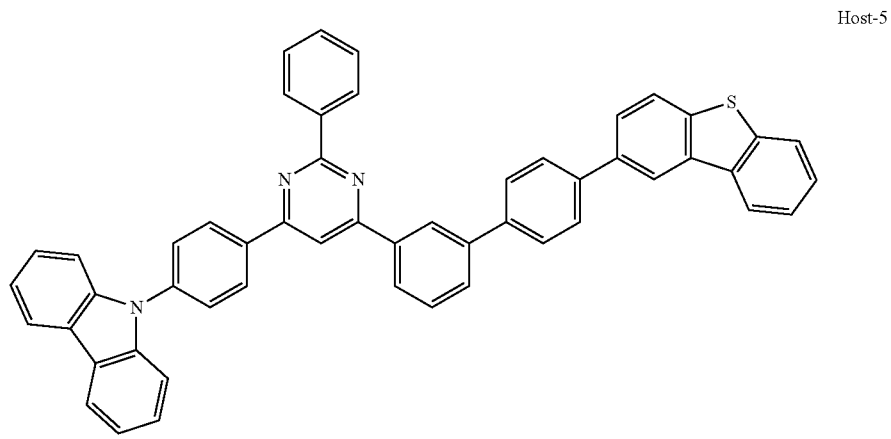 [SMILES: c1ccc(-c2nc(-c3ccc(-n4c5ccccc5c5ccccc54)cc3)cc(-c3cccc(-c4ccc(-c5ccc6sc7ccccc7c6c5)cc4)c3)n2)cc1]

Host-5

Host-5 was synthesized by referring to the synthesis method of U.S. Pat. No. 9,847,501.

HRMS (70 eV, EI+): m/z calcd for $C_{52}H_{33}N_3S$: 731.2395, found: 731.

Elemental Analysis: C, 85%; H, 5%

Synthesis Example 34: Synthesis of Host-6

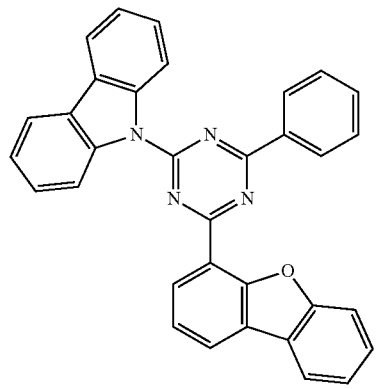

Host-6

Host-6 was synthesized by referring to the synthesis method of patent KR 2015-0070860.

HRMS (70 eV, EI+): m/z calcd for $C_{33}H_{20}N_4O$: 488.1637, found: 488.

Elemental Analysis: C, 81%; H, 5%

Synthesis Example 35: Synthesis of Compound Host-7

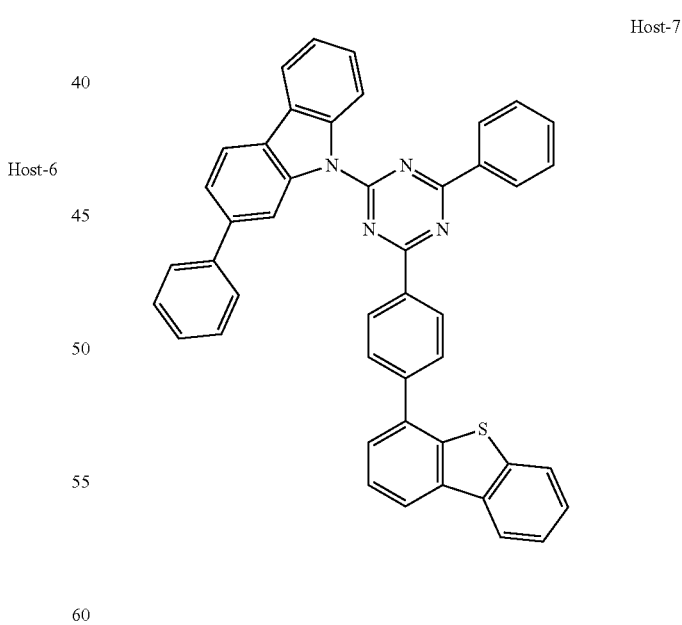

Host-7

Host-7 was synthesized by referring to the synthesis method of patent KR 2014-0046541.

HRMS (70 eV, EI+): m/z calcd for $C_{45}H_{28}N_4S$: 656.2035, found: 656.

Elemental Analysis: C, 82%; H, 4%

Synthesis Example 36: Synthesis of Host-8

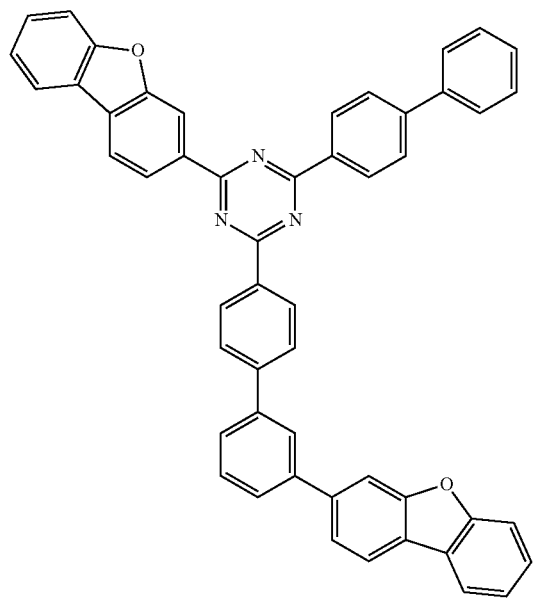
Host-8

Host-8 was synthesized by referring to the synthesis method of patent KR 2018-0013449.
HRMS (70 eV, EI+): m/z calcd for $C_{51}H_{31}N_3O_2$: 717.2416, found: 717.
Elemental Analysis: C, 85%; H, 4%

Synthesis Example 37: Synthesis of Compound Host-9

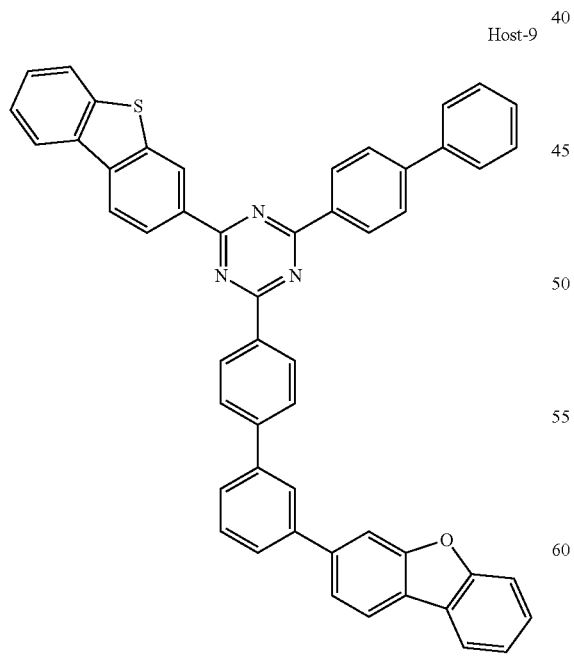
Host-9

Host-9 was synthesized by referring to the synthesis method of patent KR 2018-0013449.
HRMS (70 eV, EI+): m/z calcd for $C_{51}H_{31}N_3OS$: 733.2188, found: 733.
Elemental Analysis: C, 83%; H, 4%

Synthesis Example 38: Synthesis of Host-10

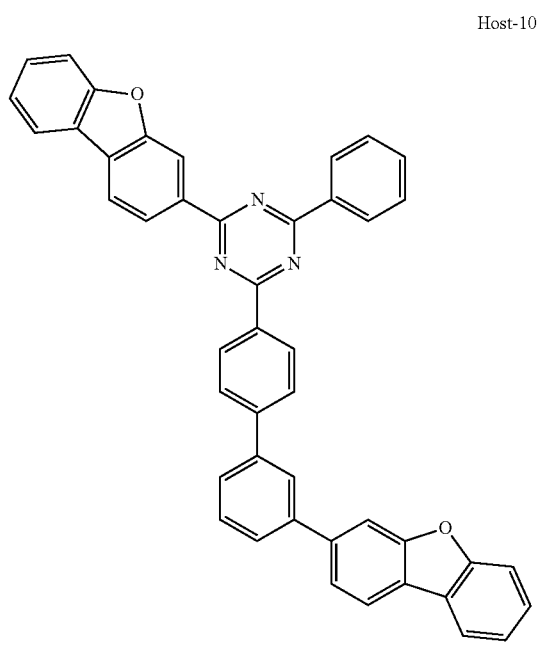
Host-10

Host-10 was synthesized by referring to the synthesis method of patent KR 2018-0002353.
HRMS (70 eV, EI+): m/z calcd for $C_{45}H_{27}N_3O_2$: 641.2103, found: 641.
Elemental Analysis: C, 84%; H, 4%

Synthesis Example 39: Synthesis of Compound Host-11

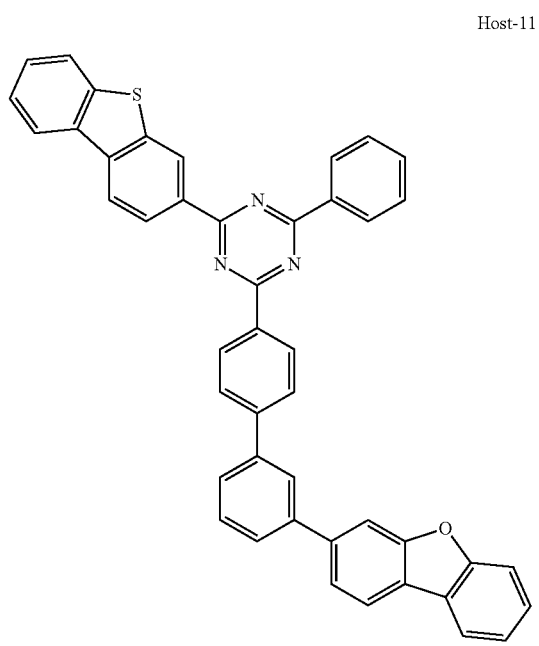 [SMILES: c1ccc(-c2nc(-c3ccc(-c4cccc(-c5ccc6c(c5)oc5ccccc56)c4)cc3)nc(-c3ccc4c(c3)oc3ccccc34)n2)cc1]
Host-11

Host-11 was synthesized by referring to the synthesis method of patent KR 2018-0002353.

HRMS (70 eV, EI+): m/z calcd for C45H27N3OS: 657.1875, found: 657.

Elemental Analysis: C, 82%; H, 4%

Production of Organic Light Emitting Diode

Example 1

A glass substrate coated with ITO (Indium tin oxide) with a thickness of 1,500 Å was washed with distilled water ultrasonically. After washing with the distilled water, the glass substrate was ultrasonically washed with a solvent of isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 1,020 Å-thick to form a hole transport layer. On the hole transport layer, 400 Å-thick light emitting layer was formed by simultaneously using (e.g., a mixture of) Compound 2 and Compound E as a host and doping 2 wt % of 10 wt % of tris(2-phenylpyridine)iridium(III) [Ir(ppy)$_3$]. Herein, Compound 2 and Compound E were used in a 3:7 weight ratio. Subsequently, on the light emitting layer, a 300 Å-thick electron transport layer was formed by simultaneously vacuum-depositing Compound D and Liq in a ratio of 1:1, and on the electron transport layer, Liq and Al were sequentially vacuum-deposited to be 15 Å-thick and 1200 Å-thick, producing an organic light emitting diode.

The organic light emitting diode had a five-layered organic thin layer, and specifically the following structure.

ITO/Compound A (700 Å)/Compound B (50 Å)/Compound C (1,020 Å)/EML [Compound 2:Compound E:Ir (ppy)$_3$=3:7:10%] (400 Å)/Compound D:Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinolone Compound E: 9,9'-di(biphenyl-4-yl)-9H,9'H-3,3'-bicarbazole

Examples 2 to 6

Organic light emitting diodes were produced according to the same method as Example 1 except that Compound 2 was changed into compositions shown in Table 1.

Comparative Examples 1 to 11

Organic light emitting diodes were produced according to the same method as Example 1 except that Compound 2 was changed into compositions shown in Table 1.

(Evaluation)

Driving voltages, current efficiency, and life-span characteristics of the organic light emitting diodes according to Examples 1 to 6 and Comparative Examples 1 to 11 were evaluated.

Specific measurement methods thereof are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Current Efficiency

Current efficiency (cd/A) at the same current density (10 mA/cm$^2$) were calculated by using the luminance, current density, and voltages (V) from the items (1) and (2).

(4) Measurement of Life-Span

Time taken until current efficiency (cd/A) was reduced into 97% while luminance (cd/m$^2$) was maintained at 6,000 cd/m$^2$ was measured.

TABLE 1

| No. | host | Driving voltage (V) | Color (EL color) | Current efficiency (cd/A) | Life-span T97 (h) |
| --- | --- | --- | --- | --- | --- |
| Example 1 | Compound 2/ Compound E | 4.10 | Green | 55.0 | 1,200 |
| Example 2 | Compound 3/ Compound E | 4.04 | Green | 58.5 | 1,000 |
| Example 3 | Compound 6/ Compound E | 3.98 | Green | 60.2 | 1,080 |
| Example 4 | Compound 8/ Compound E | 4.25 | Green | 50.8 | 1,310 |
| Example 5 | Compound 11/ Compound E | 3.95 | Green | 60.0 | 1,150 |
| Example 6 | Compound 34/ Compound E | 4.10 | Green | 59.5 | 950 |
| Comparative Example 1 | Host-1/ Compound E | 4.44 | Green | 48.2 | 300 |

TABLE 1-continued

| No. | host | Driving voltage (V) | Color (EL color) | Current efficiency (cd/A) | Life-span T97 (h) |
|---|---|---|---|---|---|
| Comparative Example 2 | Host-2/ Compound E | 4.35 | Green | 50.0 | 250 |
| Comparative Example 3 | Host-3/ Compound E | 4.41 | Green | 49.1 | 360 |
| Comparative Example 4 | Host-4/ Compound E | 4.50 | Green | 45.5 | 400 |
| Comparative Example 5 | Host-5/ Compound E | 4.40 | Green | 47.5 | 350 |
| Comparative Example 6 | Host-6/ Compound E | 4.32 | Green | 48.0 | 580 |
| Comparative Example 7 | Host-7/ Compound E | 4.30 | Green | 49.2 | 650 |
| Comparative Example 8 | Host-8/ Compound E | 4.40 | Green | 49.5 | 880 |
| Comparative Example 9 | Host-9/ Compound E | 4.51 | Green | 50.0 | 350 |
| Comparative Example 10 | Host-10/ Compound E | 4.45 | Green | 48.9 | 800 |
| Comparative Example 11 | Host-11/ Compound E | 4.57 | Green | 49.8 | 200 |

Referring to Table 1, the organic light emitting diodes according to Examples 1 to 6 exhibited significantly improved driving voltage, luminous efficiency, and life-span characteristics compared with the organic light emitting diodes according to Comparative Examples 1 to 11.

One or more embodiments may provide a compound for an organic optoelectronic device capable of realizing a high efficiency and long life-span organic optoelectronic device while lowering a driving voltage.

One or more embodiments may provide an organic optoelectronic device having low driving, high efficiency, and long life-span may be realized.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by Chemical Formula 1,

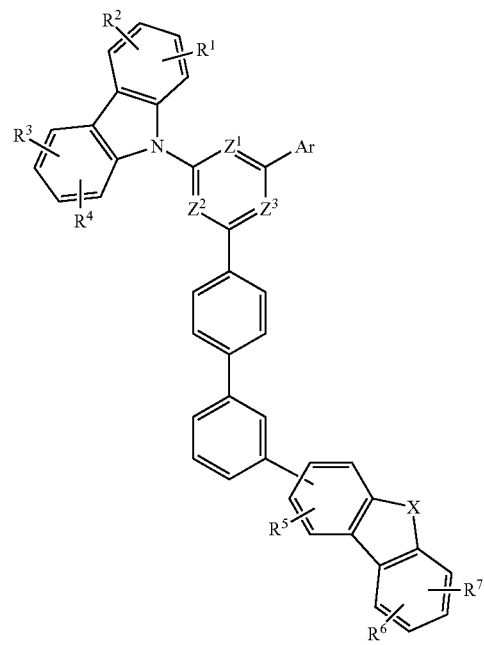

[Chemical Formula 1]

wherein, in Chemical Formula 1,
X is O or S,
$Z^1$ to $Z^3$ are independently N or $CR^a$, at least two of $Z^1$ to $Z^3$ being N,
Ar is a substituted or unsubstituted C6 to C18 aryl group, and
$R^a$ and $R^1$ to $R^7$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

2. The compound for an organic optoelectronic device as claimed in claim 1, wherein the compound represented by Chemical Formula 1 is represented by one of Chemical Formula 1-1 to Chemical Formula 1-4,

[Chemical Formula 1-1]

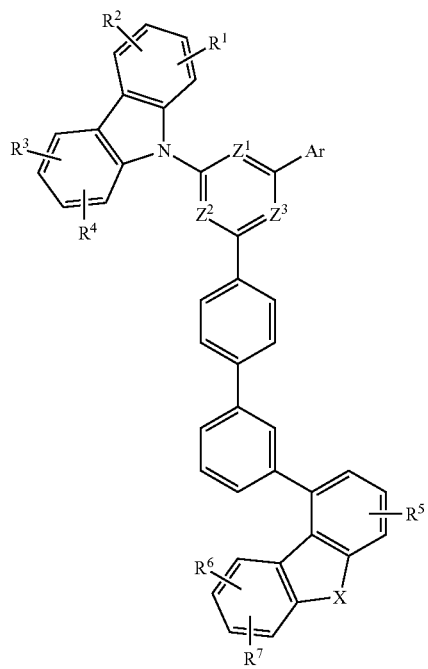

[Chemical Formula 1-2]

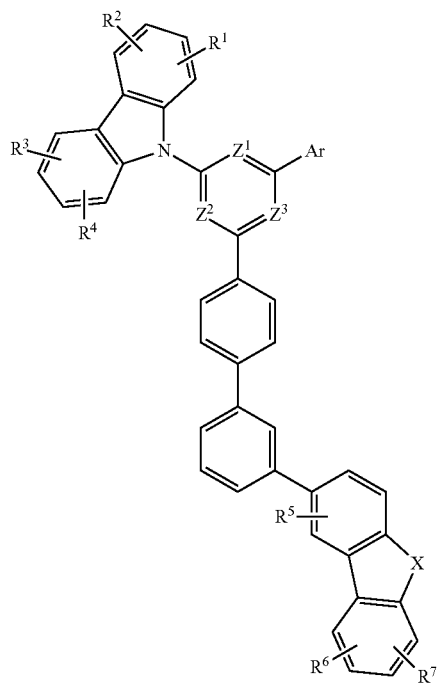

[Chemical Formula 1-3]

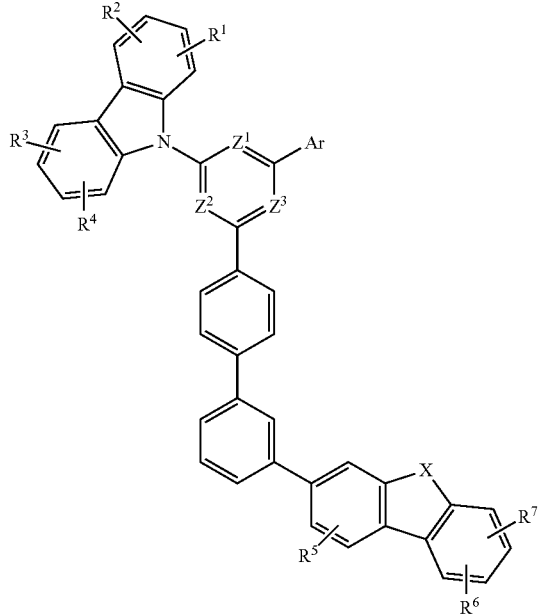

[Chemical Formula 1-4]

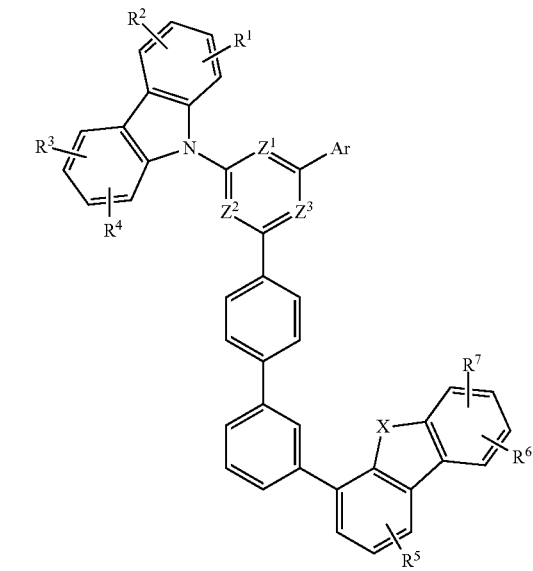

wherein, in Chemical Formula 1-1 to Chemical Formula 1-4,

X is O or S, $Z^1$ to $Z^3$ are independently N or $CR^a$, at least two of $Z^1$ to $Z^3$ being N, Ar is a substituted or unsubstituted C6 to C18 aryl group, and $R^a$ and $R^1$ to $R^7$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

3. The compound for an organic optoelectronic device as claimed in claim 2, wherein:

the compound represented by Chemical Formula 1 is represented by Chemical Formula 1-1, and the compound represented by Chemical Formula 1-1 is represented by one of Chemical Formula 1-1a to Chemical Formula 1-1d:

[Chemical Formula 1-1a]

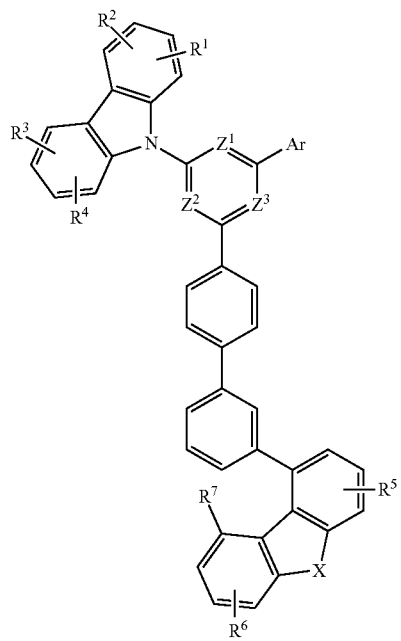

[Chemical Formula 1-1b]

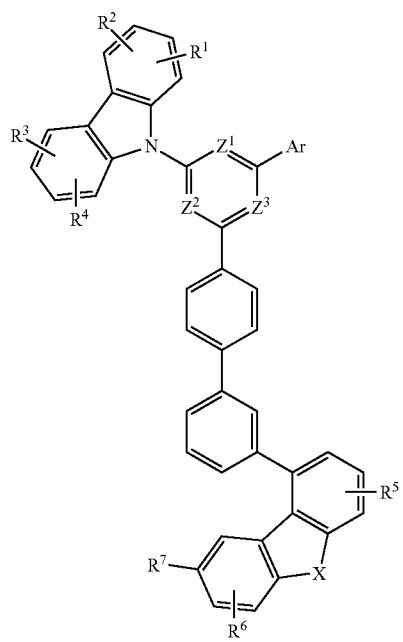

[Chemical Formula 1-1c]

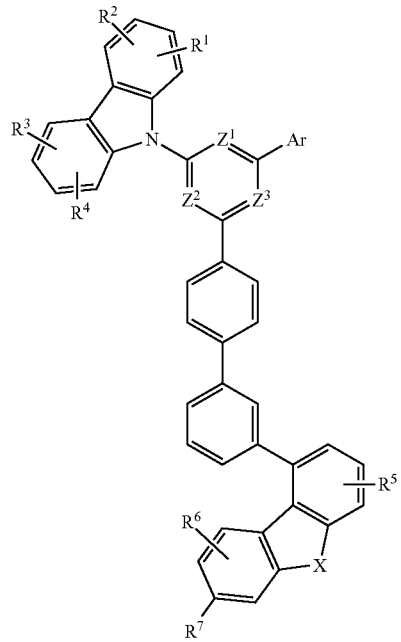

[Chemical Formula 1-1d]

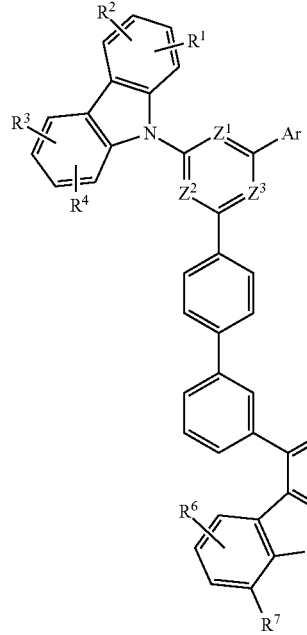

in Chemical Formula 1-1a to Chemical Formula 1-1d,
X is O or S,
$Z^1$ to $Z^3$ are independently N or $CR^a$, at least two of $Z^1$ to $Z^3$ being N,
Ar is a substituted or unsubstituted C6 to C18 aryl group,
$R^a$ and $R^1$ to $R^6$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof, and
$R^7$ is deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

4. The compound for an organic optoelectronic device as claimed in claim 2, wherein:

the compound represented by Chemical Formula 1 is represented by Chemical Formula 1-2, and the compound represented by Chemical Formula 1-2 is represented by one of Chemical Formula 1-2a to Chemical Formula 1-2d:

[Chemical Formula 1-2a]

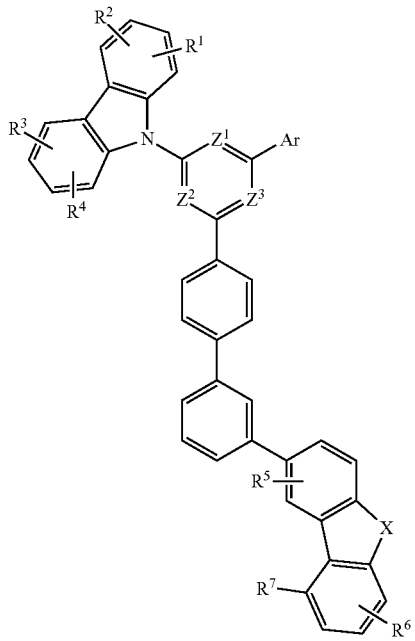

[Chemical Formula 1-2b]

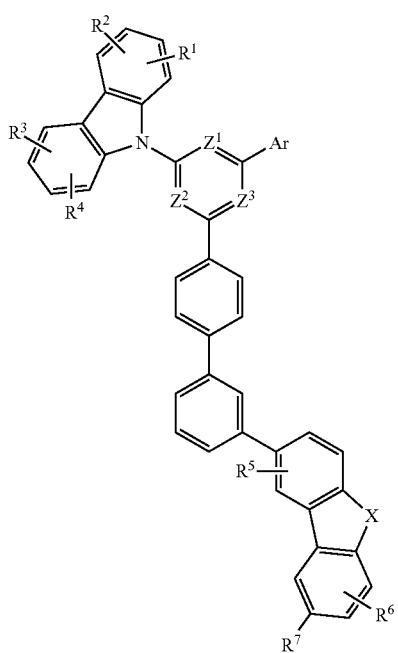

[Chemical Formula 1-2c]

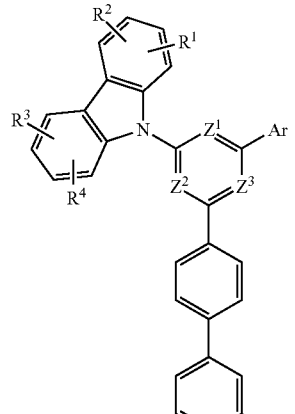

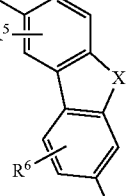

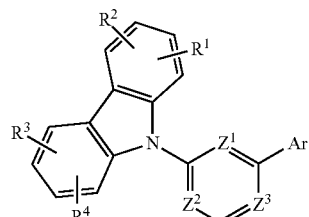

[Chemical Formula 1-2d]

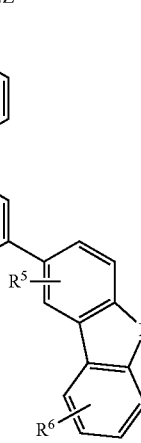

in Chemical Formula 1-2a to Chemical Formula 1-2d,

X is O or S, $Z^1$ to $Z^3$ are independently N or $CR^a$, at least two of $Z^1$ to $Z^3$ being N, Ar is a substituted or unsubstituted C6 to C18 aryl group, $R^a$ and $R^1$ to $R^6$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof, and $R^7$ is deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

5. The compound for an organic optoelectronic device as claimed in claim 2, wherein:

the compound represented by Chemical Formula 1 is represented by Chemical Formula 1-3, and the compound represented by Chemical Formula 1-3 is represented by one of Chemical Formula 1-3a to Chemical Formula 1-3d:

[Chemical Formula 1-3a]

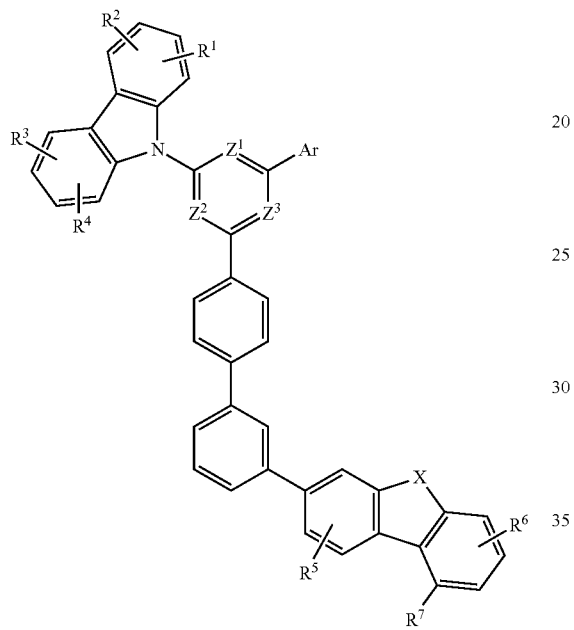

[Chemical Formula 1-3b]

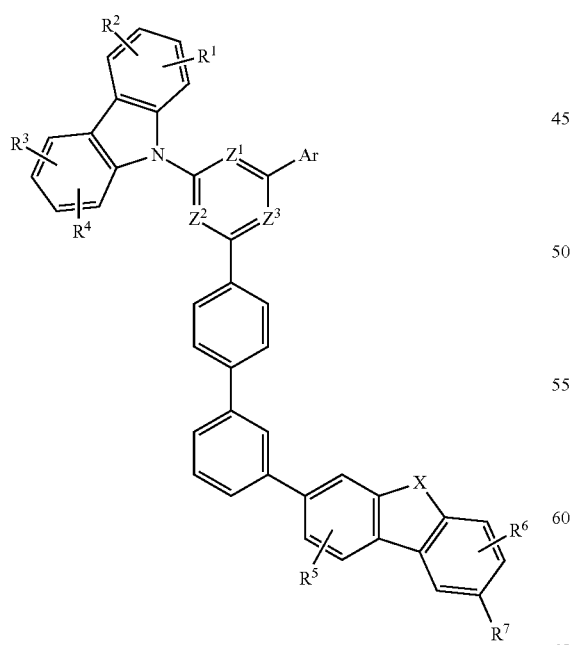

[Chemical Formula 1-3c]

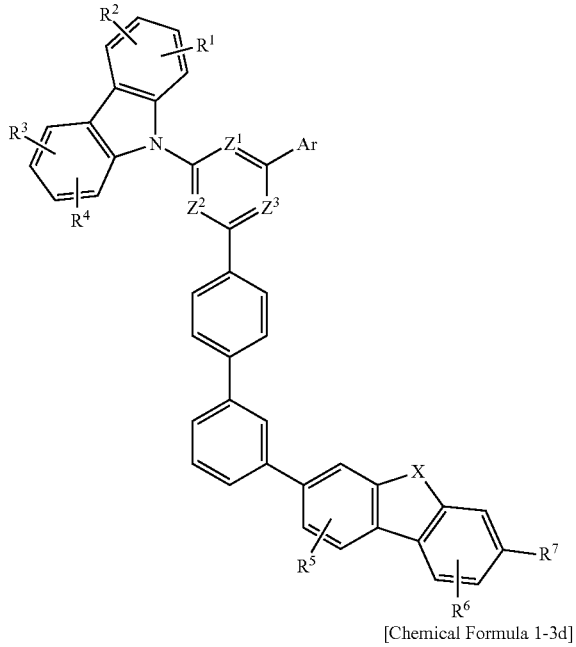

[Chemical Formula 1-3d]

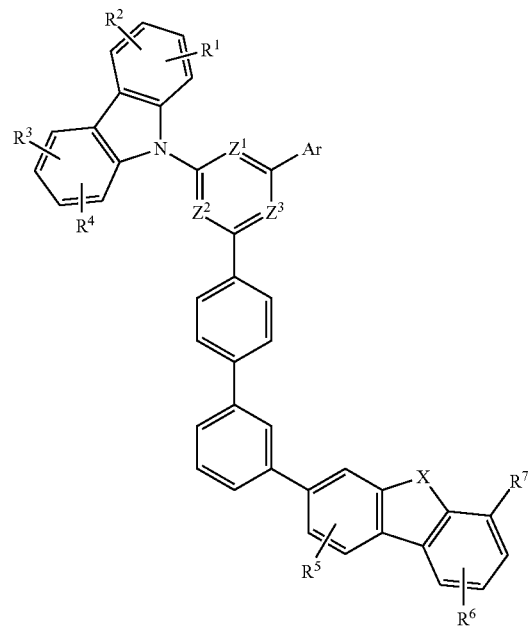

in Chemical Formula 1-3a to Chemical Formula 1-3d,

X is O or S, $Z^1$ to $Z^3$ are independently N or $CR^a$, at least two of $Z^1$ to $Z^3$ being N, Ar is a substituted or unsubstituted C6 to C18 aryl group, $R^a$ and $R^1$ to $R^6$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof, and $R^7$ is deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

6. The compound for an organic optoelectronic device as claimed in claim 2, wherein:

the compound represented by Chemical Formula 1 is represented by Chemical Formula 1-4, and the compound represented by Chemical Formula 1-4 is represented by one of Chemical Formula 1-4a to Chemical Formula 1-4d:

[Chemical Formula 1-4a]

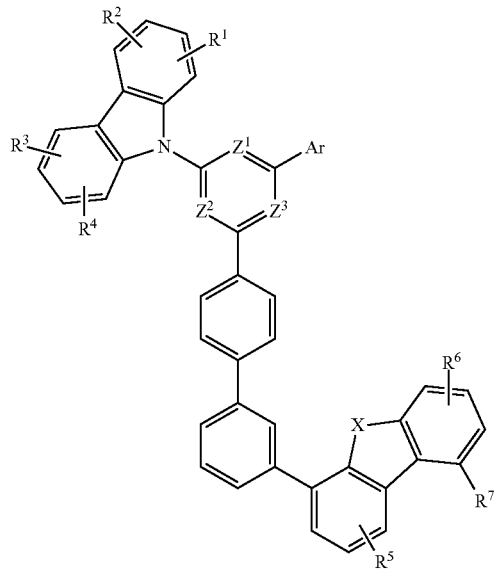

[Chemical Formula 1-4b]

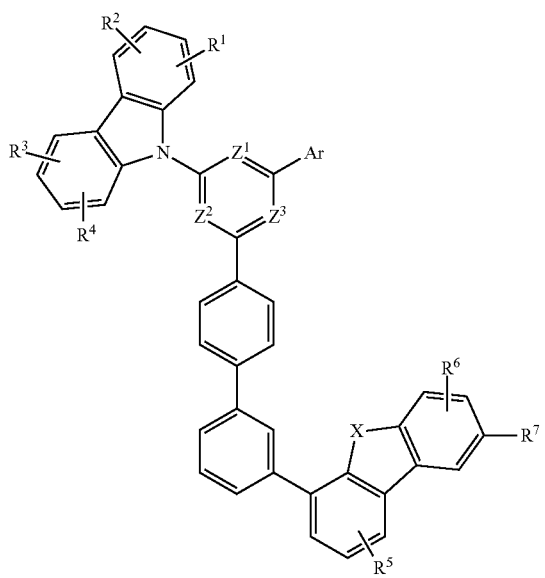

[Chemical Formula 1-4c]

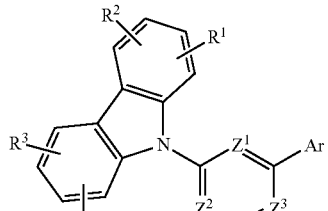

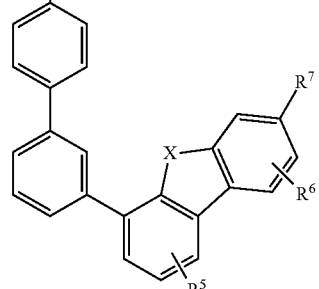

[Chemical Formula 1-4d]

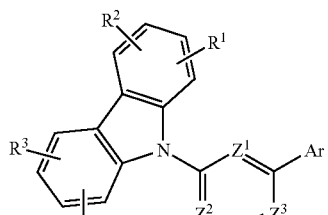

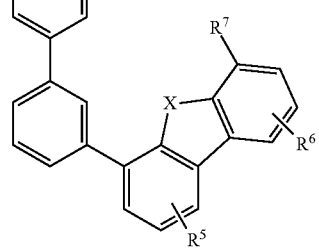

in Chemical Formula 1-4a to Chemical Formula 1-4d,

X is O or S, $Z^1$ to $Z^3$ are independently N or $CR^a$, at least two of $Z^1$ to $Z^3$ being N, Ar is a substituted or unsubstituted C6 to C18 aryl group, $R^a$ and $R^1$ to $R^6$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof, and $R^7$ is deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

7. The compound for an organic optoelectronic device as claimed in claim 1, wherein the compound represented by Chemical Formula 1 is represented by Chemical Formula 1-1a, Chemical Formula 1-1b, Chemical Formula 1-3a, Chemical Formula 1-3b, Chemical Formula 1-4a, or Chemical Formula 1-4b:
[Chemical Formula 1-1a]
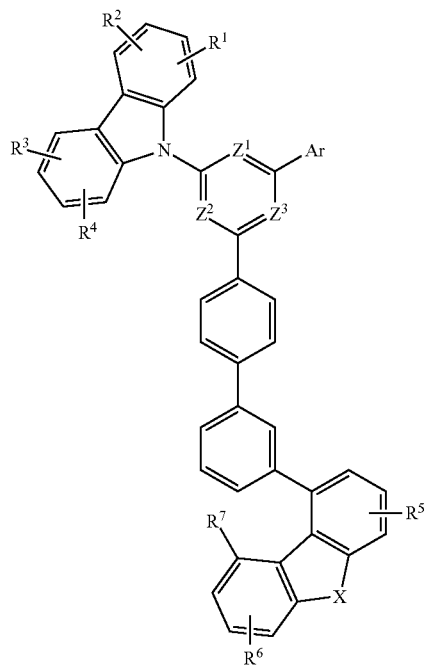
[Chemical Formula 1-1b]
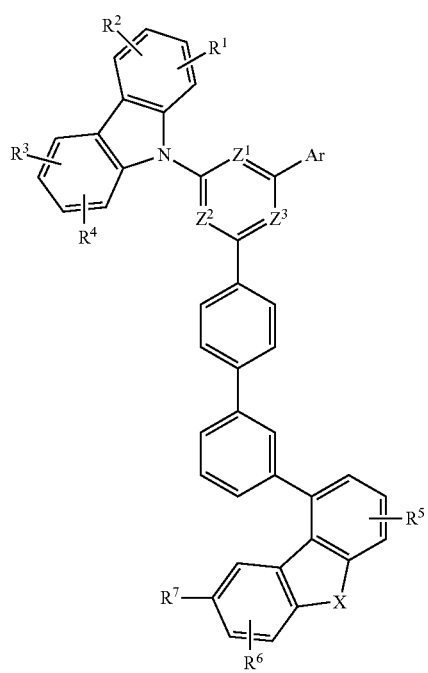
[Chemical Formula 1-3a]
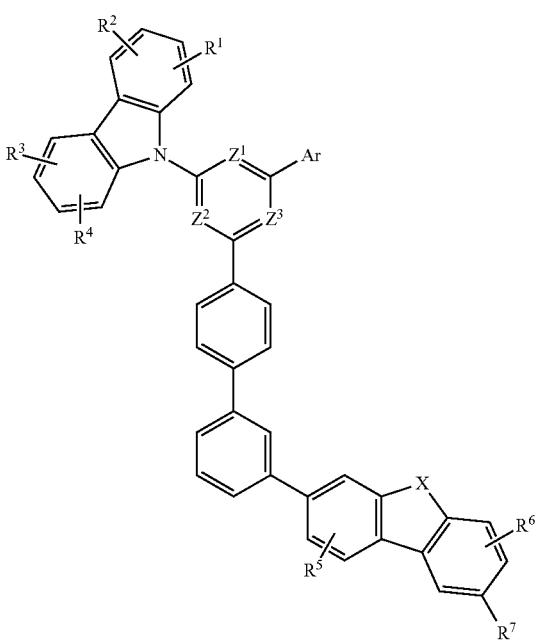
[Chemical Formula 1-3b]

-continued

[Chemical Formula 1-4a]

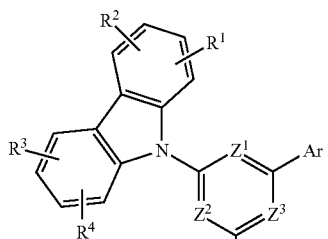

[Chemical Formula 1-4b]

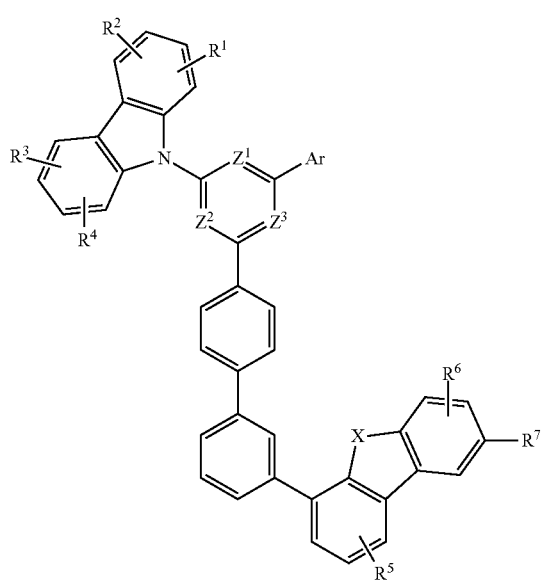

wherein, in Chemical Formula 1-1a, Chemical Formula 1-1b, Chemical Formula 1-3a, Chemical Formula 1-3b, Chemical Formula 1-4a, and Chemical Formula 1-4b, X is O or S, $Z^1$ to $Z^3$ are independently N or $CR^a$, at least two of $Z^1$ to $Z^3$ being N, Ar is a substituted or unsubstituted C6 to C18 aryl group, $R^a$ and $R^1$ to $R^6$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof, and $R^7$ is deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof.

8. The compound for an organic optoelectronic device as claimed in claim 1, wherein Ar is a substituted or unsubstituted phenyl group, a substituted or unsubstituted biphenyl group, or a substituted or unsubstituted terphenyl group.

9. The compound for an organic optoelectronic device as claimed in claim 1, wherein:

Ar is a group of the following Group I,

[Group I]

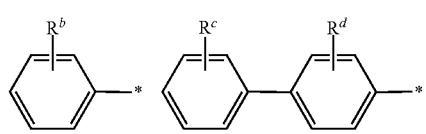

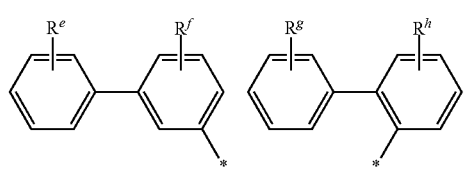

in Group I, $R^b$, $R^c$, $R^d$, $R^e$, $R^f$, $R^g$, and $R^h$ are independently hydrogen, deuterium, a cyano group, a nitro group, a halogen, a substituted or unsubstituted C1 to C30 alkyl group, or a combination thereof.

10. The compound for an organic optoelectronic device as claimed in claim 1, wherein the compound is a compound of the following Group 1:

[Group 1]

1

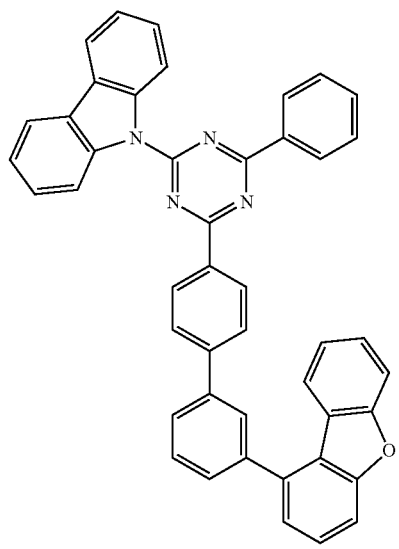

121
-continued
2
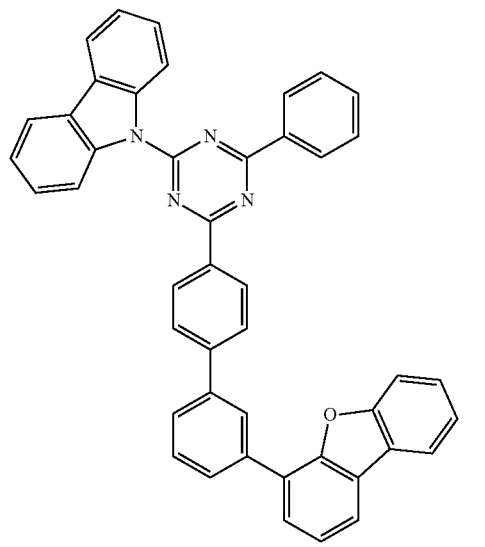
3
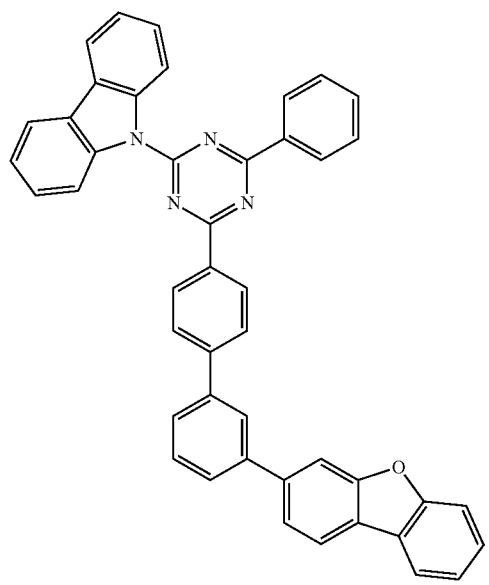
4
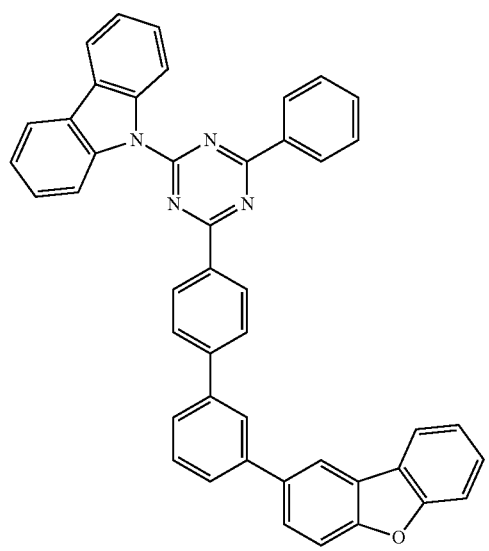
122
-continued
5
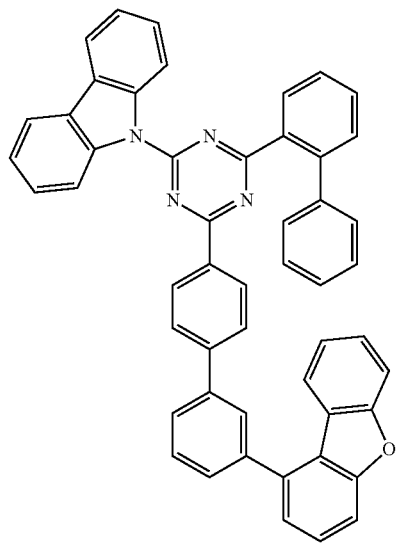
6
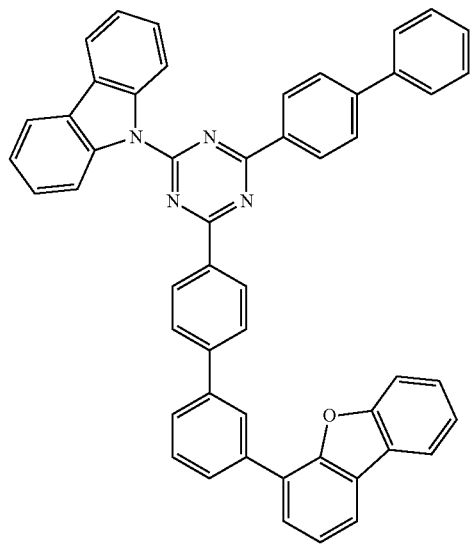
7
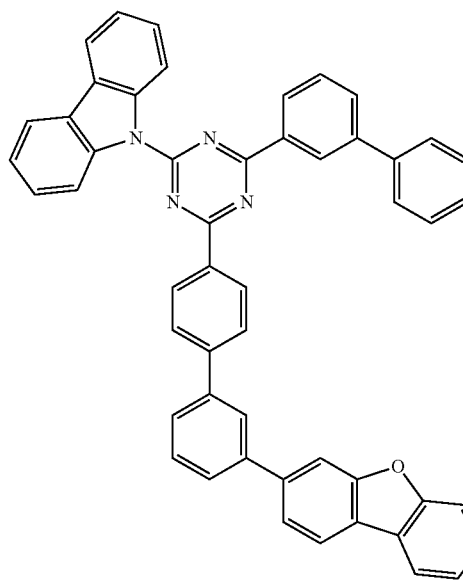

123
-continued
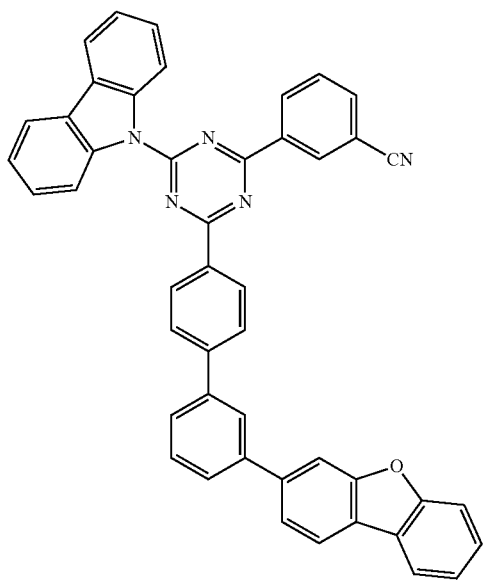
124
-continued
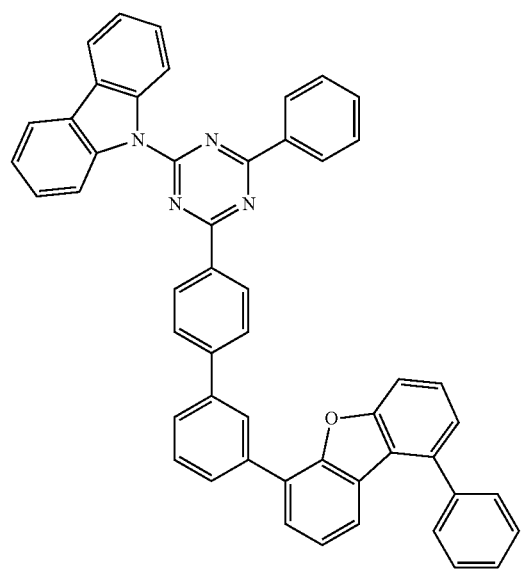

125
-continued
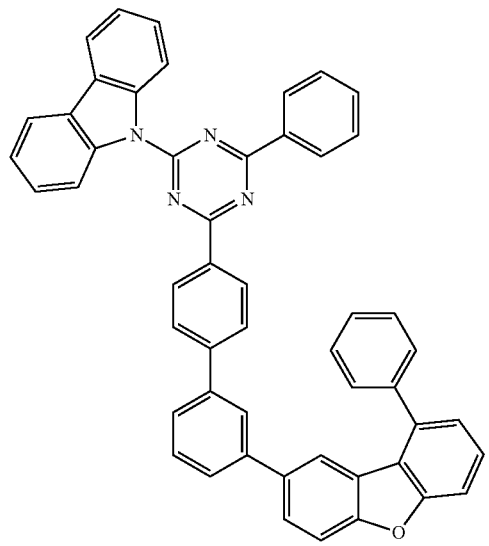
126
-continued
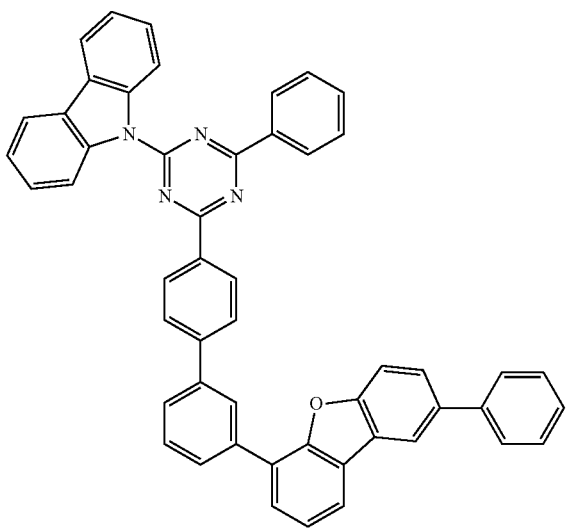
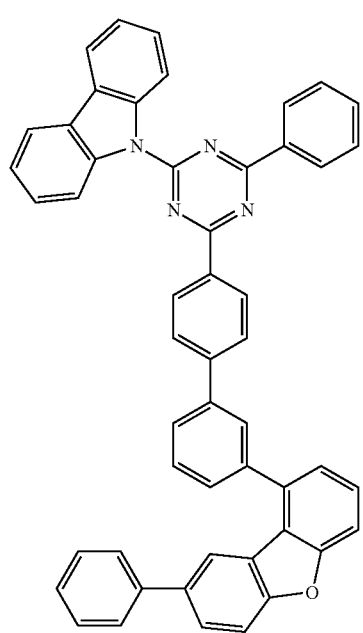
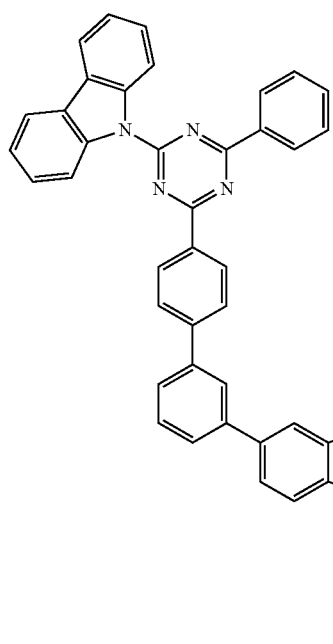

127
-continued
16
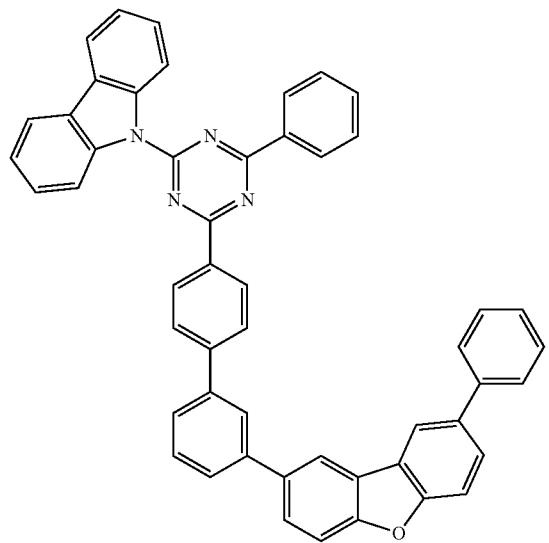
17
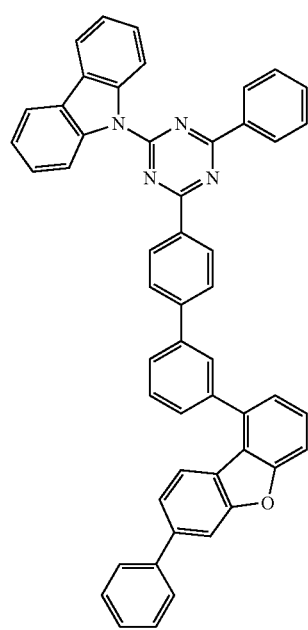
128
-continued
18
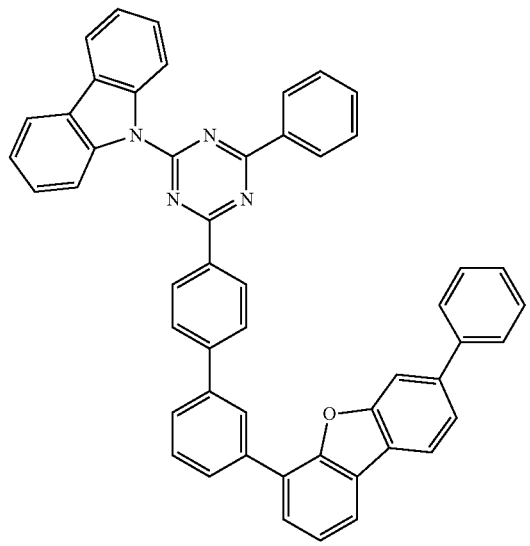
19
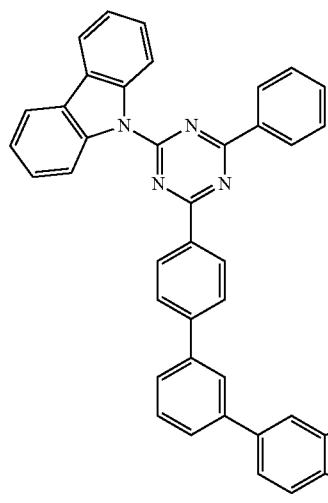
20
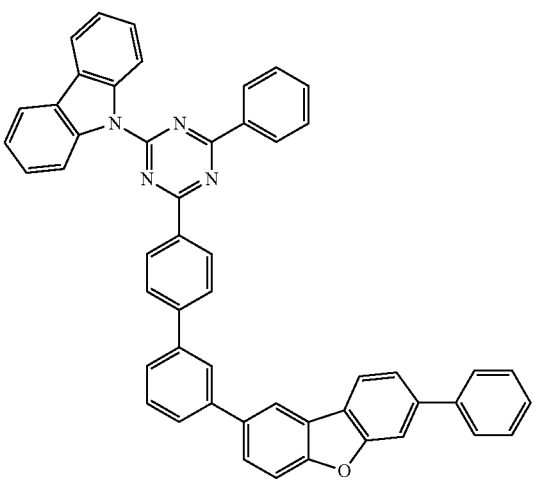

129
-continued
21
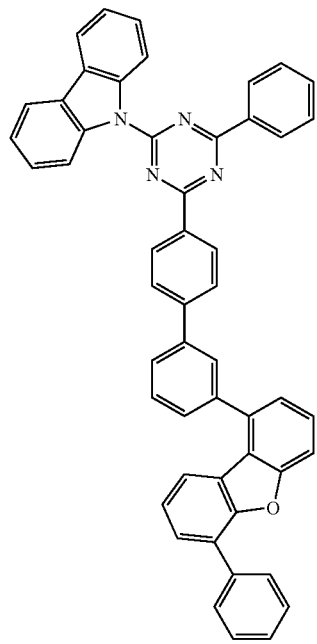
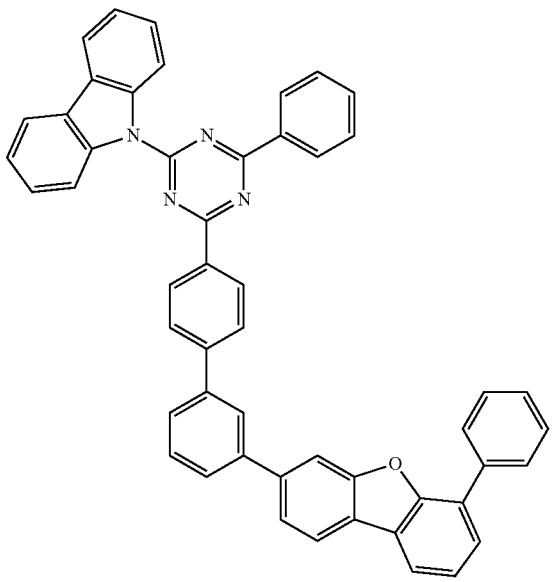
130
-continued
23
22
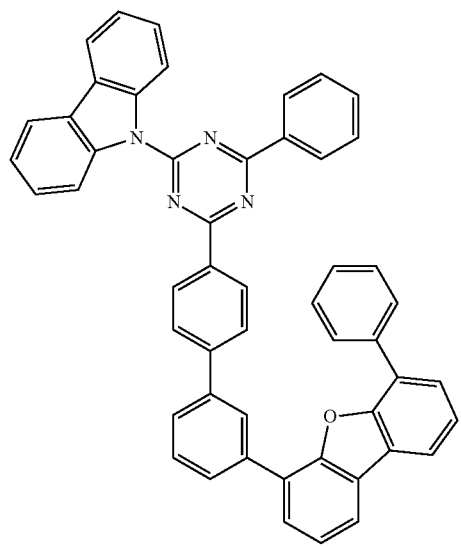
24
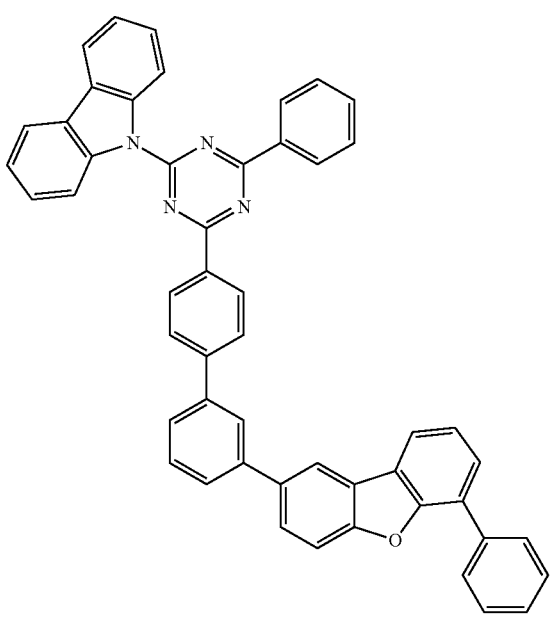

131
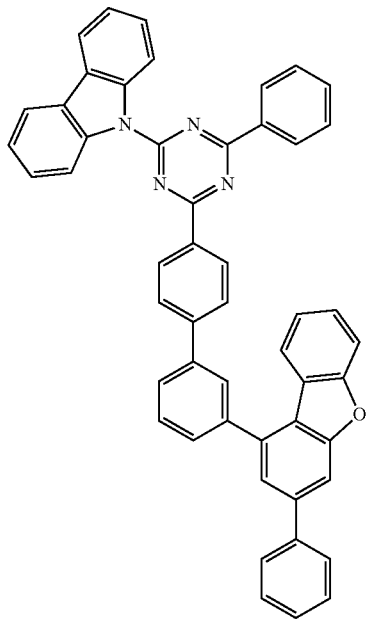
26
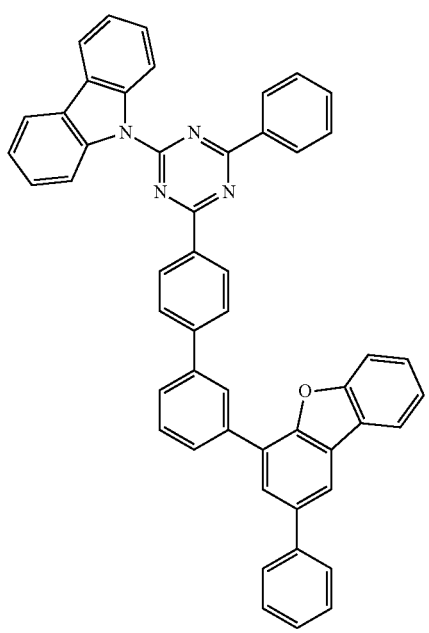
132
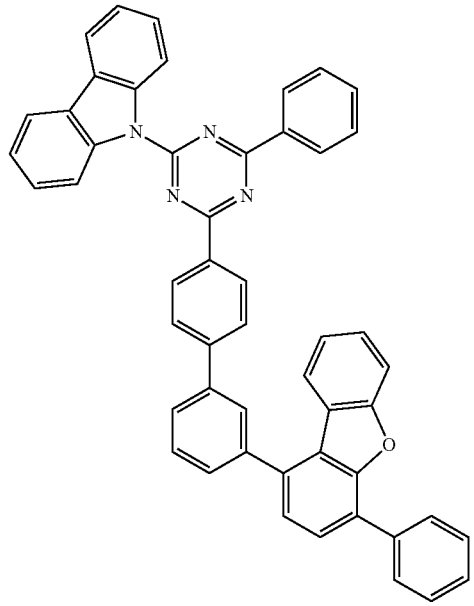
28
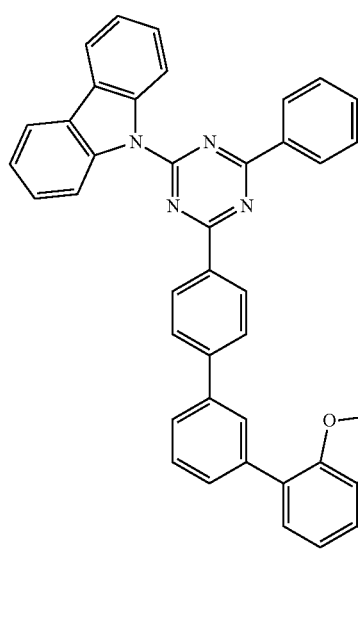

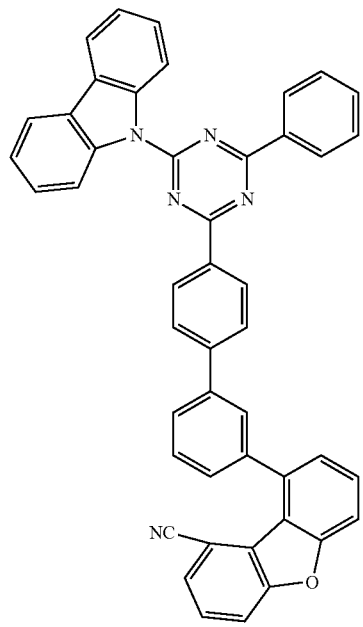
29
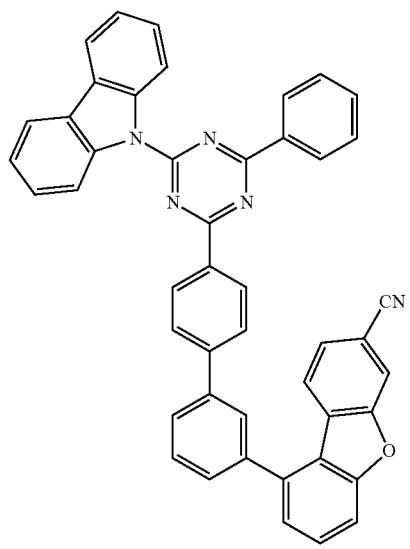
31
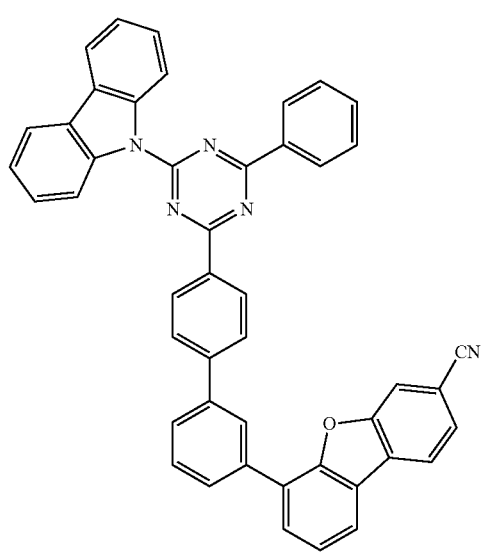
32
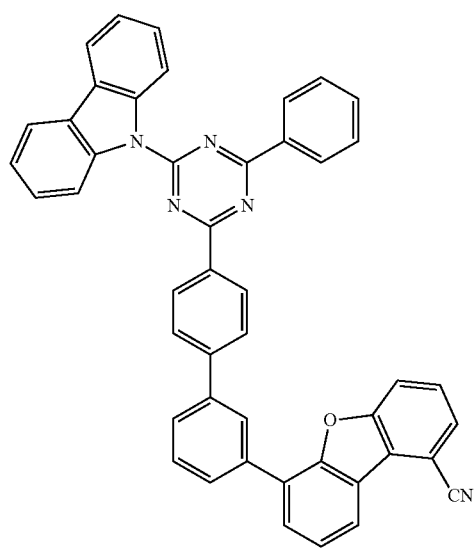
30
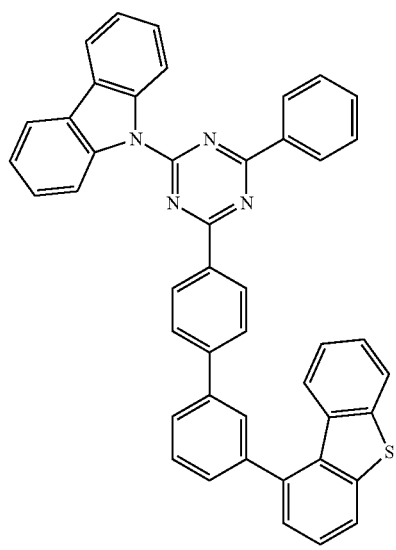
33

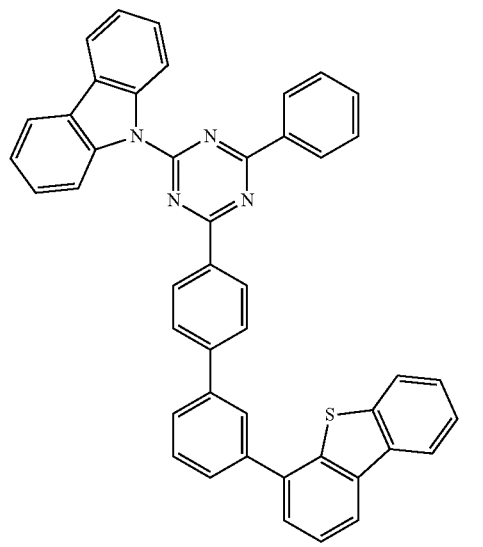
34
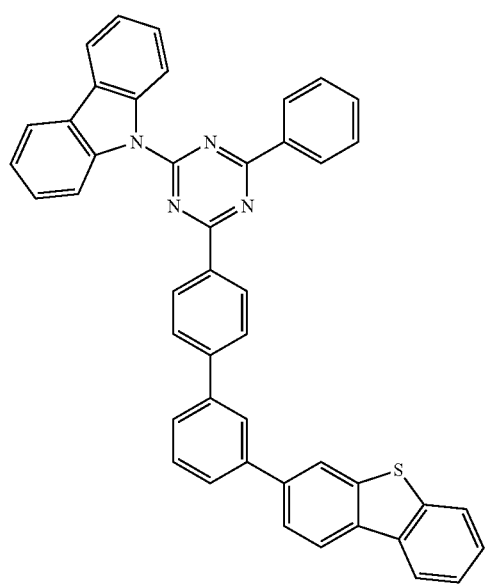
35
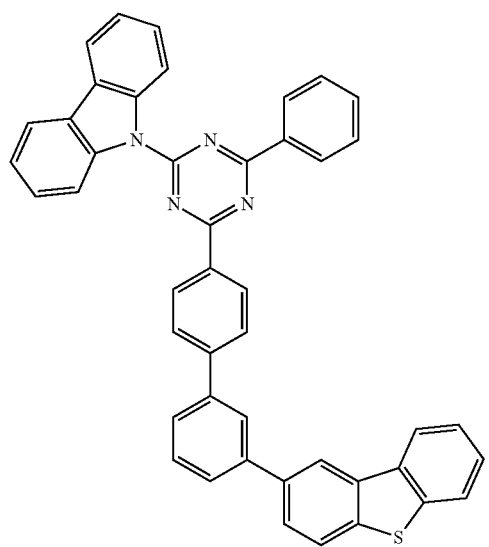
36
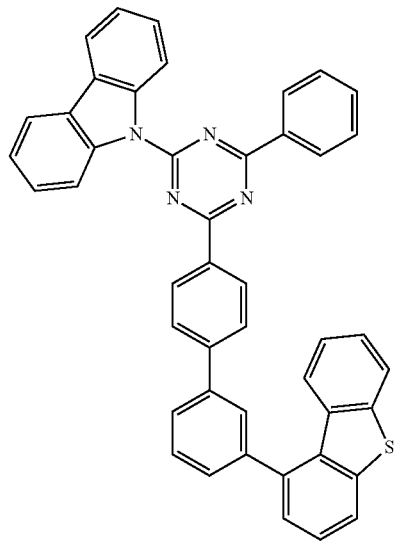
37
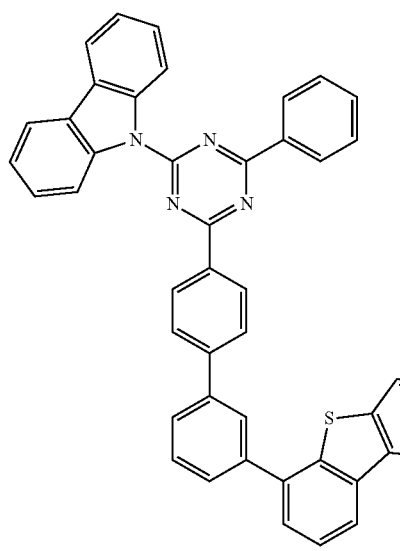
38
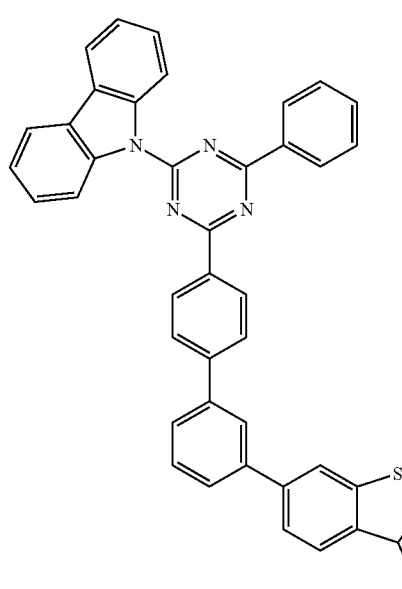
39

137
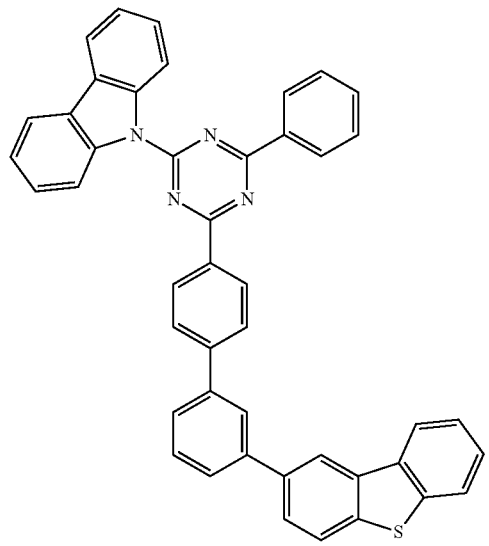
138
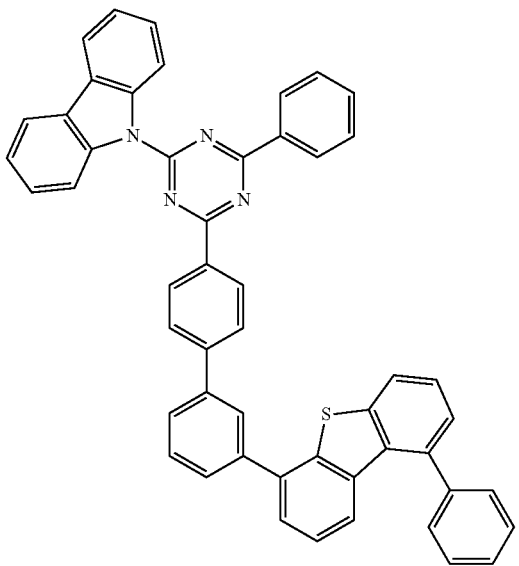
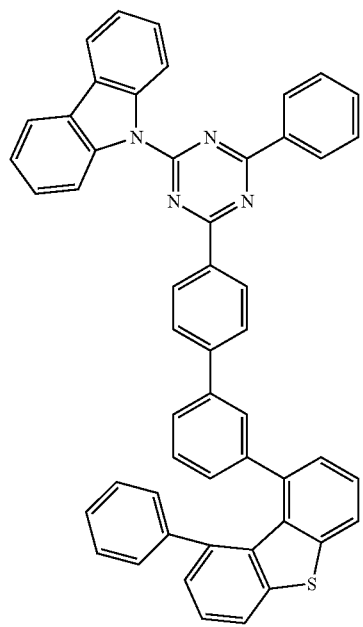
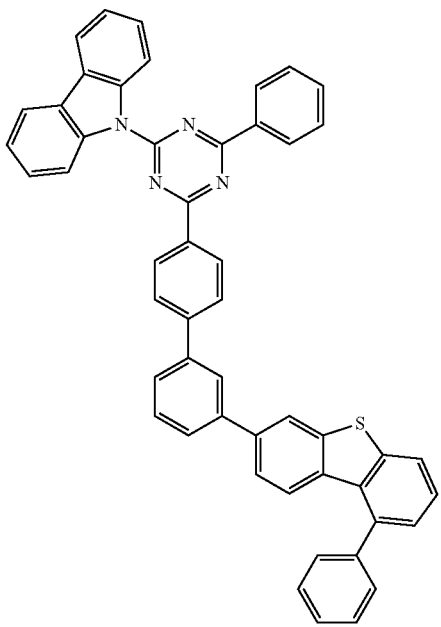

44
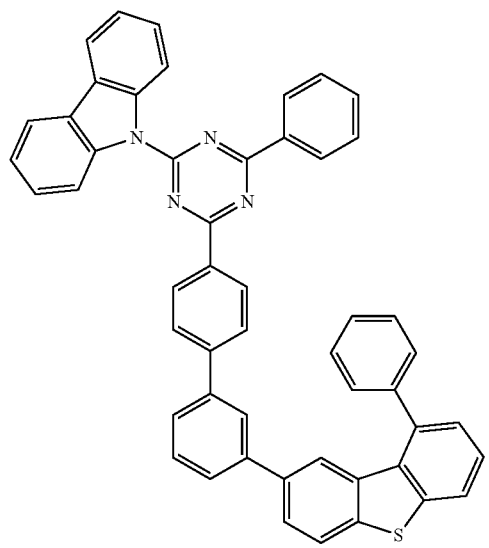
46
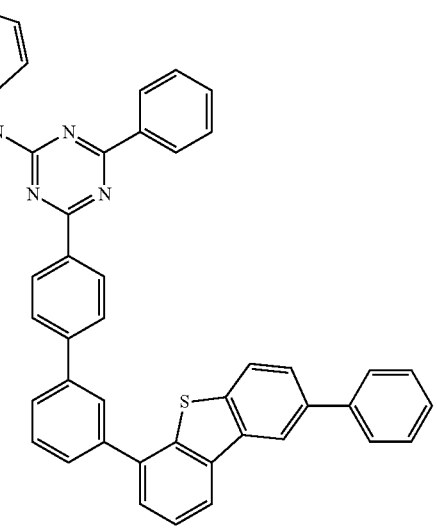
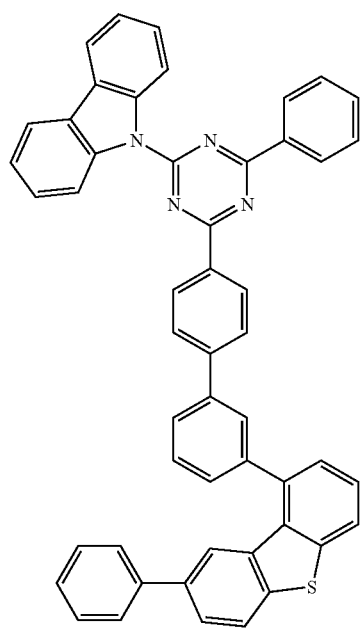
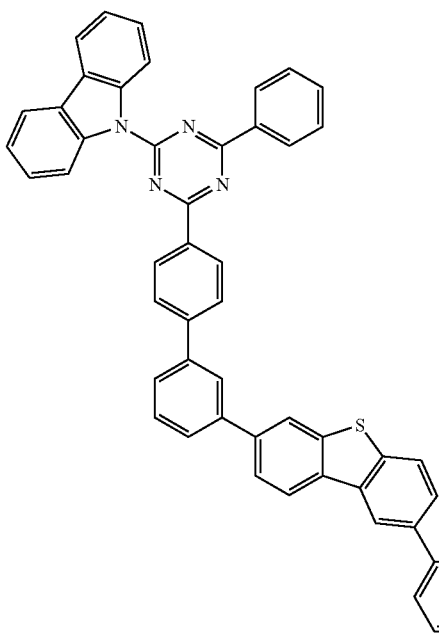

48
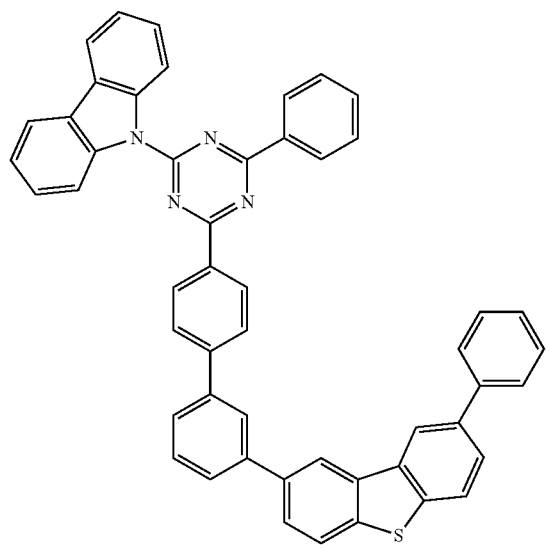
49
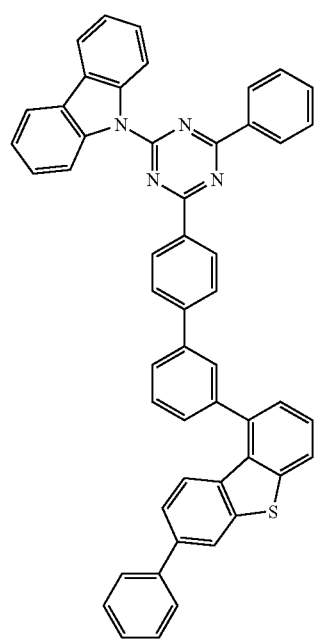
50
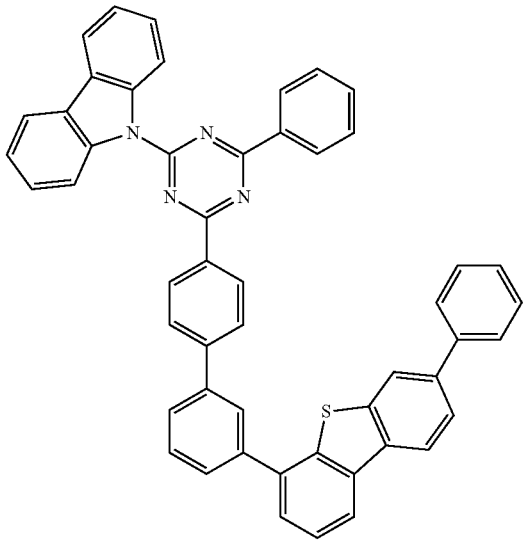
51
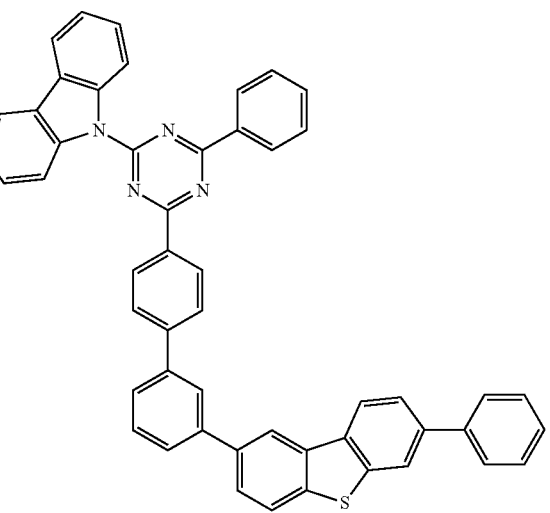

53
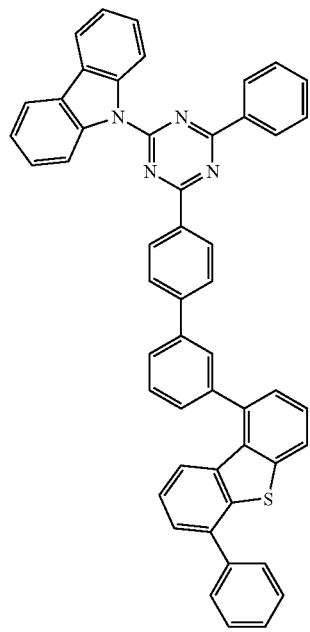
54
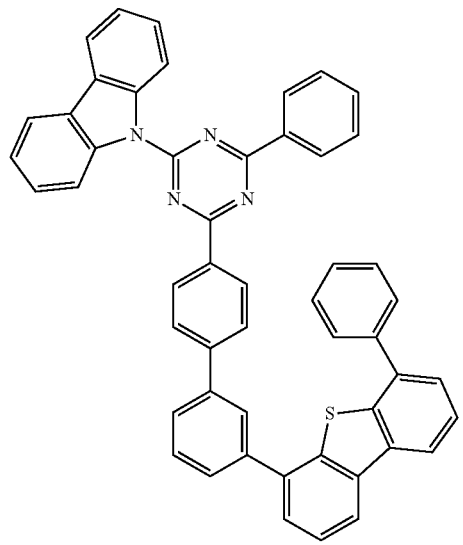
55
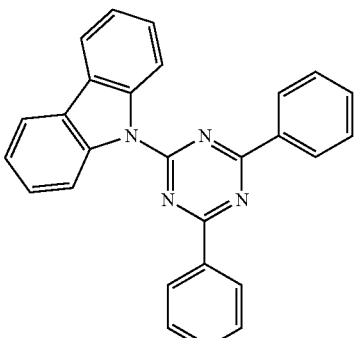
56
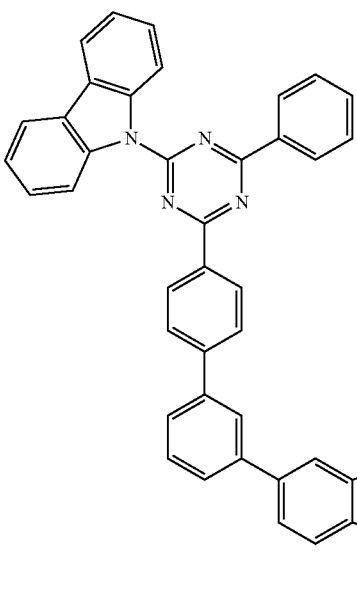

57
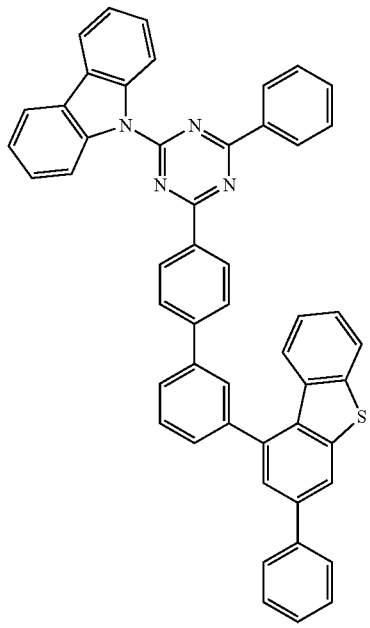
58
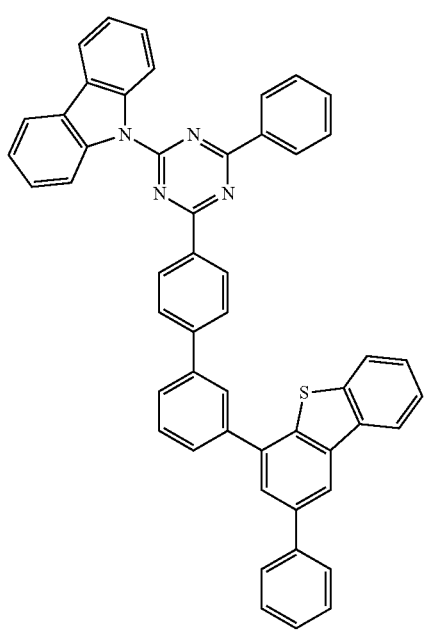
59
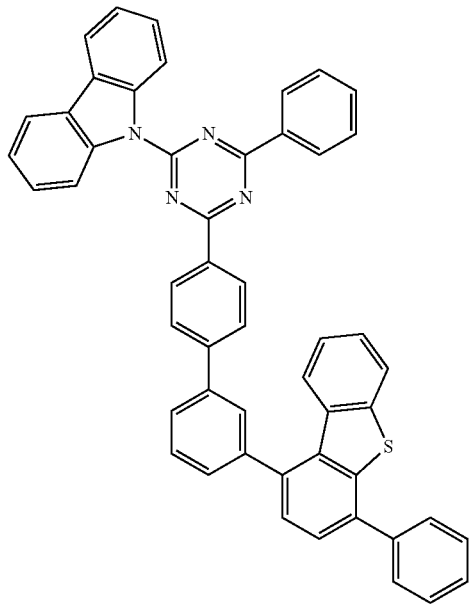
60
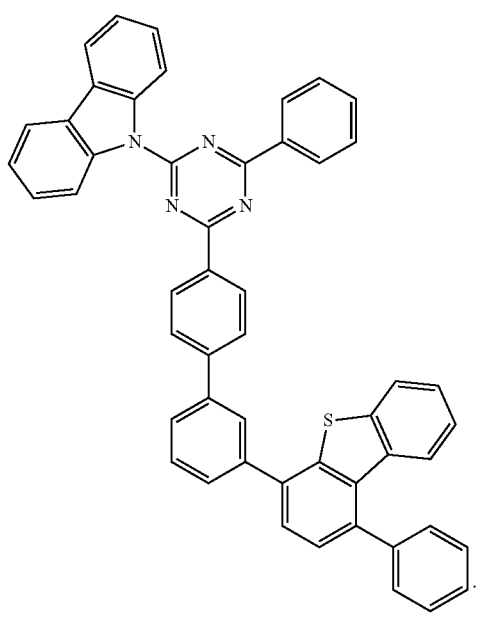
11. A composition for an organic optoelectronic device, the composition comprising:
a first compound and a second compound,
wherein:
the first compound includes the compound as claimed in claim 1,
the second compound is represented by Chemical Formula 2,

[Chemical Formula 2]

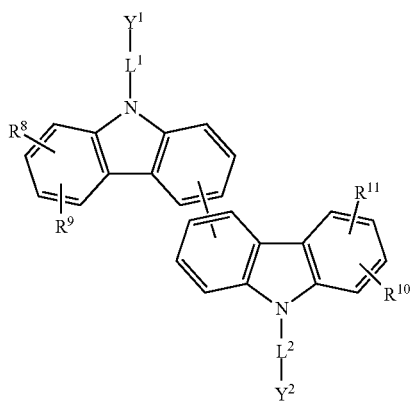

in Chemical Formula 2, $L^1$ and $L^2$ are independently a single bond or a substituted or unsubstituted C6 to C30 arylene group, $Y^1$ and $Y^2$ are independently a substituted or unsubstituted C6 to C30 aryl group, a substituted or unsubstituted C2 to C30 heterocyclic group, or a combination thereof, and $R^8$ to $R^{11}$ are independently hydrogen, deuterium, a cyano group, a halogen, a substituted or unsubstituted C1 to C10 alkyl group, a substituted or unsubstituted C6 to C12 aryl group, or a combination thereof.

12. An organic optoelectronic device, comprising:
an anode and a cathode facing each other, and
at least one organic layer between the anode and the cathode,
wherein the at least one organic layer includes the compound as claimed in claim 1.

13. The organic optoelectronic device as claimed in claim 12, wherein:
the at least one organic layer includes a light emitting layer, and
the light emitting layer includes the compound.

14. A display device including the organic optoelectronic device as claimed in claim 12.

15. An organic optoelectronic device, comprising:
an anode and a cathode facing each other,
at least one organic layer between the anode and the cathode,
wherein the at least one organic layer includes the composition as claimed in claim 11.

16. The organic optoelectronic device as claimed in claim 15, wherein:
the organic layer includes a light emitting layer, and
the light emitting layer includes the composition.

17. A display device comprising the organic optoelectronic device as claimed in claim 15.

* * * * *